(12) United States Patent
Zong

(10) Patent No.: US 11,162,134 B2
(45) Date of Patent: Nov. 2, 2021

(54) METHODS OF WHOLE TRANSCRIPTOME AMPLIFICATION

(71) Applicant: Baylor College of Medicine, Houston, TX (US)

(72) Inventor: Chenghang Zong, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 211 days.

(21) Appl. No.: 16/088,704

(22) PCT Filed: Mar. 31, 2017

(86) PCT No.: PCT/US2017/025472
§ 371 (c)(1),
(2) Date: Sep. 26, 2018

(87) PCT Pub. No.: WO2017/173328
PCT Pub. Date: Oct. 5, 2017

(65) Prior Publication Data
US 2020/0299759 A1  Sep. 24, 2020

Related U.S. Application Data

(60) Provisional application No. 62/316,880, filed on Apr. 1, 2016.

(51) Int. Cl.
*C12Q 1/6853* (2018.01)
*C12Q 1/6806* (2018.01)
*C12N 15/10* (2006.01)

(52) U.S. Cl.
CPC ....... *C12Q 1/6853* (2013.01); *C12N 15/1096* (2013.01); *C12Q 1/6806* (2013.01)

(58) Field of Classification Search
CPC ............ C12Q 1/6806; C12Q 2521/107; C12Q 2521/131
See application file for complete search history.

(56) References Cited

U.S. PATENT DOCUMENTS

| 6,197,554 B1 | 3/2001 | Lin et al. |
| 2014/0200146 A1 | 7/2014 | Xie et al. |

FOREIGN PATENT DOCUMENTS

| WO | 2011/032053 A1 | 3/2011 |
| WO | 2015/171656 A1 | 11/2015 |

OTHER PUBLICATIONS

Kurimoto, K. et al., An improved single-cell cDNA amplification method for efficient high-density oligonucleotide microarray analysisNucl. Acids Res., vol. 34, e42, pp. 1-17 (Year: 2006).*
Belyavsky, A. et al., PCR-based cDNA library construction: general cDNA libraries at the level of a few cells, Nucl. Acids Res., vol. 17, pp. 2919-2932 (Year: 1989).*
Dresselhaus, T. et al., Representative eDNA libraries from few plant cells, The Plant J., vol. 5, pp. 605-610 (Year: 1994).*
Ramskold, D. et al., Full-length mRNA-Seq from single-cell levels of RNA and individual circulating tumor cells, Nature Biotech., vol. 8, pp. 777-782 plus online methods pp. 1-3 (Year: 2012).*
Sheng et al. "Effective Detection of Variation in Single-Cell Transcriptomes Using MATO-seq," Nature Methods, Mar. 1, 2017 (Mar. 1, 2017), vol. 14, pp. 267-270.
Eberwine et al. "Analysis of Gene Expression in Single Live Neurons," Proceedings of the National Academy of Sciences, Apr. 1, 1992 (Apr. 1, 1992), vol. 89, pp. 3010-3014.
Zong et al. "Genome-Wide Detection of Single-Nucleotide and Copy-Number Variations of a Single Human Cell," Science, Dec. 21, 2012 (Dec. 21, 2012), vol. 338, pp. 1622-1626.
Chapman et al., "Single Cell Transcriptome Amplification with MALBAC", PLOS One, vol. 10, No. 3, Jan. 1, 2015 (Jan. 1, 2015), p. e01208890.
Saliba et al., "Single-cell RNA-seq: advances and future challenges", Nucleic Acids Research, vol. 42, No. 14, Jul. 22, 2014 (Jul. 22, 2014), pp. 8845-8860.

* cited by examiner

*Primary Examiner* — Teresa E Strzelecka
(74) *Attorney, Agent, or Firm* — Norton Rose Fulbright US LLP

(57) ABSTRACT

Embodiments of the disclosure encompass highly sensitive and quantitative methods for single-cell sequencing of total RNA. In particular cases, methods utilize annealing of multiple primers to RNA, polytailing of single stranded DNA reverse transcribed therefrom, and utilization of bar codes in primers for amplification of amplicons produced from second strand synthesis.

18 Claims, 27 Drawing Sheets
Specification includes a Sequence Listing.

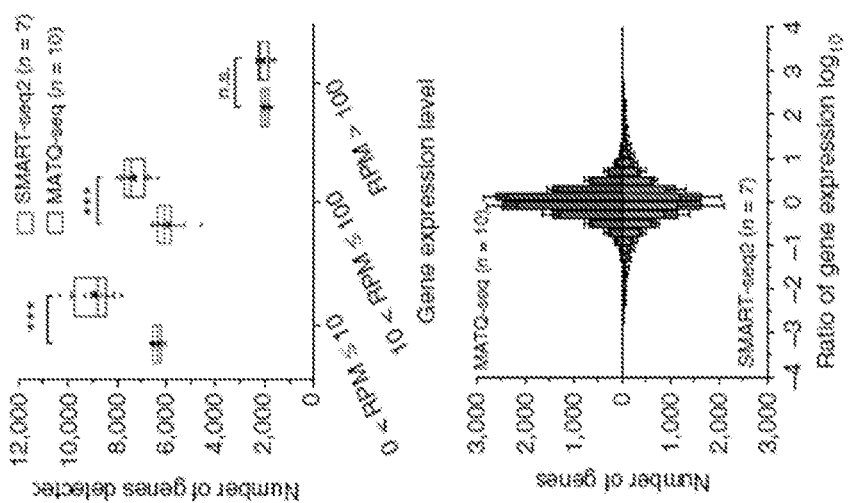
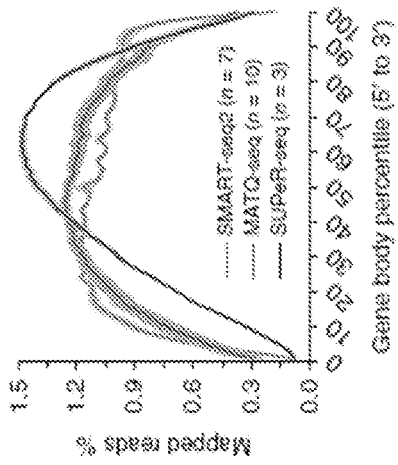
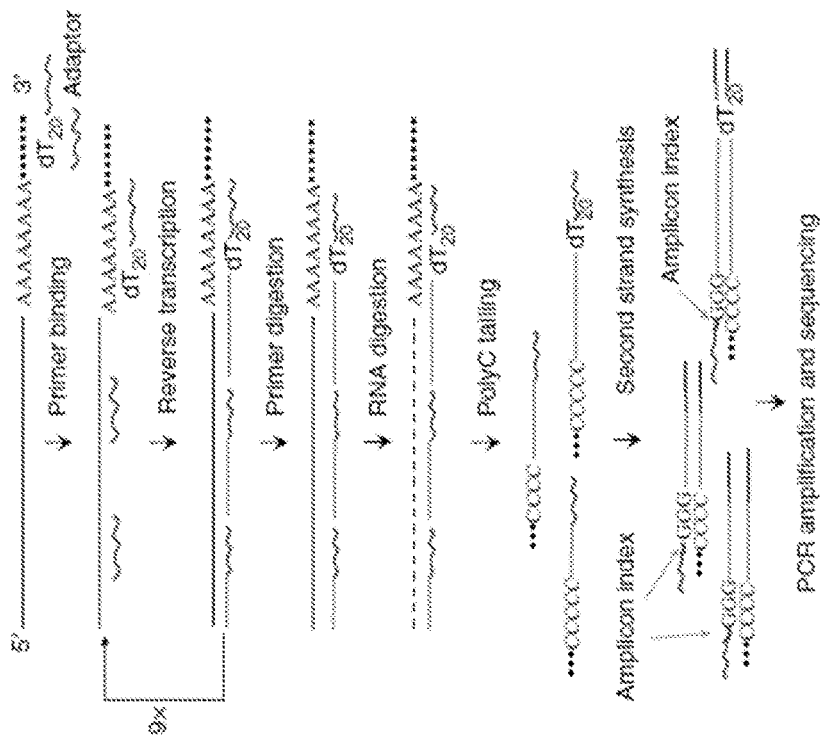

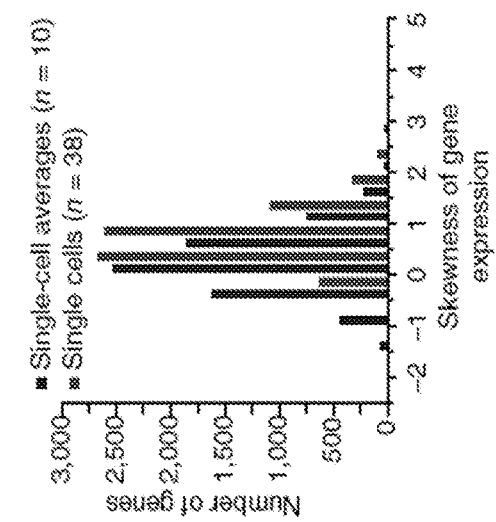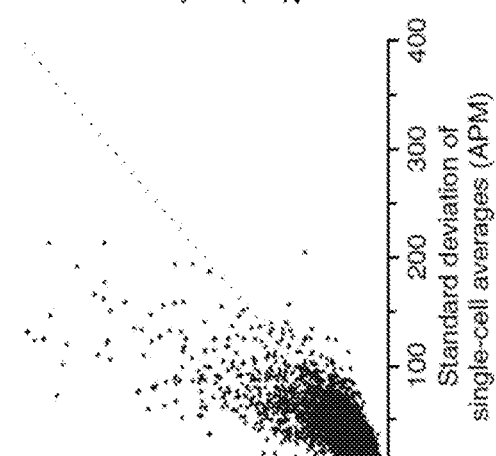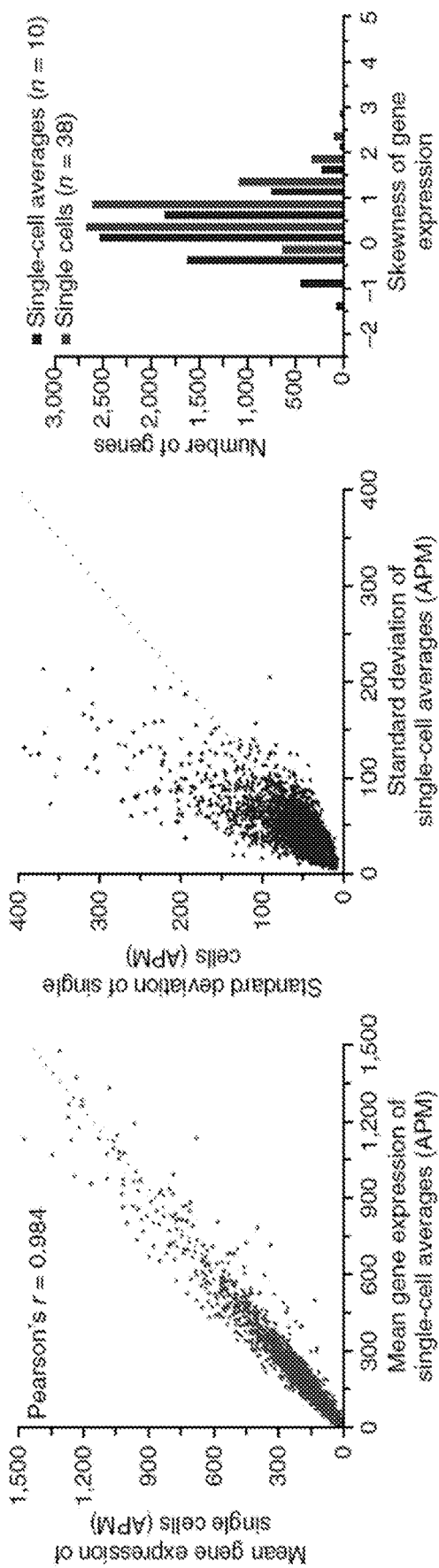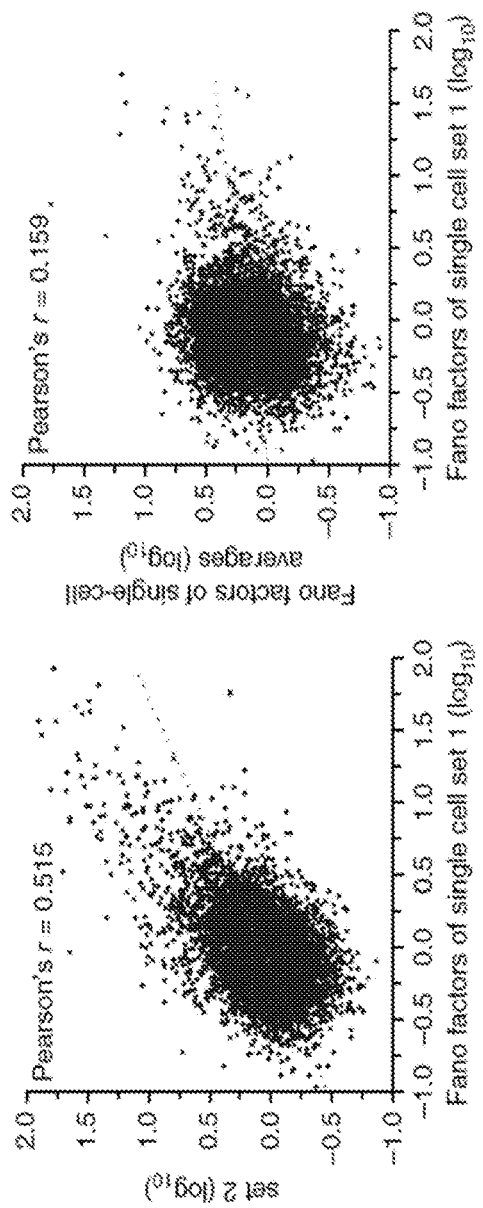
FIG. 3A  FIG. 3B  FIG. 3C  FIG. 3D  FIG. 3E

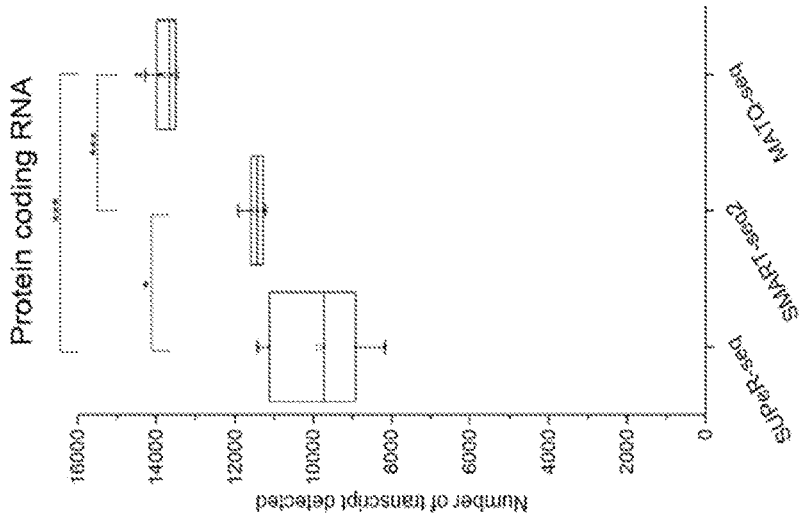
FIG. 4C
FIG. 4B
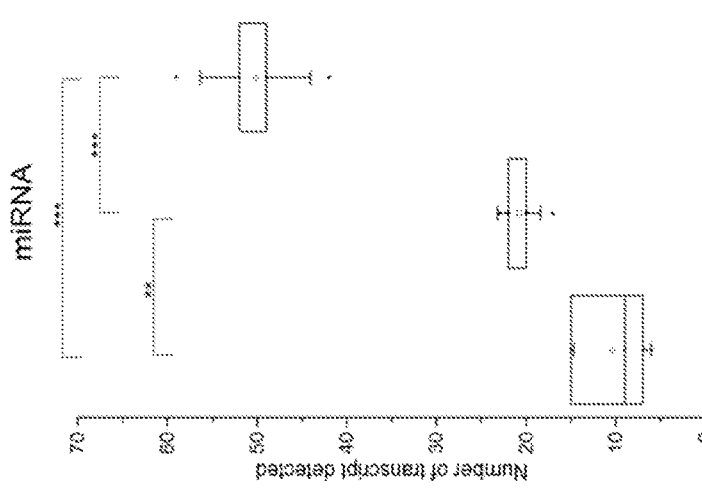
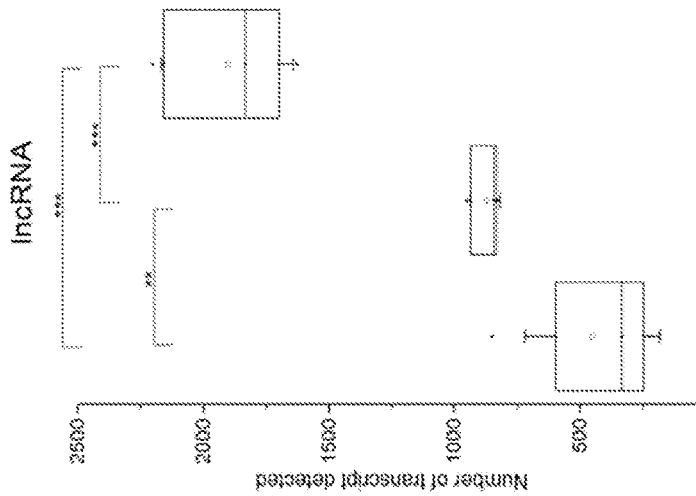
FIG. 4A

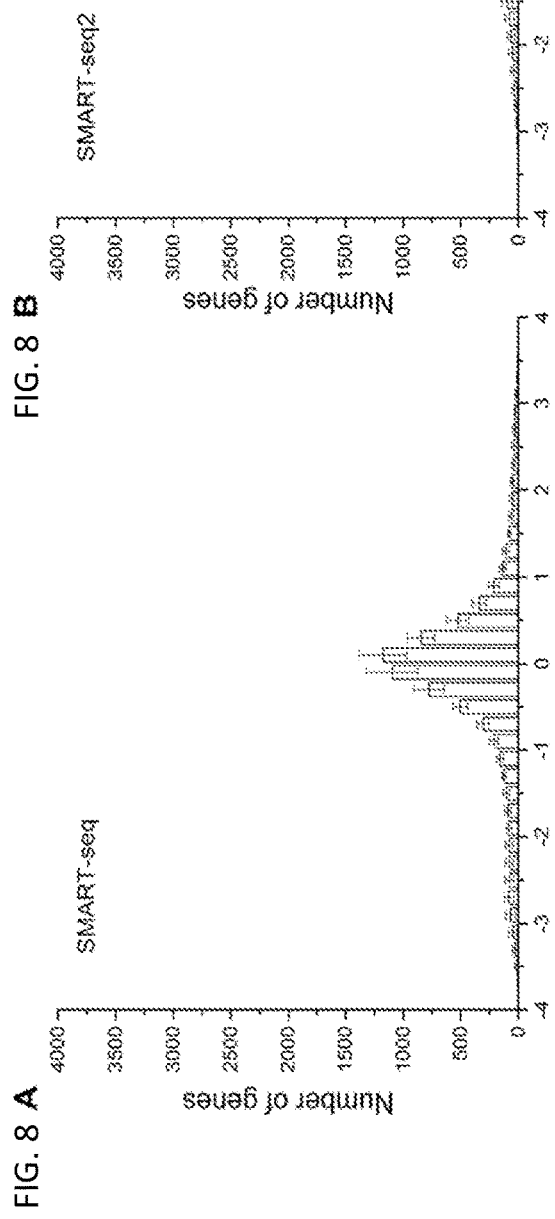
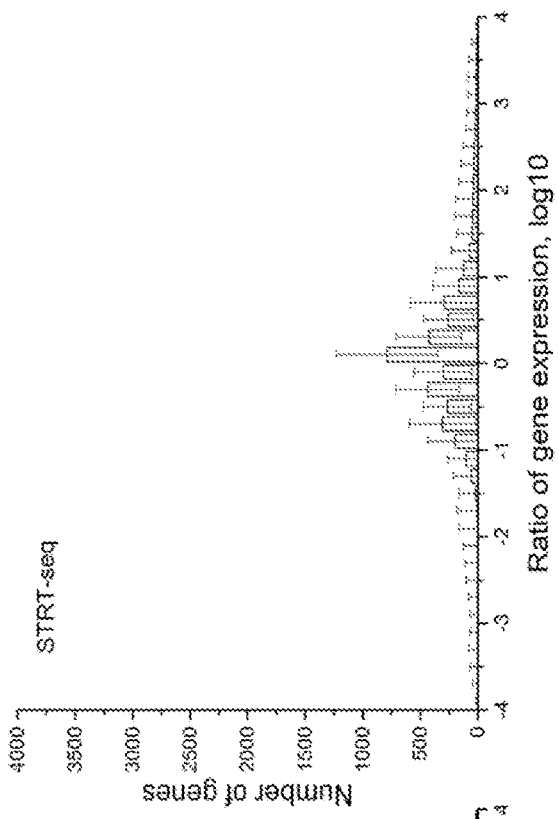
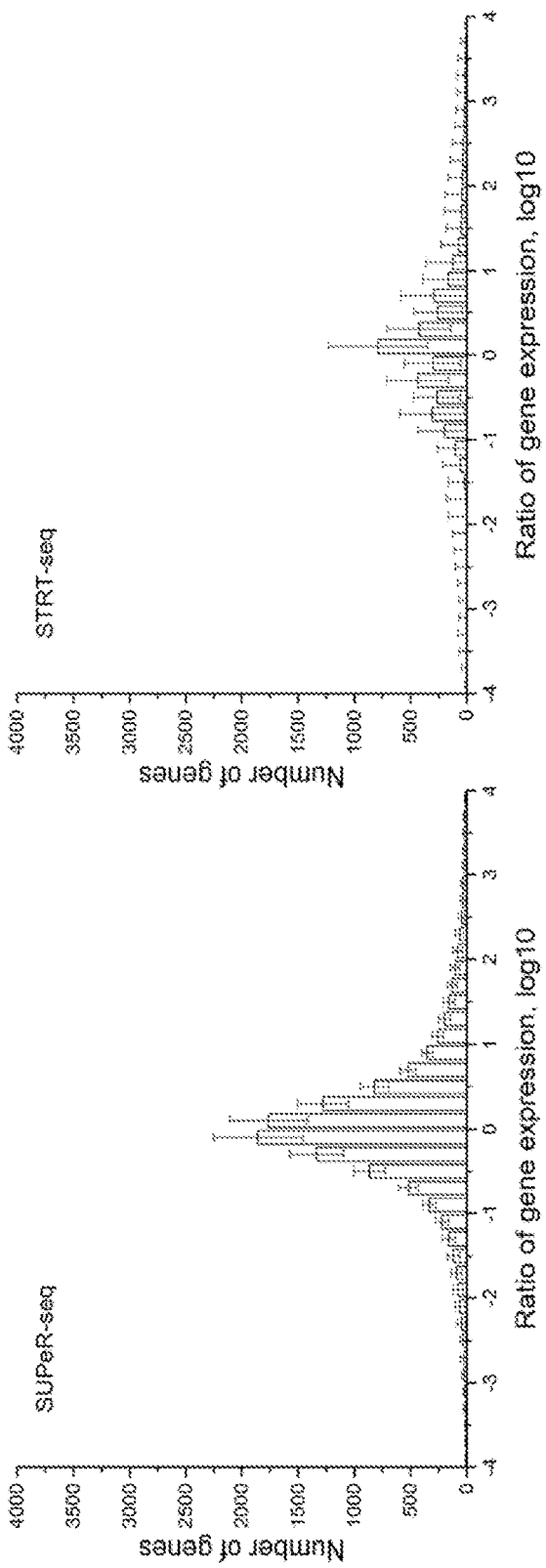

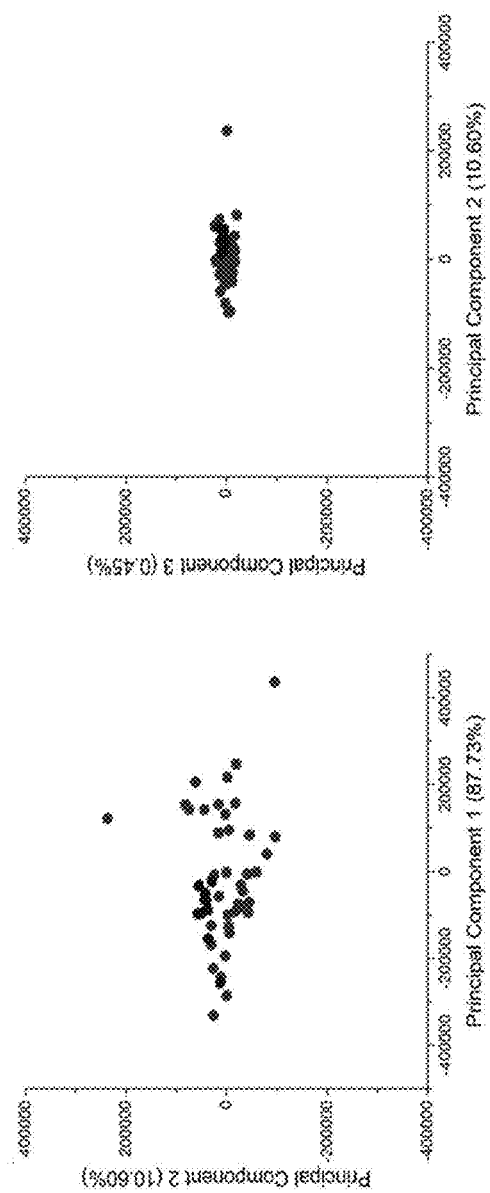
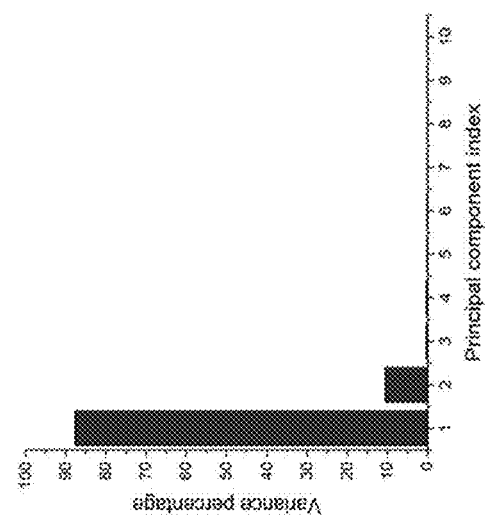
FIG. 10A
FIG. 10B
FIG. 10C
• Single cells  • Single-cell averages

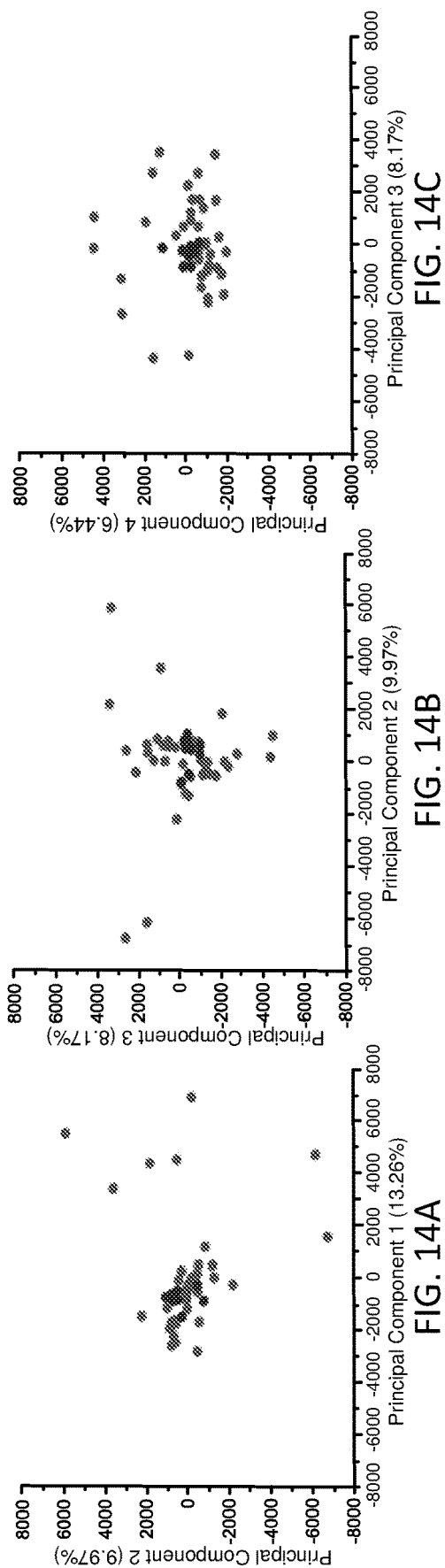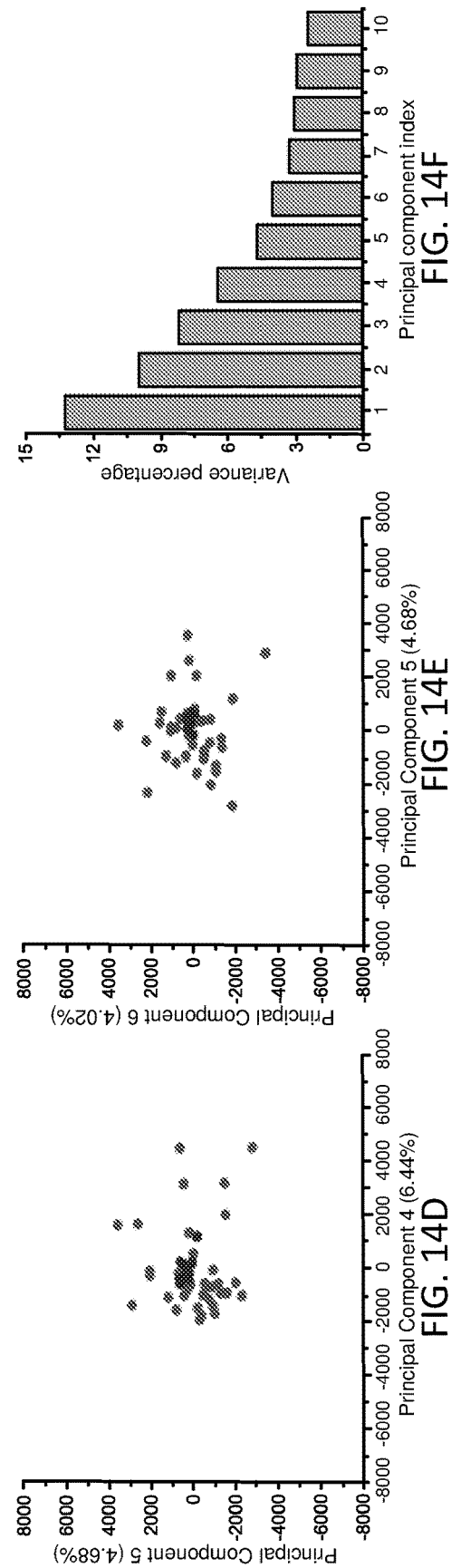

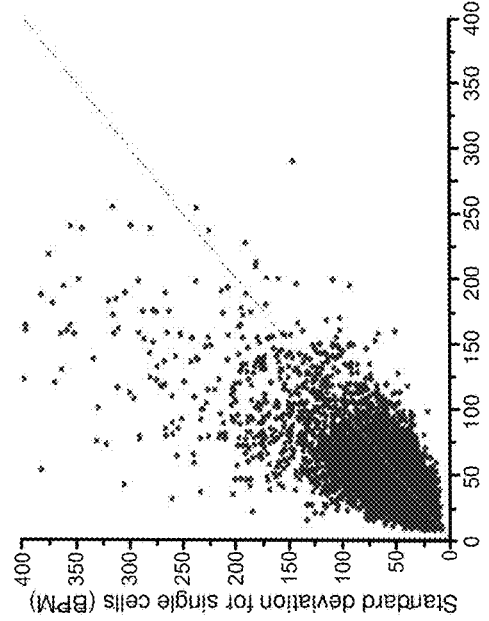
FIG. 19A
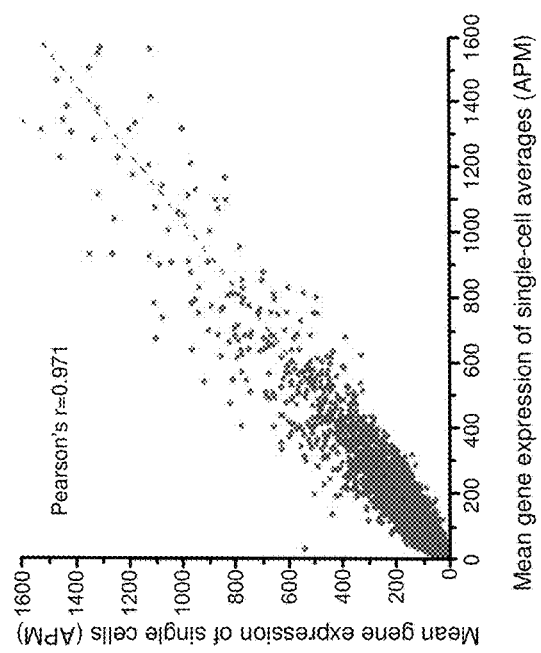
FIG. 19B
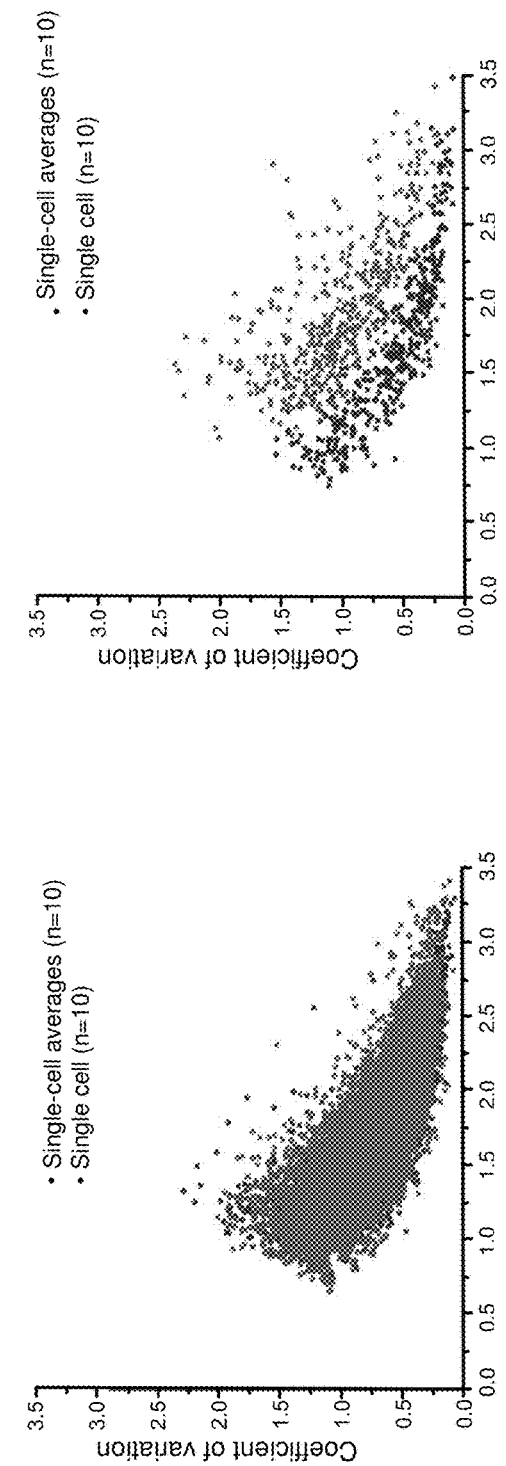
FIG. 19C
FIG. 19D

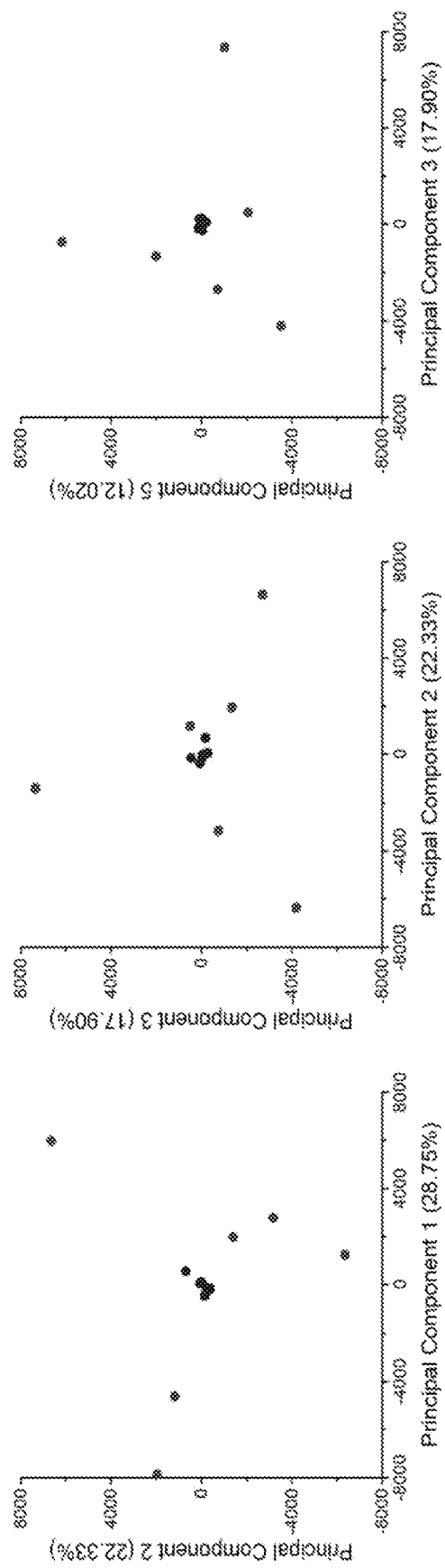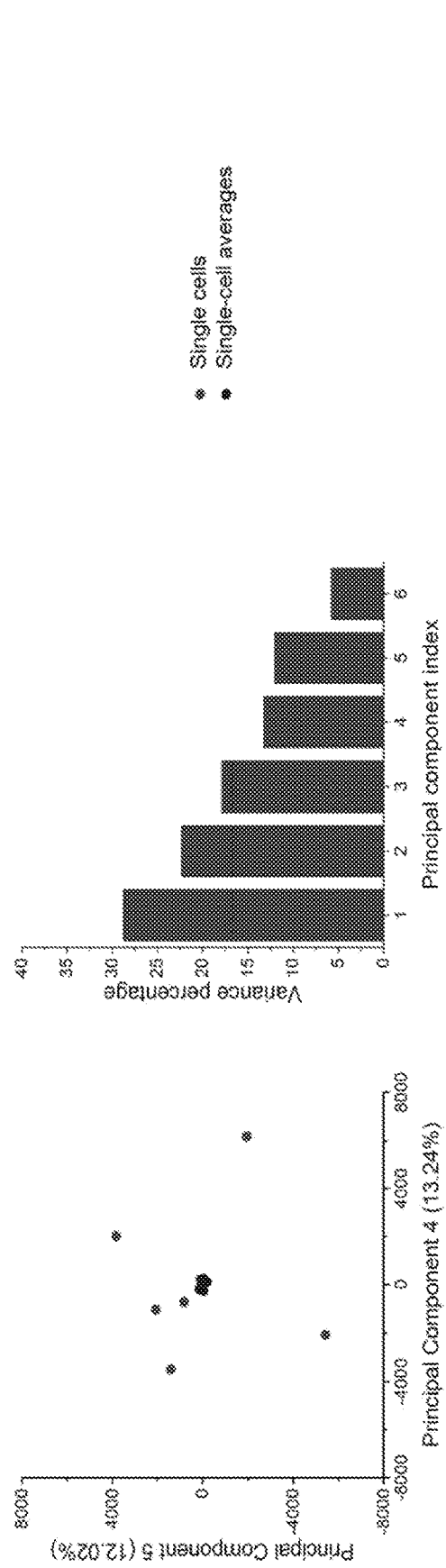
FIG. 21A FIG. 21B FIG. 21C FIG. 21D FIG. 21E

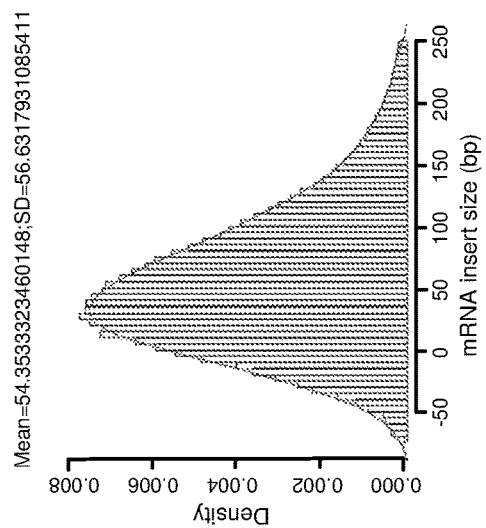
FIG. 24A
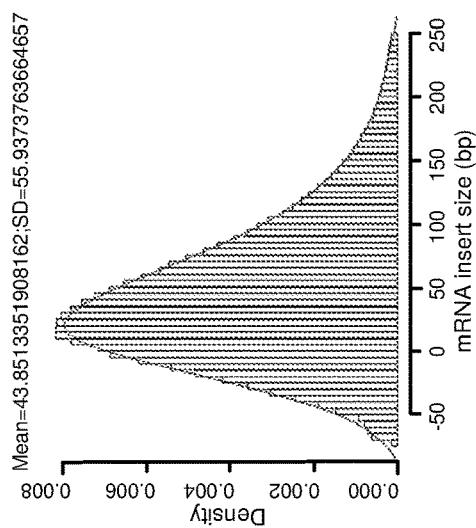
FIG. 24B
FIG. 24C
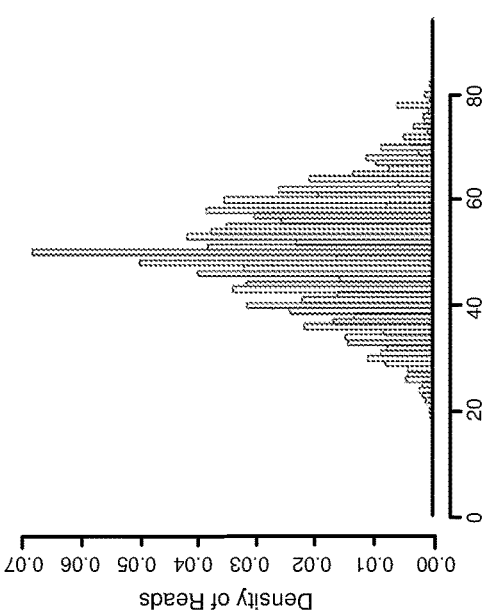
FIG. 24D
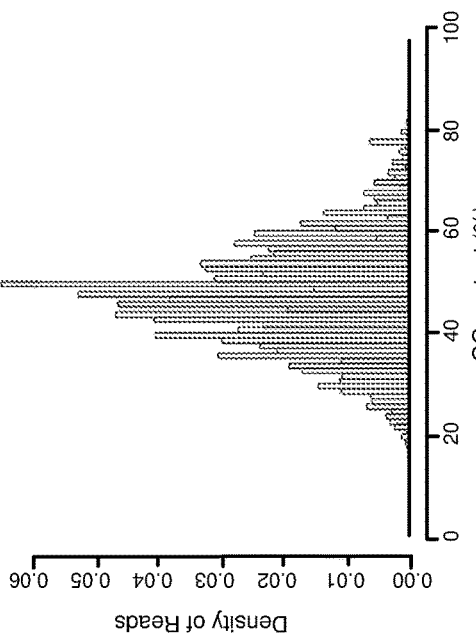
FIG. 24E
FIG. 24F

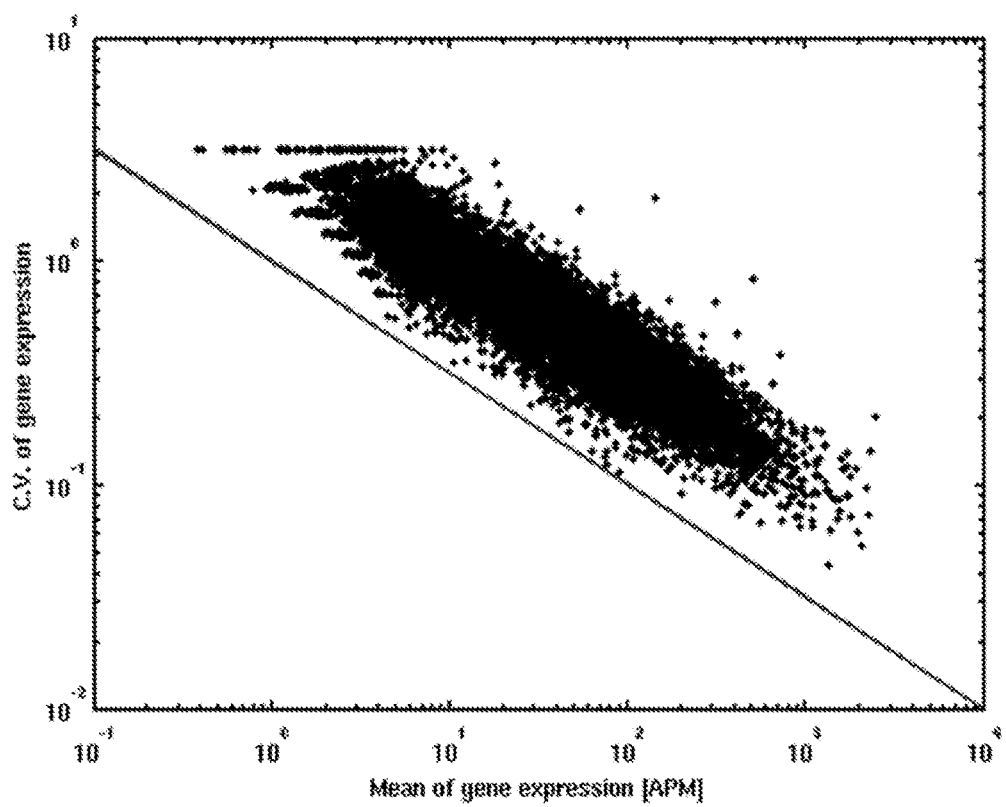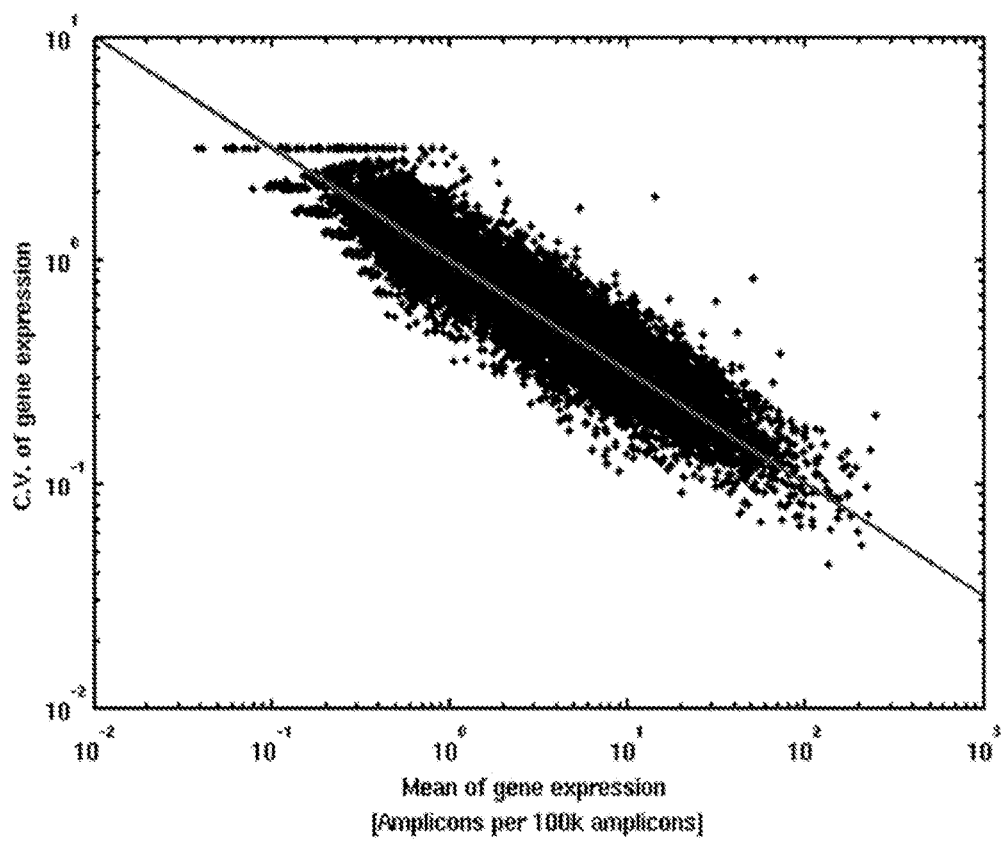
FIG. 26

METHODS OF WHOLE TRANSCRIPTOME AMPLIFICATION

CROSS-REFERENCE TO RELATED APPLICATIONS

This application is a national phase application under 35 U.S.C. § 371 that claims priority to International Application No. PCT/US2017/025472 filed Mar. 31, 2017, which claims priority to U.S. Provisional Patent Application Ser. No. 62/316,880, filed Apr. 1, 2016, all of which are incorporated herein by reference in their entirety.

STATEMENT REGARDING FEDERALLY SPONSORED RESEARCH OR DEVELOPMENT

This invention was made with government support under 1DP2EB020399-01 awarded by the NIH. The government has certain rights in the invention.

TECHNICAL FIELD

Embodiments of the disclosure include at least the fields of nucleic acid amplification, nucleic acid manipulation, genetics, medicine, and so forth. A field of embodiments of the disclosure concerns transcriptome amplification, including from one or more cells, for example.

BACKGROUND

The development of single-cell RNA sequencing has allowed the detection of gene expression at an anatomical resolution that is not accessible by bulk RNA-seq approaches (Tang et al., 2009; Ramskold et al., 2012; Hashimshony et al., 2012; Picelli et al., 2013; Wu et al., 2014; Islam et al., 2014; Streets et al., 2014; Jaitin et al., 2014; Fan et al., 2015; Chapman et al., 2015; Briese et al., 2015). While single-cell RNA-seq has been successfully used to identify new cell types in complex tissues, technical noise in these methods is still substantial and affects the ability to detect subtle biological differences (Marinov et al., 2014; Grun et al., 2014). Cells of the same type possess dynamic transcriptional variation that derives from intrinsic and extrinsic sources (Elowitz et al., 2002; Golding et al., 2005; Cai et al., 2006; Raj et al., 2008) and is challenging to identify using current methods. A sensitive and quantitative single-cell RNA-seq assay that could detect this transcriptional variation as well as subtle differences in gene expression between related cells (e.g. heterogeneous tumor cells) or cell states (e.g. cell fates in development) is highly desirable.

BRIEF SUMMARY

The present disclosure is directed to systems, methods, and compositions for preparation of a plurality of nucleic acids that may also include amplification and/or analysis of the plurality of nucleic acids. In particular embodiments, the plurality of nucleic acids is a full or partial transcriptome of one or more cells or cell-free materials, for example. The transcriptome may come from a single cell or multiple cells, such as two cells, three cells, four cells, five cells, ten cells, dozens of cells, hundreds of cells, thousands of cells, tens of thousands of cells, and so forth. In embodiments wherein the transcriptome comes from multiple cells, the multiple cells may or may not be of the same type, genotype, or phenotype. In cases wherein the nucleic acids are derived from multiple cells, the cells may or may not be from the same source or from the same tissue, for example. The cell may be of any type, but in certain embodiments, the cell is an immune cell, cancerous cell, a cell that is suspected to be cancerous, and so forth. Cell-free nucleic acid materials include nucleic acids that exist in blood or one or more other body fluids. In particular embodiments, the total RNA transcriptome is analyzed, and the methods are not limited to mRNA but also include non mRNA species such as long noncoding RNA or microRNA, for example.

Embodiments of the present disclosure relate in general to methods and compositions for preparing and amplifying transcriptomic sequences, such as the total RNA of a single cell, or optionally part or all of the RNA of multiple cells. The skilled artisan will recognize that methods of the disclosure allow a method for amplification of nucleic acids from the transcriptome, where the resultant product of the method is a plurality of amplicons (representing part or all of the respective transcriptome), and that at least in some cases the produced amplicons are then further amplified in either a linear or nonlinear manner (such as by PCR).

Embodiments of methods of the disclosure provide a significant improvement of presently used methods in the art. For example, the detection of genuine biological variation between single cells by amplification of total RNA from a single cell is greatly improved over methods in the art. Specific embodiments of methods provided herein introduce a method for whole gene body amplification. Whole gene body amplification enables the efficient detection of splice variants, noncoding RNA, and non-polyadenylated RNA, for example. Additional embodiments of methods provided herein introduce a "barcode" for each independently copied amplicon. This barcode allows for the removal of PCR bias thereby improving accuracy.

Methods are provided herein that can be used to perform the amplification of total RNA extracted from one single cell, although in some cases the total RNA may be extracted from more than one cell. Therefore, at least certain methods allow uniform whole transcriptome amplification for one single cell, which allow accurate detection of gene expression by standard high throughput sequencing platforms, in at least some embodiments.

In one embodiment, there is a method of producing full amplicons from one or more cells, comprising the steps of exposing nucleic acid from the one or more cells to a first plurality of primers and to a reverse transcriptase that comprises strand displacement activity, said exposing under conditions of a temperature range of about 8° C. to about 50° C., wherein the primers anneal to the nucleic acid and the primers are extended by the reverse transcriptase, wherein the primers in the first plurality are 40%-60% G-rich or 40%-60% C-rich, thereby producing a mixture comprising free primers, template RNA, and primer-annealed template RNA; exposing the primer-annealed RNA template to two or more annealing and cDNA synthesis steps, thereby producing a mixture of RNA template, unannealed primers, and first strand cDNA; exposing the mixture to conditions such that the unannealed primers and RNA template are digested; exposing the mixture to conditions such that the 3' end of the first strand cDNA becomes tailed with repeating C or G nucleotides; exposing the mixture to a second plurality of primers and a DNA polymerase, said exposing under conditions of a temperature range of about 48° C. to about 72° C., wherein the primers anneal to the nucleic acid and the primers are extended by the DNA polymerase, wherein the second plurality of primers comprise a 40%-60% G-rich or 40%-60% C-rich sequence and barcode region, thereby producing barcoded double-stranded cDNA amplicons. In a specific embodiment, the method further comprises the step of subjecting the barcoded double-stranded cDNA amplicons to amplification. In specific embodiments, the exposing the mixture step occurs at a temperature less than 60° C. In certain embodiments, the method provides for further obtaining the nucleic acid from the one or more cells, such as by lysis of the cell or cells and extraction of the nucleic acid therefrom. In specific embodiments, the nucleic acid comprises RNA.

In embodiments of the disclosure, certain primers may be utilized, including primers in a first or second plurality, at least. In specific embodiments, the primers in the first plurality, second plurality, or both comprise the following formula:

$$5'X_nY_mZ_p3',$$

wherein n is greater than 2 and X is 40%-60% G-rich or 40%-60% C-rich, wherein Y is any nucleotide and m is 5-8 nucleotides and wherein Z is a G when $X_n$ is G-rich or is C when $X_n$ is C-rich, wherein p is 2-20 nucleotides. In specific cases, m is 5 nucleotides; p is 3 nucleotides; p is 20 nucleotides; n is 20-40 nucleotides; n is 25-35 nucleotides; or n is 24-28 nucleotides. In a specific embodiment, the reverse transcriptase is SUPERSCRIPT® III. In certain cases, primer-template annealing and first-strand cDNA synthesis occur at a temperature range of about 8° C. to about 50° C. In certain embodiments wherein unannealed primer digestion is required, the reaction mixture is exposed to at least one of T4 DNA polymerase and/or Exonuclease I (or any enzyme that possess 3'→5' digestion activity and/or 5'→3' polymerization function) at a temperature range of about 30° C. to about 60° C. In specific embodiments, the reaction mixture is further exposed to Protease at a temperature range of about 30° C. to 40° C. In specific embodiments, RNA template digestion occurs in the presence of at least one of RNase H and/or RNase If at a temperature range of about 37° C. In certain cases, 3' end tailing of cDNA occurs in the presence of terminal deoxyribonucleic acid transferase (TdT) in the presence of excess C or G nucleotides at a temperature range of about 37° C. In some embodiments, following 3' end tailing, a second plurality of primers is added, wherein the second plurality of primers comprise an amplicon index of 5-8 random nucleotides. In certain cases, following addition of the second plurality of primers, the reaction mixture is heated to a temperature of about 95° C. In specific embodiments, the mixture is cooled a temperature of about 40-50° C. and a polymerase is introduced to the reaction mixture to perform second-strand cDNA synthesis. In certain embodiments, the polymerase used for second strand synthesis is DEEP VENT® (exo-). In certain cases, the conditions at which double-stranded amplicons are produced require thermal cycling to promote primer-template annealing and second-strand cDNA synthesis, wherein the temperatures cycled are about 48° C. and about 72° C. respectively, and the temperatures are cycled two or more times.

In particular embodiments, double stranded cDNA amplicons are subjected to amplification by PCR. In some embodiments, double stranded cDNA amplicons are exposed to a mixture of GAT-rich primers and a DNA polymerase. In certain embodiments, the DNA polymerase is DEEP VENT® (exo-) and/or Taq polymerase and/or other thermostable polymerases. In particular embodiments the double-stranded cDNA is melted at a temperature of at least 90° C. In certain cases, following the melting the mixture is cooled to a temperature below the melting temperature of the primer to promote annealing between single-stranded cDNA and primers, such as at a temperature range of about 55° C. to 60° C. In some cases, the temperature of the mixture is raised to at least 70° C. to promote extension of the primer-annealed nucleic acid templates. In specific embodiments, the temperatures for melting, annealing, and extending may be cycled in order to achieve nonlinear amplification of the double-stranded cDNA amplicons. Thermal cycling may comprise 10-30 cycles, in some cases. In some cases, the PCR-amplified cDNA may be further purified by exposure to at least one of Qiagen PCR cleanup kit or 0.9× AMPURE® beads. In specific embodiments, the PCR-amplified cDNA is subjected to sequencing or library construction methods.

In particular embodiments, the sequence of one or more of the cDNA amplicons is mapped to the genome. In specific embodiments, gene expression is quantified by calculating the number of unique amplicon indexes of one gene relative to the total number of all indexes of all genes.

In particular embodiments, one or more of the cDNA amplicons is assayed for a specific nucleotide or nucleotide sequence, such as one or more mutations in the amplicon that is representative of one or more corresponding mutations in the nucleic acid. In specific embodiments, the mutation is a disease-associated mutation. In specific embodiments, the one or more cells is from a fetus, an infant, a child, an adolescent, or an adult. In specific embodiments, the one or more cells may be fixed in a histological preparation. In some cases, though, the one or more cells are fresh or frozen. In certain cases, the one or more cells may be extracted from blood. In specific cases, the one or more cells may be obtained from an individual that has a medical condition or is suspected of having a medical condition, such as a genetic disease. In specific cases, the medical condition comprises cancer. In some cases, the medical condition comprises an immune response.

In one embodiment, there is a method of assaying the expression of one or more genes from an individual for identifying a medical condition in the individual or identifying a risk of the individual for having the medical condition, comprising the step of comparing part or all of a sequence of cDNA amplicons generated by methods of the disclosure from a sample from the individual to a standard. The standard may comprise RNA from normal cells from the individual, such as RNA from normal cells from one or more other individuals. In particular embodiments, the level of gene expression in cells in the sample from the individual is represented in the number of index-normalized sequence reads. In some cases, the comparing step comprises comparing the number of index-normalized sequence reads from cells in the sample from the individual to a standard. In specific embodiments, at least some of the index-normalized sequence reads comprise one or more particular genes. In certain embodiments, the comparing step comprises assaying for the presence or absence of one or more particular nucleotides in the sequence reads of the sample compared to the standard. In other embodiments, the comparing step comprises assaying for the presence of one or more particular gene fusion products in sequence reads of the sample compared to the standard.

In one embodiment, there is a method of amplifying RNA from one or more cells, comprising the steps of: exposing RNA from the one or more cells to a first plurality of primers and to at least one reverse transcriptase to produce a reaction mixture; subjecting said reaction mixture to conditions in that allow annealing of the primers to the RNA and first-strand cDNA synthesis to produce extended DNA strands;

digesting unannealed primers; inactivating enzymes in the reaction mixture; digesting RNA in the reaction mixture; tailing the 3' ends of the extended DNA strands; generating second-strand cDNA synthesis using a second plurality of primers and at least one DNA polymerase under suitable conditions to produce double-stranded full amplicons, wherein the primers in the first plurality, second plurality, or both comprise the following formula: 5' $X_nY_mZ_p$ 3', wherein n is greater than 2 and X is 40%-60% G-rich or 40%-60% C-rich, wherein Y is any nucleotide and m is 5-8 nucleotides and wherein Z is a T or a G when X is G-rich or Z is a C when X is C-rich, wherein p is 2-20 nucleotides. In specific embodiments, m is 5 nucleotides and/or p is 3 nucleotides and/or p is 20 nucleotides and/or n is 20-40 nucleotides and/or n is 25-35 nucleotides and/or n is 24-28 nucleotides.

In particular embodiments, first-strand cDNA synthesis uses the reverse transcriptase SUPERSCRIPT® II, SUPERSCRIPT® III or SUPERSCRIPT® IV. In at least some cases, annealing of the first plurality of primers to the RNA and/or annealing of the second plurality of primers to the DNA occurs in the range of 0-10° C. The first-strand cDNA synthesis may occur at least at 30-55° C. In at least some cases, the unannealed primers are digested with at least one of a DNA polymerase and/or exonuclease possessing 3' to 5' exonuclease activity. The DNA polymerase and/or exonuclease possessing 3' to 5' exonuclease activity may be at least one of T4 DNA Polymerase and/or Exonuclease I. Digesting the primers may occur at a temperature in the range of 60°-65° C. In specific embodiments, inactivating the enzymes occurs at a temperature in the range of 72-95° C. In certain embodiments, digesting the RNA occurs with at least one ribonuclease, such as at least one of RNase H and/or RNase If. Digesting of the RNA may occur at a temperature in the range of 30-50° C. In certain cases, tailing the 3' ends of the extended DNA strands occurs with at least one terminal deoxyribonucleotide transferase, such as TdT terminal transferase. The tailing of the 3' ends of the extended DNA strands may utilize deoxycytosine triphosphate or deoxyguanosine triphosphate, for example. In cases when the first plurality of primers are G-rich, deoxycytosine triphosphate may be utilized for tailing. In cases when the first plurality of primers are C-rich, deoxyguanosine triphosphate may be utilized for tailing. In specific aspects, the tailing step occurs at a range of temperature of 10-45° C. The generating step may occur at a temperature in the range of 10-45° C. and/or may utilize DEEP VENT® (exo-) DNA polymerase and/or Taq polymerase. The generating step may comprise annealing of the second plurality of primers to the 3' end of amplicons at a temperature in the range of 30-55° C. In certain cases, the condition at which DNA elongation takes place to produce double stranded DNA is 72° C.

In particular embodiments, the primers in the second plurality of primers comprise an amplicon index to control for polymerase chain reaction efficiency bias. The double stranded full amplicons may be further amplified by linear or nonlinear methods. In specific embodiments, at least some of the amplified amplicons are sequenced. The sequence may be analyzed for one or more of an insertion, deletion, single nucleotide variations (SNVs), splice variants, gene fusion products, and the presence or absence of individual transcripts relative to a control sample.

In particular embodiments the one or more cells from which the RNA is obtained are isolated from an individual. The one or more cells may be circulating tumor cells. In some cases, the one or more cells are peripheral blood mononuclear cells (PBMCs) The one or more of the amplified amplicons is analyzed for one or more of cancer mutations, gene fusion products, splice variants, the expression of oncogenes, the loss of expression of tumor suppressors, and the expression of tumor-specific antigens. In cases when expression of oncogenes is analyzed, the oncogene may be BAG1, Bcl-2, CTNNB1, BRAF, FOS, JUN, EGFR, ERBB2, ETV6-NTRK3 gene fusion, Gankyrin, GT198, MDM2, MIG7, MYC, SRC, RAS, SKI, TCTP, ABL, CBL, ROS1, AKT, BAX, FKHR, CDK2, CDK4, CCND1, CCNE1, PIK3CA, HPV-E7, HPV-E6, AURKA, miR-155, FAS, GLI, SHH, SMO, NOTCH, ILK, RAR, SOX, WNT1, TAL1, MLL, HOXA1, MITF, EVI1, BCL6, and/or HOXA9. In cases wherein one or more tumor suppressors are analyzed, the tumor suppressor may be APC, BRCA1, BRCA2, CDKN1B, CDKN1C, DLD/NP1, HEPACAM, INK4, miR-145, p15, p16, p53, p5'7, p63, p'73, PTEN, Rb, SDHA, SDHB, SDHC, SDHD, SFRP1, TCF21, TIG1, TP53, TSC1/TSC2, and VHL, BCL2, INPP4B, LKB1, ARF, ATM/ATR, CHK1, CHK2, DNA-PK, FANCs, HIPK2, NBS1, WT1, MUTYH, BLM, RECQL4, WRN, MLH1, MSH2, MSH6, PMS2, XPA, XPC, XPD, FBXW7, PTCH1, SUFU, EXT1, EXT2, NF1, NF2, BMPR1A, SMAD2, SMAD3, SMAD4, TGFBR1, MEN1, APC, AXIN, CTNNA1, CDH1, WNT5A, GPC3, HRPT2, and/or HPC1. In cases wherein one or more tumor-specific antigens are analyzed, the tumor-specific antigens may be EphA2, HER2, GD2, Glypican-3, 5T4, 8H9, αvβ6 integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CS1, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD3, HLA-AI, HLA-A2, IL11Ra, IL13Ra2, KDR, Lambda, Lewis-Y, MCSP, Mesothelin, Muc1, Muc16, NCAM, NKG2D ligands, NY-ESO-1, PRAME, PSCA, PSC1, PSMA, ROR1, Sp17, SURVIVIN, TAG72, TEM1, TEM8, carcinoembryonic antigen, HMW-MAA, VEGF receptors, MAGE-A1, MAGE-A3, MAGE-A4, CT83, SSX2, XIAP, cIAP1, cIAP2, NAIP, and/or Livin.

In some cases, one or more of the amplified amplicons may be analyzed for the expression of tumor-specific T-cell receptors (TCRs), and the TCR may target MART-1, gp100, NY-ESO-1 and/or one or more surface antigens. One or more of the amplified amplicons may be analyzed for the presence of one or more immune cell activation markers, such as CD3, CD8, CD25, GZMB, CD45RO, PTPRC, and/or IFNG.

In some cases, the one or more cells may be isolated from an individual's neoplasia. In specific embodiments, more than one cell is analyzed to determine tumor heterogeneity. In at least some cases, one or more of the cells are collected pre- and post-therapy, such as at least one of chemotherapy, immunotherapy, hormone therapy, radiation, and/or surgery.

In cases wherein the cells are from a tumor, the tumor may be acute lymphoblastic leukemia, acute myelogenous leukemia, chronic lymphocytic leukemia, chronic myelogenous leukemia, acute monocytic leukemia, Hodgkin's lymphoma, non-Hodgkin's lymphoma, breast, prostate, lung, and colon cancers or epithelial cancers/carcinomas such as breast cancer, colon cancer, prostate cancer, head and neck cancer, skin cancer, cancers of the genito-urinary tract, e.g. ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivary glands and/or cancer of the thyroid gland.

The one or more cells may be from a developing fetus. In some cases, one or more of the amplified amplicons of one or more cells are analyzed for congenital disorders or known phenotypical consequences. The congenital disorder or known phenotypical consequence may be beta-thalassaemia, Down's syndrome, cystic fibrosis, sickle cell disease, tay-sachs disease, fragile X syndrome, spinal muscular atrophy, haemoglobinopathies, alpha-thalassemia, X-linked disorders, spina bifida, anencephaly, congenital heart defects, obesity, diabetes, cancer, fetal gender, fetal RHD, fetal HLA haplotype, or paternally derived mutations.

In particular embodiments, one or more cells are analyzed to trace transcriptomic changes in relation to cellular lineage and differentiation. The one or more cells may be stem cells, and the stem cells may be subjected to conditions to induce differentiation. The one or more stem cells may be sampled at different times. In specific embodiments, one or more of the amplified amplicons of one or more cells is analyzed to determine transcriptomic heterogeneity during stem cell differentiation. In specific cases, the one or more cells are cells that have been modified to express Cas9 and one or more single guide RNAs (sgRNAs). In some embodiments, one or more of the amplified amplicons of one or more cells is analyzed for the presence of one or more of an insertion, deletion, single nucleotide variations (SNVs), and the presence of absence of target(s) of the sgRNA(s).

In certain cases, the one or more cells are prokaryotic cells, such as a bacterium. In specific cases, the cells are collected from an individual with an infection of said bacterium. The individual may be administered antibiotic therapy, such as based on the outcome of a method of the disclosure. In particular cases, one or more of the amplified amplicons of the bacterium is analyzed during antibiotic therapy.

One or more of the amplified amplicons may be analyzed for the emergence of one or more of mutations or insertions, or deletions associated with antibiotic resistance.

In particular embodiments, the RNA is the total RNA transcriptome.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 1A-1E. FIG. 1A illustrates a schematic overview of the disclosed method for whole transcriptome amplification. 'PolyC tailing' refers to the tailing reaction by terminal transferase. dT20 refers to 20 consecutive thymine bases. Red indicates common MALBAC primer sequences; blue indicates three consecutive G or T ends; green indicates synthesized cDNAs. (FIG. 1B) shows a plot comparing read coverage along the gene body for disclosed invented method (MATQ-seq) to existing methods. Shaded area, s.d. of the coverage. (FIG. 1C) provides a comparison of the number of detected genes between the disclosed method (red) compared to an existing method (blue) in single HEK293T cells. RPM, reads per million mapped reads. ***, $P=1.6\times10^{-6}$ for $0<RPM\leq10$ and $P=2.1\times10^{-5}$ for $10<RPM\leq100$ (two sample t-test). n.s., not significant (P=0.4). Lower and upper hinges correspond to 25th and 75th percentiles, upper and lower whiskers represent the standard deviations, squares correspond to the means, and dots denote single cell data. (FIG. 1D) shows the percentage of genes detected repeatedly between pairs of single cells in disclosed method (red) and an existing method (blue). Error bar: s.e.m. (FIG. 1E) provides a comparison of pairwise-gene-expression-ratios for single cells in the disclosed method (red) and existing method (blue). Error bars, s.d.

FIGS. 2A-2E provide principle component analysis of gene expression measurements of single HEK293T cells (n=38) which shows that single-cell averages (n=10) cluster near the mean of single cells. Each plot shows two consecutive principal components. The percentage of variation explained by each component is given in the axis labels. (FIG. 2F) shows the variance percentage of each principal component.

FIGS. 3A-3E. FIG. 3A shows a plot comparing the mean expression levels (expressed as APM or amplicons per one million total amplicons) are highly correlated between single cells and single-cell averages. Dashed line represents y=x. (FIG. 3B) shows a plot comparing the standard deviation of gene expression in single cells compared with that in single-cell averages. Dashed line represents y=x. (FIG. 3C) provides a plot of skewness of gene expression in single cells and single-cell averages. (FIG. 3D) shows that Fano factors are correlated between two sets of single cells. (FIG. 3E) shows that Fano factors are not correlated between single cells and single-cell averages.

FIGS. 4A-4C plot the comparison of (FIG. 4A) lncRNA, (FIG. 4B) miRNA, and (FIG. 4C) protein coding genes detected by SUPeR-seq, Smart-seq2, and MATQ-seq in single HEK293T cells (n=5 for each assay). SUPeR-seq data was downloaded from GSE53386 (Fan, et al., 2015). SMART-seq2 data was downloaded from GSE49321(2). With different sequencing modes in different studies, we require the similar number of reads with mapping score=50 in Tophat for equal footing comparison. Downsampling was performed to reach the level of 3.5-4 million fragments. Both SUPeR-seq and SMART-seq2 data were reanalyzed using the same pipeline as the analysis for MATQ-seq data. miRNA detection likely comes from its pre-mature form since small amplicons generated from miRNA molecules cannot be efficiently amplified. Lower and upper hinges correspond to 25th and 75th percentiles, upper and lower whiskers represent the standard deviation, square correspond to mean, and each dot in the plot represents one cell. Gencode (GRCh37.p13) was used for gene annotation. The Ensembl BioMart was used to classify the category of every annotated Ensembl gene.

FIGS. 8A-8D provide histograms of pairwise-gene-expression-ratio for different assays. The x-axis indicates the ratio of gene expression in log 10 scale, and the y-axis indicates the number of genes. Error bar: standard deviation. (FIG. 8A) 4 single cell gene expression data are downloaded and analyzed for SMART-seq method (Picelli, et al., 2013). (FIG. 8B) 7 gene expression data are downloaded and analyzed for SMART-seq2 (Picelli, et al., 2013). (FIG. 8C) 7 single cell data are downloaded and analyzed for SUPeR-seq (Fan, et al., 2015). (FIG. 8D) 99 cells are downloaded and analyzed for single cell RNA-seq using unique molecular identifier (STRT-seq) (Islam, et al., 2014).

FIGS. 10A-10C. FIGS. 10A-10B show the Principal Component Analyses of single cells and single-cell averages with gene expression quantified by reads (RPM). Reads mapped to exon regions are used. Importantly, this shows single-cell averages deviate from the center. FIG. 10C shows the variance percentage for each principal component. The first principal component contributes ~87% of the total variance and the first two components contributes ~99%. This suggests that systematic PCR amplification noise dominates the variance. In contrast, the amplicon based gene expression quantification shows a much smoother decrease of the principal component variance FIG. 6.

FIG. 13A provides the coefficient of variation (CV) for all genes of HEK293T samples. To avoid inefficient sampling of technical noises, F-tests were performed only for the genes with detected expression in all single-cell averages. Exon-based quantifications are used for the analyses. It is worth noting that for the vast majority of genes, single cell CV distribution overlaps with that of single-cell averages. FIG. 13B provides the CV of genes with FDR<0.1 from F-test performed on the variance between single cells and single-cell averages. To avoid inefficient sampling of technical noises, F-tests were performed only for the genes with detected expression in all single-cell averages. Exon-based quantifications are used for the analyses. It is worth noting that for the vast majority of genes, single cell CV distribution overlaps with that of single-cell averages.

FIGS. 14A-14F. FIGS. 14A-14E shows the Principal Component Analyses of single cells and single-cell averages based on amplicon mapped to intronic regions. Consistent with the exon-based PCA, the single-cell averages are still clustered when the percentage of the principal component becomes small. FIG. 14F shows the distribution of the variance percentage of the principal components shows a smooth decrease of variance.

FIG. 15A provides the scatter plot to compare the mean expression levels of genes of single cell samples with that of the single-cell averages. (FIG. 15B) The scatter plot to compare the standard deviations of gene expression of single cells with that of the single-cell averages. The dash line represents y=x. (FIG. 15C) The skewness of gene expression in single cells.

(FIGS. 16A-16B) Two genes with skewness greater than 3 and they are considered to be "bursty" genes. For gene FAM13A, there is one cell with the expression level as large as ~170 APM while the majority of cells are less than 50 APM. For gene TBL1Y, there are two cells with gene expression level above 700 APM while the majority of 36 cells are less than 200 APM. (FIGS. 16C-16D) Two genes with skewness less than 0.5. There are no significant outliers in gene expression for these two genes.

(FIG. 17A) Scatter plot of the mean gene expression levels of single cells between different clones. The Pearson's correlation coefficient of 0.947 shows that the averaged transcriptome profile of these two clones are quite similar. (FIG. 17B) The clonal separation captured by PCA plot between clone-1 (black) and clone-2 (blue).

(FIGS. 18A-18E) Principal Component Analyses of single cells and single-cell averages based on amplicon mapped to exonic regions (HEK293T clone-2, 10 single cells and 10 single cell averages). Consistent with the observations in the first clone, the single-cell averages are still well clustered when the percentage of the principal component becomes small. (FIG. 18F) The distribution of the variance percentage of the principal components shows a smooth decrease of variance.

FIGS. 19A-19D provide the gene expression analyses for the second HEK293T clone. 10 single cells and 10 single-cell averages were sequenced. The quantification of gene expression was exon-based. (FIG. 19A) The scatter plot to compare the mean expression levels of genes of single cell samples with that of the single-cell averages. (FIG. 19B) The scatter plot to compare the standard deviations of gene expression of single cells with that of the single-cell averages. The dash line represents y=x. (FIG. 19C) The coefficient of variation (CV) genes with FDR>0.1 from F-test performed on the variance between single cells and single-cell averages (FIG. 19D) The CV of genes with FDR<0.1 from F-test performed on the variance between single cells and single-cell averages. Total 292 genes were identified.

FIGS. 21A-21E show the Principal Component Analyses of MCF10A samples. The inventors sequenced 6 single cells and 6 single-cell averages. The intron-based quantification was used for the analyses. The variation percentage of 6 principal components evenly decreases. Single-cell averages cluster closely while individual single cells spread out. 425 genes with FDR<0.05 are identified with large transcriptional variations in single cells comparing to the single-cell averages.

FIGS. 24A-24F give the Reads statistics of MATQ-seq. The gene coverage for two randomly selected single cells (FIGS. 24A and 24D); the GC % statistics of mapped reads (FIGS. 24B and 24E); the insert size (FIGS. 24C and 24F). The fragment size for library construction should be the insert size plus the total length of paired-end reads (85×2 bases), so on average the fragment size after shearing is ~200 bases. The above data were generated using RSeQC package (v2.6.3).

FIG. 26 shows the coefficient of variation over mean using a different normalization factor. For the figure on the upper panel, we used amplicons per million amplicons (APM) as the expression unit. The red line represents the relation between CV and mean for Poisson distribution. For the figure on the lower panel, we renormalized the gene expression by 100 k amplicons instead of 1 million amplicons as in APM. Using this normalization, the CV versus the mean overlaps with the Poisson line in the lower panel, indicating a reasonable adjustment of renormalization. It is worth noting that CV values do not vary with different renormalizations.

DETAILED DESCRIPTION OF THE INVENTION

Figure 2A:
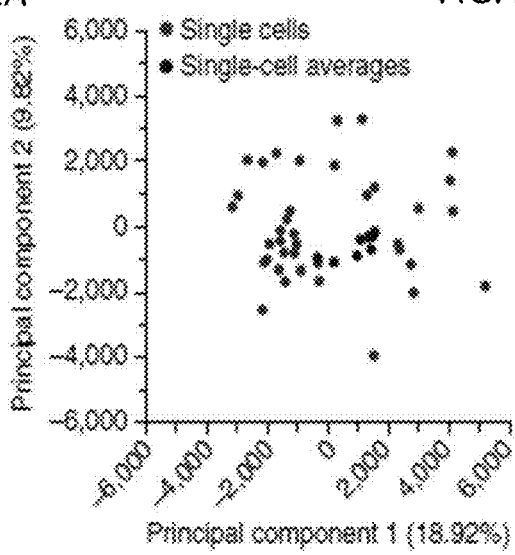
FIGS. 2A-2F.
Figure 2B:
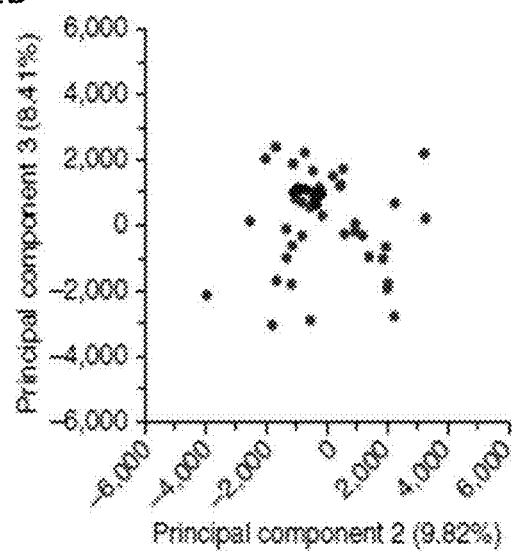
Figure 2C:
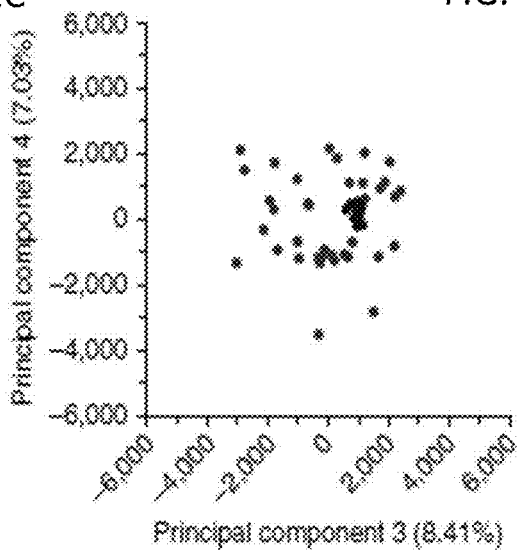
Figure 2D:
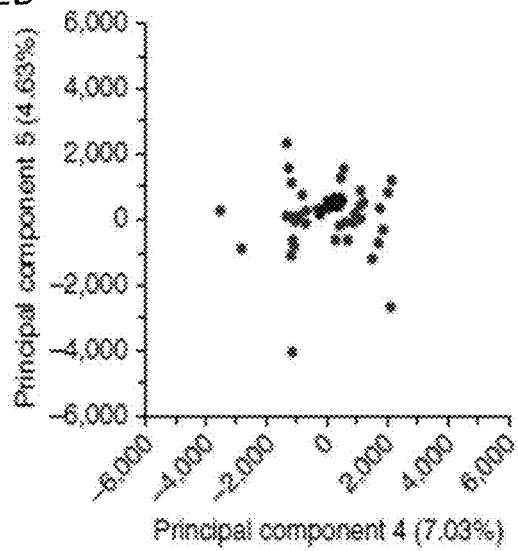
Figure 2E:
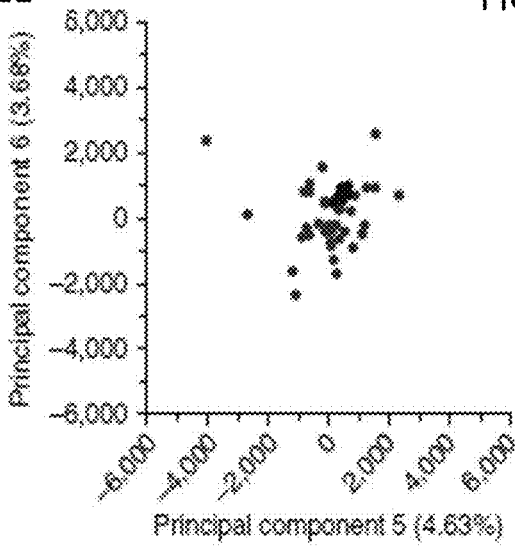

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "amplicon" refers to DNA fragments with specific adaptor sequences that allow the amplification by PCR method or others.

I. General Embodiments

Embodiments of the disclosure provide amplification methods useful for amplifying part of all of the RNA from one or more cells. Embodiments of the disclosure demonstrate methods for the accurate and sensitive generation of double-stranded DNA (cDNA) from the total RNA of one or more cells. Double-stranded cDNA produced according to the disclosed amplification method is suitable for further amplification, whether or not by nonlinear means, for example by PCR, as well as methods of nucleic acid sequencing.

Embodiments of the disclosure provide a sensitive sequencing protocol that utilizes MATQ-seq, for Multiple Annealing and dC-Tailing based Quantitative single-cell RNA-seq. MATQ-seq can identify transcriptional variation among cells of the same population, and has been shown to systematically characterize technical noise in order to demonstrate that the detected transcriptional variation is biologically genuine. In contrast to existing methods such as SMART (Switching Mechanism At 5'-end of RNA Template) chemistry—based methods, MATQ-seq provides whole gene body coverage and the detection of total RNA, including noncoding and non-polyadenylated RNA. In addition, MATQ-seq removes PCR bias using a molecular barcoding strategy.

FIG. 1 shows a schematic overview of an embodiment of a method disclosed herein. According to certain aspects of the disclosure, RNA from a single cell or multiple cells is obtained. In specific cases, the individual performing the method obtains the RNA from the sample, whereas in other cases the RNA is provided by an entity that is not performing the method. The RNA is placed (or provided) in a reaction vessel and the RNA is exposed to at least one reverse transcriptase in the presence of a first plurality of primers to produce a reaction mixture. In specific embodiments, the primers in the first plurality are 40%-60% G-rich or 40%-60% C-rich. In specific embodiments, the primers comprise the following formula: 5' $X_n Y_m Z_p$ 3', wherein n is greater than 2 and X is 40%-60% G-rich or 40%-60% C-rich, wherein Y is any nucleotide and m is 5-8 nucleotides and wherein Z is a T or a G when X is G-rich or Z is a C when X is C-rich, wherein p is 2-20 nucleotides. In any event, the first plurality of primers are designed to avoid crosstalk among them.

In a particular embodiment, there is multiple annealing of the primers to the nucleic acid. Upon exposure of the primers to the nucleic acid, this generates a mixture comprising primer-annealed nucleic acid templates. According to one aspect, the reaction mixture is then subjected to conditions which promote primer-template annealing. This involves lowering the temperature of the mixture to a temperature that allows random nucleotides at the 3' end of the first primer to anneal to the RNA to form hybrid duplexes. In specific cases, the temperature may be as low as 0° C. and may be as high as 37° C. After the hybrid duplexes form, one or more reverse transcriptases present in the reaction mixture extends the cDNA strand from the 3' end of the first primer during an incubation period. The process of hybrid duplex formation and cDNA extension is repeated at least 2 times, although it may occur 3, 4, 5, 6, 7, 8, 9, 10, 11, 12, 13, 14, 15, 16, 17, 18, 19, or 20 or more times. In the repetition of this step, there is no subjecting of the reaction to melting temperatures. Following first-strand cDNA synthesis by reverse transcriptase, the reaction mixture is subjected to conditions wherein unannealed primers and template RNA are digested and enzymes present in the reaction are made inactive. In particular cases, the primers are digested prior to digestion of the template RNA. The digestion of the primers may occur by any manner, but in specific embodiments it occurs with a nuclease. In embodiments of the disclosure, methods are provided that can efficiently remove preexisting primers to allow efficient tailing of the first-strand cDNAs. Without efficient digestion of primers, the tailing of residual primers out-competes the tailing of semi amplicons and leads to the failure of amplification in the following step. Thus, in certain aspects one can use T4 DNA polymerase or other polymerases with exonuclease activities at low temperature below (30° C. or below) and Exonuclease I or other exonucleases that only digest unannealed primers. The enzymes can be heat-inactivated.

The digestion of the RNA may occur by any manner, but in specific embodiments it occurs with a ribonuclease. In embodiments of the disclosure, methods are provided that can efficiently remove preexisting template RNA. One can expose the reaction mixture to at least one of RNase H and/or RNase If. In certain embodiments, RNases can be inactivated by enzymatic proteolysis. The inactivation of the enzymes in the reaction mixture may occur by any manner, but in specific embodiments it occurs with a protease.

Next, the reaction mixture is exposed to conditions which promote 3' end tailing to enhance stability and complementarity with the second plurality of primers. The tailing of the 3' end may occur by any method, but in specific embodiments it occurs by terminal transferase. The tailing preferably is with a single nucleotide and in specific embodiments the polynucleotide is a C or a G, depending on the sequence of the primers in the first plurality. When the primers in the first plurality are G-rich, the polytailing is with a C, and when the primers in the first plurality are C-rich, the polytailing is with a G. That is, in specific embodiments, 3' end tailing can be conducted with concentrated C base or G base in the presence of terminal deoxynucleotidyl transferase, wherein the base used for tailing will be the complimentary to the first plurality of primers (e.g. concentrated C will be used when the first plurality of primers is G-rich). The length of the tail may be of any length but in particular may be in the range of 1-3000 bases.

Following 3' end tailing, the reaction mixture is exposed to a second plurality of primers which comprise a barcode, as well as at least one DNA polymerase. In particular embodiments, the barcode allows for assigning the reads back to the original amplicons. In cases wherein the first plurality of primers comprise a G-rich region and the 3' DNA ends are polytailed with C's, the second plurality of primers comprise a G-rich region suitable for binding to the poly-C tail. In cases wherein the first plurality of primers comprise a C-rich region and the 3' DNA ends are polytailed with G's, the second plurality of primers comprise a C-rich region suitable for binding to the poly-G tail.

In specific cases, the second plurality of primers may have the 5' $X_n Y_m Z_p$ 3' sequence motif, wherein n is greater than 2 and X is 40%-60% G-rich or 40%-60% C-rich, wherein Y is any nucleotide and m is 5-8 nucleotides and wherein Z is a T or a G when X is G-rich or Z is a C when X is C-rich, wherein p is 2-20 nucleotides. In any case, the second plurality of primers are designed to avoid crosstalk among them.

The reaction mixture is then subjected to conditions which promote hybridization between barcoded primer and single-stranded cDNA template. After the hybrid duplexes form, one or more polymerases present in the reaction mixture extend the second cDNA strand from the 3' end of the first primer during an incubation period.

Thus, embodiments of the invention include methods of linearly amplifying total RNA from one or more cells. The method in some aspects begins with a provided nucleic acid sample, although in some cases the nucleic acid must be obtained from the cell(s), such as by routine methods. When amplifying the transcriptome, the totality of nucleic acid may be subjected to DNase prior to reverse transcription of the total RNA. Nucleic acid from one or more cells is exposed to a first plurality of primers and a reverse transcriptase. In such a step, the primers anneal to the nucleic acid and the primers are extended by the reverse transcriptase.

II. Barcodes

PCR amplification bias is a significant challenge in RNA sequencing as small differences in amplification efficiency can lead to significant artificial signals in the data. To address this issue, one can introduce random "barcodes" (random DNA sequence with variable length (for example NNNNNN, where N represents mixture of four nucleotides) into the primers, which will index each unique cDNA and its corresponding double-stranded cDNA product (FIG. 1). By indexing each of the reads with barcodes, one can differentiate high copy genes (highly expressed genes) from cDNAs with high amplification efficiency (e.g. a high copy gene with many unique barcodes compared to a high copy gene with only one barcode). Such an application significantly improves the accuracy of sequencing data and captures true biologically meaningful information. The disclosed methods provide a solution to normalize gene expression from sequencing data using said barcodes.

III. Exemplary Applications of Methods of the Disclosure

Methods of the disclosure may be utilized in research, clinical, and/or other applications. In particular embodiments, methods of the disclosure are utilized in diagnostics and/or prognostics and/or monitoring of one or more therapies for an individual, for example. In some cases, the party preparing the amplicons may or may not be the party or parties performing the amplification of the amplicons and also may or may not be the party or parties performing analysis of the amplicons, whether amplified or not. A party applying information from the analysis of the amplified amplicons may or may not be the same party that performed the method of preparing the amplicons and/or amplifying them.

In one example of an application of one or more methods of the disclosure, the method is utilized for assaying for one or more variations in content or expression level of one or more nucleic acids from an individual; the variation may or may not be in relation to a known standard, for example, such as a corresponding wild-type sequence of a particular nucleic acid. The variation in content may comprise one or more nucleotide differences compared to wild-type, such as a substitution, deletion, inversion, and so forth. The variation in expression may comprise upregulation or downregulation compared to normal expression levels of a particular known or determined standard. The standard may comprise the content of normal nucleic acid content or expression level in cells known to be normal in genotype and/or phenotype.

In specific embodiments, one or more of the amplified amplicons is analyzed for one or more of cancer mutations, gene fusion products, splice variants, the expression of oncogenes, the loss of expression of tumor suppressors, the expression of tumor-specific antigens, and/or the expression of all the expressed genes.

In specific cases, the nucleic acid being assayed for is obtained from a sample from an individual that has a medical condition or is suspected of having a medical condition or is at risk for having a medical condition or is undergoing therapy for a medical condition. The sample may be of any kind so long as nucleic acid may be obtained directly or indirectly from one or more cells from the sample. In particular embodiments, the nucleic acid is obtained from one or more cells from a sample from the individual. The sample may be blood, tissue, hair, biopsy, urine, nipple aspirate, amniotic fluid, cheek scrapings, fecal matter, or embryos.

An appropriate sample from the individual is obtained, and the methods of the disclosure may be performed directly or indirectly by the individual that obtained the sample or the methods may be performed by another party or parties.

In some cases, in order to obtain sufficient nucleic acid for testing, a blood volume of at least 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; CD4+ cells; CD8+ cells; immune cells; T cells, NK cells, or the like). The peripheral blood cells can also be selectively depleted of a particular cell type (e.g., mononuclear cells; red blood cells; CD4+ cells; CD8+ cells; immune cells; T cells, NK cells, or the like).

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular immune cells. In some cases, the starting material can be a sample containing nucleic acids, from any organism, from which genetic material can be obtained. In some cases, a sample is a fluid, e.g., blood, saliva, lymph, or urine.

In some cases, a sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. In some cases, the subject can be receiving therapy for treatment of a condition. In some cases, the therapy can be for treating cancer. In some cases, the therapy can be immunotherapy. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

A. Genetic Testing

In particular applications, one or more particular nucleic acid sequences are desired to be known in a sample from an individual. The individual may be of any age. The individual may be subjected to routine testing or may have a particular desire or medical reason for being tested. The individual may be suspected of having a particular medical condition, such as from having one or more symptoms associated with the medical condition and/or having a personal or family history associated with the medical condition. The individual may be at risk for having a medical condition, such as having a family history with the medical condition or having one or more known risk factors for the medical condition, such as high cholesterol for heart disease, being a smoker for a variety of medical conditions, having high blood pressure for heart disease or stroke, having a genetic marker associated with the medical condition, and so forth.

In specific cases, the individual is a fetus and the fetus may or may not be suspected of having a particular nucleic acid sequence or nucleic acid expression variance compared to wild type, such sequence content or expression variance associated with a medical condition. In some cases, the fetus is at risk for a particular medical condition because of family history or environmental risk (i.e., radiation) or high-age pregnancy, for example, although the fetus may be needed to be tested for routine purposes. In such cases wherein a particular sequence(s) content or expression level is desired to be known from a fetus, a sample is taken that comprises one or more fetal cells. The sample may be a biopsy from the fetus, although in particular cases the sample is amniotic fluid or maternal blood or embryos at early stage of development.

In one aspect of the disclosure, amniotic fluid from a pregnant mother is obtained and one or more fetal cells are isolated therefrom. The fetal cell isolation may occur by routine methods in the art, such as by utilizing a marker on the surface of the fetal cell to distinguish the fetal cell(s) from the maternal cell(s). Three different types of fetal cells could exist in maternal circulation: trophoblasts, leukocytes and fetal erythrocytes (nucleated red blood cells). The most promising cell for enrichment is fetal erythrocytes, which can be identified by size column selection, followed by CD71-antibody staining or epsilon-globin chain immunophenotyping and then scanning or sorting based on fluorescence intensity, in certain embodiments.

Once the fetal cell(s) is isolated, nucleic acids are extracted therefrom, such as by routine methods in the art. The nucleic acid from the fetal cell(s) is subjected to methods of the disclosure to produce amplified cDNA that covers at least part, most, or all of the transcriptome of the fetal cell(s). Following amplification, one or more sequences of the amplicons may be further amplified and also may be sequenced, at least in part, or may be subjected to microarray techniques. In specific embodiments, a SNV is assayed for, and the results of the assay are utilized in determination of whether or not the corresponding fetus has a particular medical condition or is susceptible to having a particular medical condition, for example. In specific cases, the fetus may be treated for the medical condition or may be subjected to methods of prevention or delay of onset of the medical condition, and this may occur in utero and/or following birth, for example.

Although the fetal sample may be assayed for the presence of a SNV, in particular embodiments the fetal sample is assayed for a genetic mutation associated with any particular medical condition. Examples of genes associated with prenatal medical conditions that may be assayed for include one or more of the following: ACAD8, ACADSB, ACSF3, C7orf10, IFITM5, MTR, CYP11B1, CYP17A1, GNMT, HPD, TAT, AHCY, AGA, PLOD2, ATP5A1, C12orf65, MARS2, MRPL40, MTFMT, SERPINF1, FARS2, ALPL, TYROBP, GFM1, ACAT1, TFB1M, MRRF, MRPS2, MRPS22, MRPL44, MRPS18A, NARS2, HARS2, SARS2, AARS2, KARS, PLOD3, FBN1, FKBP10, RPGRIP1, RPGR, DFNB31, GPR98, PCDH15, USH1C, CERKL, CDHR1, LCA5, PROM1, TTC8, MFRP, ABHD12 CEP290, C8orf37, LEMD3, AIPL1, GUCY2D, CTSK, RP2, IMPG2, PDE6B, RBP3, PRCD, RLBP1, RGR, SAG, FLVCR1, ZNF513, MAK, NDUFB6, TMLHE, ALDOA, PGM1, ENO3, LARS2, ATP7A, ATP7B, TNFRSF11B, LMBRD1, MTRR, FAM123B, FAM20C, ANKH, TGFB1, SOST, TNFRSF11A, CA2, OSTM1, CLCN7, PPIB, TCIRG1, SLC39A13. COL1A2, TNFSF11, SLC34A1, NDUFAF5, FOXRED1, NDUFA2, NDUFA8, NDUFA10, NDUFA11, NDUFA13, NDUFAF3, SP7, NDUFS1, NDUFV3, NUBPL, TTC19, UQCRB, UQCRQ, COX4I1, COX4I2, COX7A1, TACO1, COL3A1, SLC9A3R1, CA4, FSCN2, BCKDHA, GUCA1B, KLHL7, IMPDH1, PRPF6, PRPF31, PRPF8, PRPF3, ROM1, SNRNP200, RP9, APRT, RD3, LRAT, TULP1, CRB1, SPATA7, USH1G, ACACB, BCKDHB, ACACA, TOPORS, PRKCG, NRL, NR2E3, RP1, RHO, BEST1, SEMA4A, RPE65, PRPH2, CNGB1, CNGA1, CRX, RDH12, C2orf71, DHDDS, EYS, IDH3B, MERTK, PDE6A, FAM161A, PDE6G, TYMP (ECGF1), POLG (POLG1, POLGA), TK2, DGUOK (dGK), SURF1, SCO2 (SCO1L), SCO1, COX10, BCS1L, ACADM, HADHA, ALDOB, G6PC (GSD1a), PAH (PH), OTC, GAMT, SLC6A8, SLC25A13, CPT2, PDHA1, SLC25A4 (ANT1), C10orf2 (TWINKLE), SDHA, SLC25A15, LRP-PRC, GALT, PMM2, ATPAF2 (ATP12), GALE, LPIN1, ATP5E, B4GALT7, ATP8B1 (ATPIC, PFIC), ABCB11 (ABC16, PFIC-2, PGY4), ABCB4 (GBD1, MDR2, PFIC-3), MPV17 (SYM1), TIMM8A (DDP, MTS), CPS1, NAGS, ACADVL, SLC22A5 (OCTN2), CPT1A (CPT1-L, L-CPT1), CPT1B, SUCLA2, POLG2 (HP55, MTPOLB), ACADL, SUCLG1, MCEE, GAA, PDSS1 (COQ1, TPT), PDSS2 (bA59I9.3), COQ2 (CL640, F1126072), RRM2B (p53R2), ARG1, SLC25A20 (CACT), MMACHC (cb1C), FAH, MPI, GA™, OPA1, TFAM, TOMM20 (MAS20P, TOM20), NDUFAF4 (HRPAP20, C6orf66), NDUFA1 (CI-MWFE, MWFE), SLC25A3 (PHC), BTD, OPA3 (F1122187, MGA3), GYS2, NDUFAF2 (B17.2L, MMTN), HLCS (HCS), COX15, FASTKD2, NDUFS4, NDUFS6, NDUFS3, MMAA (cblA), MUT, NDUFV1, MOCS1, NDUFS7 (PSST), TAZ (BTHS, G4.5, XAP-2), MOCS2, COX6B1 (COXG), HADHB, MCCC1 (MCCA), MCCC2 (MCCB), TSFM (EF-TS, EF-Tsmt), PUS1, ISCU, AGL, SDHAF1, IVD, GCDH, ADSL, DARS2, RARS2, TMEM70, ETHE1, PC, JAG1, MRPS16, PCCA, PCCB, COQ9, LDHA, PYGL, GALK1, PYGM, PGAM2, TUFM, TRMU, PFKM, GBE1, SLC37A4, GYS1, ETFDH, NDUFS8, CABC1 (ADCK3), ETFA, ETFB, DBT, SLC25A19, MMADHC, PDP1, PDHB, ACAD9, AUH, DLAT, PDHX, ACADS, NDUFS2, FBP1, NDUFAF1 (CIA30, CGI65), YARS2, SUCLG2, TCN2, CBS, PHKB, PHKG2, PHKA1, PHKA2, LIPA, ASL, HPRT1, OCRL, PNP, TSHR, ADA, ARSB, ALDH5A1, PNP, AMT, DECR1, HSD17B10, IYD, IL2RG, MGME1, HMGCL, IQCB1, OTX2, KCNJ13, CABP4, NMNAT1, ALG2, DOLK, ABCD4, ALDH4A1, ALG1, GPR143, UBE3A, ARX, GJB2 (CX26, NSRD1), APC, HTT, IKBKG (NEMO), DMPK, PTPN11, MECP2, MECP2, RECQL4, ATXN1, ATXN10, RMRP, CDKL5, PLP1, GLA, DMD, RUNX2, PLP1, CHD7, ASS1, AIRE, EIF2B, LDLR, HPRT1, RPS19, LMX1B, COL10A1, CRTAP, LEPRE1, PORCN, ASL, CFTR, ARSA, IDUA, IDS, MYO7A, GLANS, GALC, KRAS, SOS1, RAF1, AR, PTEN, BLM, SLC9A6, HRAS, GJC2 (GJA12), NPC1, NPC2, FMR1, FMR1, PLOD1, COL2A1, COL5A1, COL5A2, ABCA4, FOXG1, TINF2, USH2A, CDH23, CLRN1, CREBBP, ABCA4, POU3F4, NRAS, CHRNA7, FOXF1, MEF2C, DHCR7, RAIL VHL, TYR (OCAIA), OCA2 (BEY, BEY1, BEY2, EYCL), TYRP1 (b-PROTEIN, CATB, GP75, SLC45A2 (AIM-1), PCDH19, SHOC2, BRAF, MAP2K1, MAP2K2, HEXA, STXBP1, ALDH7A1, SLC2A1, WDR62, MAGEL2, SDHB, and FH.

B. Cancer Testing

In some embodiments of the disclosure, a sample from an individual that has cancer or is suspected of having cancer or is being monitored for cancer therapy outcome is subjected to methods of the disclosure. Other diagnostic or prognostic tests may be run on the sample or similar samples in addition to the methods of the disclosure. The sample may be obtained by routine methods and may include a biopsy comprising cells or tissue that appears to be, is suspected of being, or is known to be cancerous. Exemplary samples for cancer testing include blood, urine, biopsy, fecal matter, nipple aspirate, cheek scrapings and so forth. In some cases, a sample is obtained from an individual at risk for having cancer; such an individual may have a family and/or personal history, may have been exposed to environmental conditions known or suspected to cause cancer, may be known to have a genetic marker associated with at least one type of cancer, and so forth. Particular types of biopsies include of the skin, lung, breast, colon, cervix, liver, kidney, prostate, and so forth.

In particular embodiments, the sample being tested from an individual is subjected to methods of the disclosure related to assaying for variance in sequence content compared to a known sample or variance in expression level of a sequence compared to normal levels (such as upregulation or downregulation of one or more genes). In some cases, the expression level of one or more particular genes as represented in the amplicon quantities produced by methods of the disclosure is indicative of the presence of cancer or risk for having the cancer or success in therapy for the cancer.

Examples of genes that may be assayed for association with a particular cancer include one or more of the following: ER, PR, AR, BAG1, Bcl-2, CTNNB1, BRAF, FOS, JUN, EGFR, ERBB2, ETV6-NTRK3 gene fusion, Gankyrin, GT198, MDM2, MIG7, MYC, SRC, RAS, SKI, TCTP, ABL, CBL, ROS1, AKT, BAX, FKHR, CDK2, CDK4, CCND1, CCNE1, PIK3CA, HPV-E7, HPV-E6, AURKA, miR-155, FAS, GLI, SHH, SMO, NOTCH, ILK, RAR, SOX, WNT1, TAL1, MLL, HOXA1, MITF, EVI1, BCL6, HOXA9, APC, BRCA1, BRCA2, CDKN1B, CDKN1C, DLD/NP1, HEPACAM, INK4, miR-145, p15, p16, p53, p57, p63, p73, PTEN, Rb, SDHA, SDHB, SDHC, SDHD, SFRP1, TCF21, TIG1, TP53, TSC1/TSC2, and VHL, BCL2, INPP4B, LKB1, ARF, ATM/ATR, CHK1, CHK2, DNA-PK, FANCs, HIPK2, NBS1, WT1, MUTYH, BLM, RECQL4, WRN, MLH1, MSH2, MSH6, PMS2, XPA, XPC, XPD, FBXW7, PTCH1, SUFU, EXT1, EXT2, NF1, NF2, BMPR1A, SMAD2, SMAD3, SMAD4, TGFBR1, MEN1, APC, AXIN, CTNNA1, CDH1, WNT5A, GPC3, HRPT2, and HPC1.

In particular embodiments, the sample being tested from an individual may be tested for the expression of one or more tumor-specific antigens to aid in the selection of personalized therapies. Examples of tumor-specific antigens that may be assayed include EphA2, HER2, GD2, Glypican-3, 5T4, 8H9, integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CS1, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD3, HLA-AI, HLA-A2, IL11Ra, IL13Ra2, KDR, Lambda, Lewis-Y, MCSP, Mesothelin, Mucl, Muc16, NCAM, NKG2D ligands, NY-ESO-1, PRAME, PSCA, PSC1, PSMA, ROR1, Sp17, SURVIVIN, TAG72, TEM1, TEM8, carcinoembryonic antigen, HMW-MAA, VEGF receptors, MAGE-A1, MAGE-A3, MAGE-A4, CT83, SSX2, XIAP, cIAP1, cIAP2, NAIP, and/or Livin.

C. Immune Response Monitoring

In some embodiments of the disclosure, a sample from an individual being monitored for immunotherapy outcome is subjected to methods of the disclosure. Other diagnostic or prognostic tests may be run on the sample or similar samples in addition to the methods of the disclosure. The sample may be obtained by routine methods and may include a biopsy comprising cells or tissue that appears to be, is suspected of being, or is known to be cancerous. Exemplary samples for immune response testing include blood, biopsy, nipple aspirate, and so forth. Particular types of biopsies include of the skin, lung, breast, colon, cervix, liver, kidney, prostate, and so forth. Other diagnostic or prognostic tests may be run on the sample or similar samples in addition to the methods of the disclosure.

In particular embodiments, the sample being tested from an individual is subjected to methods of the disclosure related to assaying for variance in sequence content compared to a known sample or variance in expression level of a sequence compared to normal levels (such as upregulation or downregulation of one or more genes). In some cases, the expression level of one or more particular genes as represented in the amplicon quantities produced by methods of the disclosure is indicative of an acquired immune response or success in therapy for the cancer.

Examples of genes that may be assayed for monitoring the acquired immune response include CD3, CD8, GZMB, CD45RO, PTPRC and IFNG.

IV. Sample Processing and Nucleic Acids from Cells of the Invention

One or more samples from an individual being tested with methods of the disclosure may be obtained by any appropriate means. The sample may be processed prior to steps for extracting the nucleic acid, in certain embodiments. The sample may be fresh at the time the nucleic acid is extracted, or the sample may have been subjected to fixation or other processing techniques at the time the nucleic acid is extracted.

The sample may be of any kind. In embodiments wherein a cell or cells of interest are comprised among other cells, the cell or cells of interest may be isolated based on a unique feature of the desired cell or cells, such as a protein expressed on the surface of the cell. In embodiments wherein a fetal cell is isolated based on a cell marker, the cell marker may be CD71 or epsilon-globin chain, etc. In embodiments wherein a cancer cell is isolated based on a cancer marker, the cell marker may be ER/PR, EGFR, KRAS, BRAF, PDFGR, UGT1A1, EphA2, HER2, GD2, Glypican-3, 5T4, 8H9, αvβ6 integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CS1, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD3, HLA-AI, HLA-A2, IL11Ra, IL13Ra2, KDR, Lambda, Lewis-Y, MCSP, Mesothelin, Mucl, Muc16, NCAM, NKG2D ligands, NY-ESO-1, PRAME, PSCA, PSC1, PSMA, ROR1, Sp17, SURVIVIN, TAG72, TEM1, TEM8, carcinoembryonic antigen, HMW-MAA, VEGF receptors, MAGE-A1, MAGE-A3, MAGE-A4, CT83, SSX2, XIAP, cIAP1, cIAP2, NAIP, Livin, etc.

The isolated cell can be lysed by incubating the cell in RNase-free lysis buffer with surfactant (i.e. Trion-X100, tweet-20, NP-40, etc.), a reducing agent (i.e. dithiothreitol, etc.), and an RNase inhibitor (i.e. RNASEOUT™, etc.). Furthermore, cells can lysed in the presence of primers described in the disclosed method.

V. TCR Sequencing

The present invention utilizes steps in which nucleic acids are manipulated in order to sequence cell surface molecules, such as T cell receptors (TCRs), for example. In a general sense, in some embodiments of the invention, amplification of immune cell and/or T cell genetic material by the disclosed method is employed to generate transcriptome amplification of immune cell genetic material. For TCR molecules, the genetic information can be obtained from the total RNA of immune cells or T cells. RNA can be of the Variable (V) region or Constant (C) region. In preferred embodiments, the starting material is RNA from immune cells composed of V and C gene segments that encodes for a TCR, and contains the constant region.

Starting material for immune sequencing can include any polynucleotides, such as total RNA. The polynucleotides can be from immune cells. The polynucleotides can be composed of the V and C gene segments that encode for a TCR. The polynucleotides to be used as starting material can contain TCR constant regions. In some embodiments, RNA can be from T cells.

In certain embodiments, immune cells can be isolated from the blood or other biological samples of a subject or host, such as a human or other animal that has been immunized or that is suffering from an infection, cancer, an autoimmune condition, or any other diseases to identify a pathogen-, tumor-, and/or disease specific TCR of potential clinical significance. For example, the human may be diagnosed with a disease, be exhibiting symptoms of a disease, not be diagnosed with a disease, or not be exhibiting symptoms of a disease. For example, the human may be one that was exposed to an infectious agent (e.g., viruses, bacteria, parasites, prions, etc), antigen, or disease. For example, the animal may be one that was exposed to an infectious agent (e.g., viruses, bacteria, parasites, prions, etc.), antigen, or disease. Certain immune cells from immunized hosts make TCRs to one or more target antigens in question and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a sample of one or more immune cells before the total RNA is amplified by the disclosed method and sequenced.

V. Kits of the Disclosure

Any of the compositions described herein or similar thereto may be comprised in a kit. In a non-limiting example, one or more reagents for use in methods for amplification of nucleic acid may be comprised in a kit. Such reagents may include enzymes, buffers, nucleotides, salts, primers, and so forth. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effective Detection of Variation in Single Cell Transcriptomes Using MATQ-Seq The disclosed method encompasses a sensitive sequencing protocol called MATQ-seq, for Multiple Annealing and dC-Tailing based Quantitative single-cell RNA-seq. MATQ-seq can identify transcriptional variation among cells of the same population. Furthermore, the inventors systematically characterize technical noise in order to demonstrate that the detected transcriptional variation is biologically genuine. In contrast to popular existing methods in the art, for example SMART (Switching Mechanism At 5'-end of RNA Template) chemistry—based methods, MATQ-seq provides whole gene body coverage and the detection of total RNA, including noncoding and non-polyadenylated RNA. In addition, MATQ-seq removes PCR bias using a molecular barcoding strategy. Over 90 single cells have been sequenced using MATQ-seq to demonstrate its sensitivity and accuracy.

The sensitivity of single-cell RNA-seq depends on the efficiency of reverse transcription (RT) and the successful production of PCR amplicons after the RT step (Marinov, et al., 2014). To improve the efficiency of both first and second strand synthesis, the method begins by using primers that mainly contain G, A and T bases to perform ten cycles of annealing without an intervening melting step (FIG. 1A). These primers are based on Multiple Annealing and Looping Based Amplification Cycles (MALBAC), a quasilinear whole genome amplification method (Zong, et al., 2012). The hybridization of MALBAC primers to the internal regions of transcripts at low temperature promotes successful RT across the transcripts and allows the detection of non-polyadenylated RNA (FIG. 4 and Tables 1-3). MATQ-seq also utilizes MALBAC-dT primers to initiate RT from the polyadenylated tail of mRNAs. After RT, dC tailing on first strand cDNAs is performed, which enables efficient second-strand synthesis using G-enriched MALBAC primers.

TABLE 1

HEK293T clone-1 reads and indexes information

| Samples | Total raw reads | TOPHAT mapped Reads/Fragments (MAPQ = 50) | Indexed fragments covering the whole gene body | Indexed fragments covering the exons |
|---|---|---|---|---|
| SC-1 | 13437244 | 8024201/6479802 | 1301459 | 498628 |
| SC-2 | 18747724 | 11773949/9454964 | 1635790 | 810589 |
| SC-3 | 15563942 | 9211867/7463152 | 1417552 | 615314 |
| SC-4 | 17364270 | 10598932/8628038 | 1559656 | 714509 |
| SC-5 | 19124840 | 11655311/9482020 | 1618822 | 746869 |
| SC-6 | 13714734 | 9914975/8041604 | 1453136 | 759156 |
| SC-7 | 16221066 | 11741236/9437594 | 1539952 | 842264 |
| SC-8 | 22203620 | 16790511/14140630 | 2139357 | 963421 |
| SC-9 | 9559792 | 6101401/4584020 | 785987 | 546757 |
| SC-10 | 13149798 | 8912346/7282878 | 1307731 | 741378 |
| SC-11 | 16171270 | 10660433/8409988 | 1541798 | 861852 |
| SC-12 | 11594366 | 7736059/6262732 | 1147227 | 595229 |
| SC-13 | 14955770 | 10955300/8796616 | 1412680 | 825351 |
| SC-14 | 22002624 | 14079358/11374306 | 1769310 | 968724 |
| SC-15 | 23428248 | 6932973/5181578 | 1084941 | 465621 |
| SC-16 | 22238620 | 8865535/6648636 | 1182581 | 512662 |
| SC-17 | 19248016 | 7880566/5857480 | 985430 | 438492 |

TABLE 1-continued

HEK293T clone-1 reads and indexes information

| Samples | Total raw reads | TOPHAT mapped Reads/Fragments (MAPQ = 50) | Indexed fragments covering the whole gene body | Indexed fragments covering the exons |
|---|---|---|---|---|
| SC-18 | 20327376 | 5614111/3873374 | 872719 | 510356 |
| SC-19 | 18297544 | 9339254/7566208 | 1223900 | 580061 |
| SC-20 | 25619392 | 15912144/12944606 | 2166166 | 1026235 |
| SC-21 | 22684820 | 13956740/11340782 | 2199943 | 1200398 |
| SC-22 | 18789966 | 7921379/5916036 | 1199125 | 671910 |
| SC-23 | 14619532 | 10433774/8281092 | 1281337 | 670073 |
| SC-24 | 10620304 | 7314174/5756790 | 956737 | 528647 |
| SC-25 | 12653476 | 8650275/6890918 | 1030781 | 477530 |
| SC-26 | 11796236 | 8131067/6467184 | 1088497 | 608791 |
| SC-27 | 12882722 | 8883177/7194134 | 1132731 | 605543 |
| SC-28 | 13968018 | 10236145/8186556 | 1255625 | 704360 |
| SC-29 | 17294318 | 12856697/10501554 | 1701537 | 860004 |
| SC-30 | 15002190 | 10510690/8224306 | 1334645 | 777209 |
| SC-31 | 17607646 | 12503918/10108720 | 1566661 | 671990 |
| SC-32 | 21881282 | 12205037/9911682 | 1687414 | 881336 |
| SC-33 | 21402876 | 15973269/12547572 | 2026233 | 1232731 |
| SC-34 | 11077480 | 6947229/5382772 | 844942 | 520691 |
| SC-35 | 19553216 | 14406809/11369448 | 1675019 | 1050363 |
| SC-36 | 12839736 | 8906268/6776634 | 1190013 | 922028 |
| SC-37 | 21828544 | 13547138/10629012 | 1837539 | 1287542 |
| SC-38 | 11007978 | 6664112/4952914 | 986505 | 662329 |
| SC.Avg-1 | 12926686 | 8794255/6992740 | 969905 | 478599 |
| SC.Avg-2 | 18466834 | 12535217/10179776 | 1804598 | 855714 |
| SC.Avg-3 | 24725278 | 14336940/11482856 | 1700773 | 807500 |
| SC.Avg-4 | 11617722 | 7129748/5750208 | 875901 | 417267 |
| SC.Avg-5 | 13409094 | 7694456/6216016 | 963749 | 451722 |
| SC.Avg-6 | 14854634 | 10027059/8222124 | 1244060 | 538860 |
| SC.Avg-7 | 15141678 | 9361760/7554384 | 1244268 | 550212 |
| SC.Avg-8 | 13566154 | 8810976/7110968 | 1123013 | 522377 |
| SC.Avg-9 | 11465198 | 6816025/5528014 | 882712 | 397568 |
| SC.Avg-10 | 12739132 | 8475462/6853556 | 1086323 | 504624 |

*The above sequencing experiment were performed with DSN treatment.

TABLE 2

HEK293T clone-2 reads and indexes information

| Samples | Total raw reads | TOPHAT mapped Reads/Fragments (MAPQ = 50) | Indexed fragments covering the whole gene body | Indexed fragments covering the exons |
|---|---|---|---|---|
| Avg. SC-1 | 22,722,144 | 10,351,618/6,351,857 | 1,237,871 | 422,130 |
| Avg. SC-2 | 25,667,018 | 12,827,026/7,931,296 | 1,504,964 | 535,405 |
| Avg. SC-3 | 18,989,546 | 8,664,415/5,381,244 | 1,138039 | 387,307 |
| Avg. SC-4 | 20,432,506 | 10,294041/6,478,708 | 1,294,295 | 452,574 |
| Avg. SC-5 | 22,875,452 | 11,657,761/7,204,073 | 1,454,445 | 516,187 |
| Avg. SC-6 | 18,768,348 | 8,145,325/5,084,767 | 1,169,047 | 409,054 |
| Avg. SC-7 | 19,432,082 | 8,646,843/5,419,605 | 1,241,480 | 445,799 |
| Avg. SC-8 | 25,872,488 | 5,566,444/3,494,897 | 716,740 | 243,950 |
| Avg. SC-9 | 22,554,418 | 5,519,167/3,430,734 | 697,725 | 239,362 |
| Avg. SC-10 | 18,829,686 | 3,503,633/2,218,802 | 466,610 | 155,488 |
| SC-1 | 18,373,830 | 6,815,946/4,455,370 | 873,350 | 287,525 |
| SC-2 | 19,833,488 | 9,601,783/5,931,876 | 1,019,217 | 341,857 |
| SC-3 | 21060782 | 11,945,939/7,475,401 | 1,410,120 | 613,580 |
| SC-4 | 15,770,270 | 5,765,894/3,613,489 | 806,466 | 317,447 |
| SC-5 | 19,458,702 | 8,891,112/5,523,832 | 1038,213 | 341,572 |
| SC-6 | 16,226,044 | 5,133,306/3,247,639 | 695,276 | 227,651 |
| SC-7 | 11,961,024 | 4,425,093/2,773,104 | 586,761 | 192,383 |
| SC-8 | 26,413,688 | 8,979583/5,697,330 | 1,176,584 | 481,116 |
| SC-9 | 17,188,900 | 4,983,276/3,207,302 | 685,564 | 283,252 |
| SC-10 | 21,326,816 | 9,412,717/5,894,456 | 1,180,185 | 436,180 |

*The above sequencing experiment were first done without DSN treatment. ~50% reads were consumed by ribosome RNA. Single-cell averages are down sampled to the averaged sequencing depth of single cells in PCA analyses and Z-test.

TABLE 3

MCF10A reads and indexes information

| Samples | Total raw reads | TOPHAT mapped Reads/Fragments (MAPQ = 50) | Indexed fragments covering the whole gene body | Indexed fragments covering the exons |
|---|---|---|---|---|
| Avg. MCF10A-1 | 29,222,312 | 7,211,901/4,676,966 | 477,911 | 213,247 |
| Avg. MCF10A-2 | 25,151,620 | 5,962,810/3,891,952 | 427,442 | 191,915 |
| Avg. MCF10A-3 | 21,624,302 | 5,605926/2,802,963 | 334,278 | 133,352 |
| Avg. MCF10A-4 | 24,365,926 | 6,734,090/4,301,569 | 487,754 | 199,762 |
| Avg. MCF10A-5 | 26,870,388 | 6,885326/4,483,204 | 564,374 | 278,166 |
| Avg. MCF10A-6 | 28,601,658 | 7,434,948/4,821,084 | 480,736 | 198,236 |
| MCF10A-1 | 24,669,790 | 7,653,178/4,903,431 | 672,622 | 238,305 |
| MCF10A-2 | 26,654,052 | 6,681,922/4,371215 | 483129 | 201,733 |
| MCF10A-3 | 25,292,200 | 6,073,960/4,057,353 | 741,549 | 422,476 |
| MCF10A-4 | 24,119,034 | 6,927,322/4,433,824 | 496,884 | 227,096 |
| MCF10A-5 | 29,722186 | 7,285,493/4,788,058 | 413,785 | 185,812 |
| MCF10A-6 | 37,424,524 | 8,609,410/5,576,619 | 587,477 | 226,589 |

PCR amplification following second-strand synthesis can introduce exponentially increasing bias but the use of unique molecular identifiers (UMIs) can significantly reduce this bias (Islam, et al., 2014; Kivioj a, et al., 2012). In MATQ-seq, random hexamer UMI sequences that we refer to as amplicon indexes or "barcodes" are introduced during second-strand synthesis (FIG. 1A) to label unique molecules prior to PCR amplification.

Figure 5:
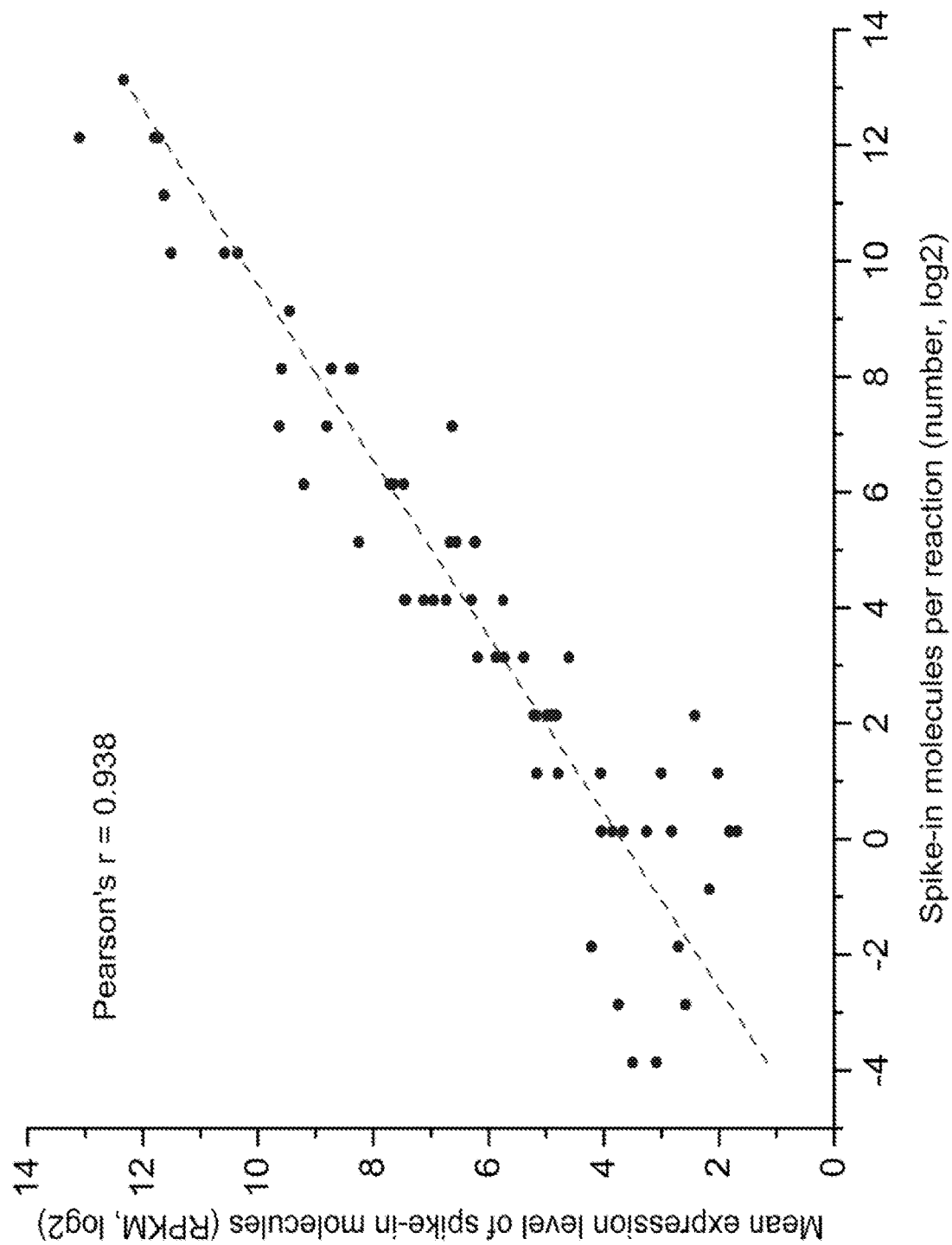
FIG. 5 illustrates the mean expression level of External RNA Controls Consortium (ERCC) spike-ins versus the spike-in molecules per reactions. The inventors sequenced 6 averaged one-fifth single-cell samples with 2-million-fold diluted ERCC spike-in. For 2-million-fold dilution, there are 7 spike-ins have on average 1.1 molecule per sample (ERCC-00014, ERCC-00028, ERCC-00039, ERCC-00067, ERCC-00077, ERCC-00143, and ERCC-00150). In six experiments, the times of detection of these seven genes are 2, 5, 3, 2, 5, 5, and 3 respectively. The detection efficiency for these spike-ins is estimated to be (2+5+3+2+5+5+3)/7/6=3.57/6=59.5%±8.8%. For transcript number mean equals to 1.1, a Poisson distribution will have 66.7% non-zero frequency. Therefore, the capture efficiency of MATQ-seq on ERCC spike-ins is (59.5%±8.8%)/66.7%=89.2%±13.2%.
Figure 6:
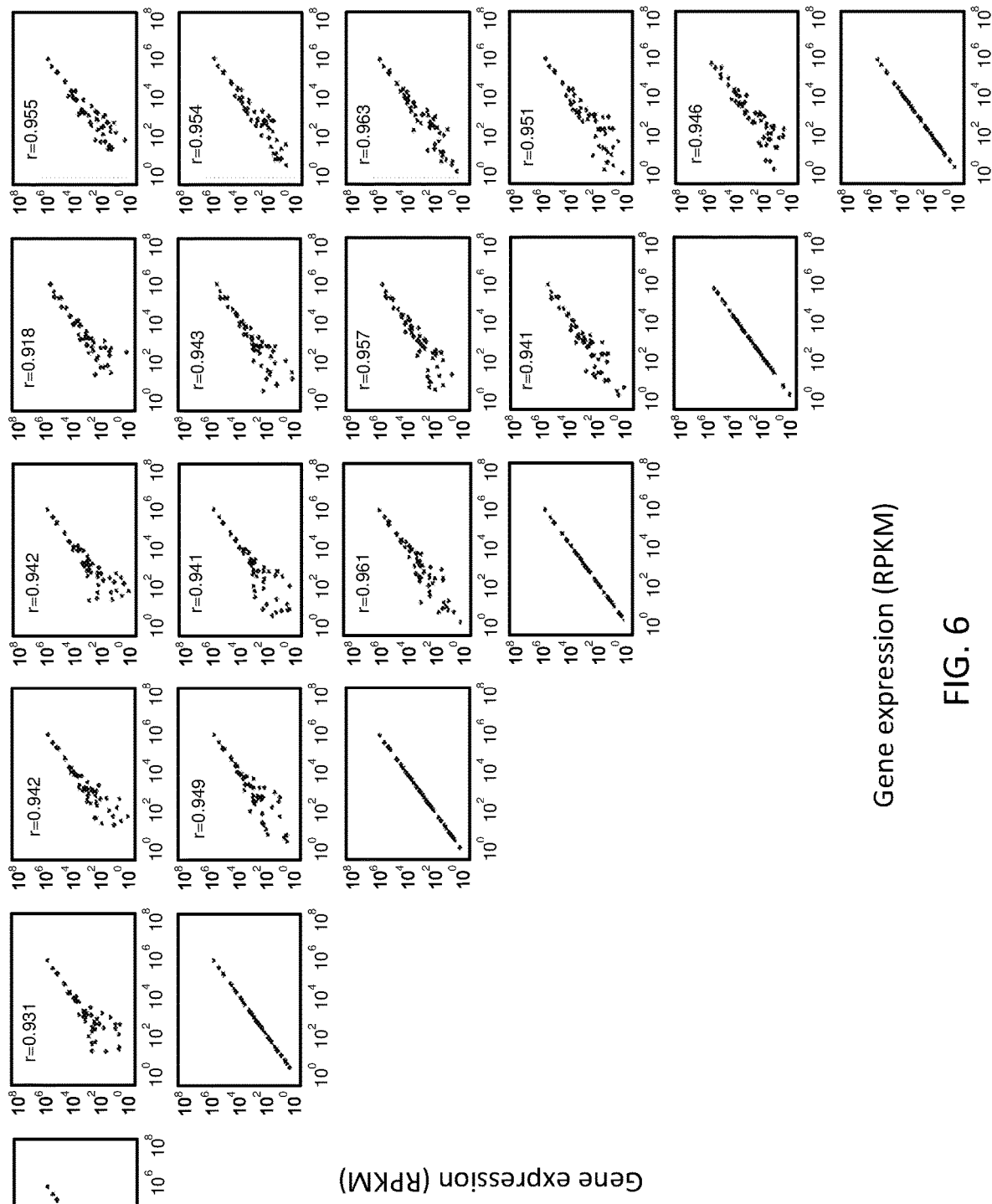
FIG. 6 shows the pairwise correlation of gene expression levels for 6 ERCC spike-in samples. The log-log Pearson's correlation coefficients are shown in each plot. The ERCC spike-ins are highly correlated with the averaged Pearson's correlation coefficient equals to 0.946±0.003, demonstrating high reproducibility of MATQ-seq.

To evaluate the sensitivity of single-cell RNA-seq methods, External RNA Control Consortium (ERCC) RNA spike-ins are often used as external controls (Wu, et al., 2014; Islam, et al., 2014). ERCC spike-in data shows that MATQ-seq achieves 89.2%±13.2% capture efficiency (FIG. 5) and ERCC levels are highly correlated between samples (log-log Pearson correlation coefficient of 0.94 for RPKM-normalized expression; FIG. 6). However, since ERCC spike-ins do not represent the complexity of mammalian RNA, they are likely to overestimate sensitivity. In this example, single HEK293T cells are sequenced as a way to compare against popular methods such as SMART-seq2 and SUPeR-seq that have been used to sequence the same cell type (Ramskold, et al., 2012; Picelli, et al., 2013; Islam, et al., 2014; Fan, et al., 2015).

Using MATQ-Seq, no obvious 3' or 5' end bias was observed in HEK293T transcripts, whereas SMART-seq2 shows mild 5' bias and SUPeR-seq shows mild 3' end bias (FIG. 1B). Furthermore, the indexed reads exhibit no significant end bias (FIG. 7). 18354±816 genes were detected in single HEK293T cells. Compared to SMART-seq2, MATQ-seq increases detection efficiency for low abundance genes by 40.8% (8968±833 vs. 6370±200, RPM≤10, FIG. 1C). At a low expression value of $\log_{10}(RPM)=0.5$, MATQ-seq has ~80% detection efficiency while SMART-seq2 achieves ~50% (FIG. 1D). MATQ-seq also detected 1904±105 long noncoding RNAs, and 50.4±2.5 pre-miR-NAs (FIG. 4).

To remove the dependence of gene expression on sequencing depth, the number of amplicons for each gene was normalized to the total number of unique amplicons detected in the cell. The inventors introduce the unit of APM (the number of amplicons per million amplicons in a single cell) to quantify gene expression level, similar to RPM (reads per million reads). The direct counting of amplicons covering the same loci can be used to estimate the total number of transcripts, but this requires sufficient sequencing depth. Using the normalized unit APM, gene expression can be directly compared between cells without a stringent sequencing depth requirement, while retaining the quantitative advantage of the UMI strategy.

Figure 9:
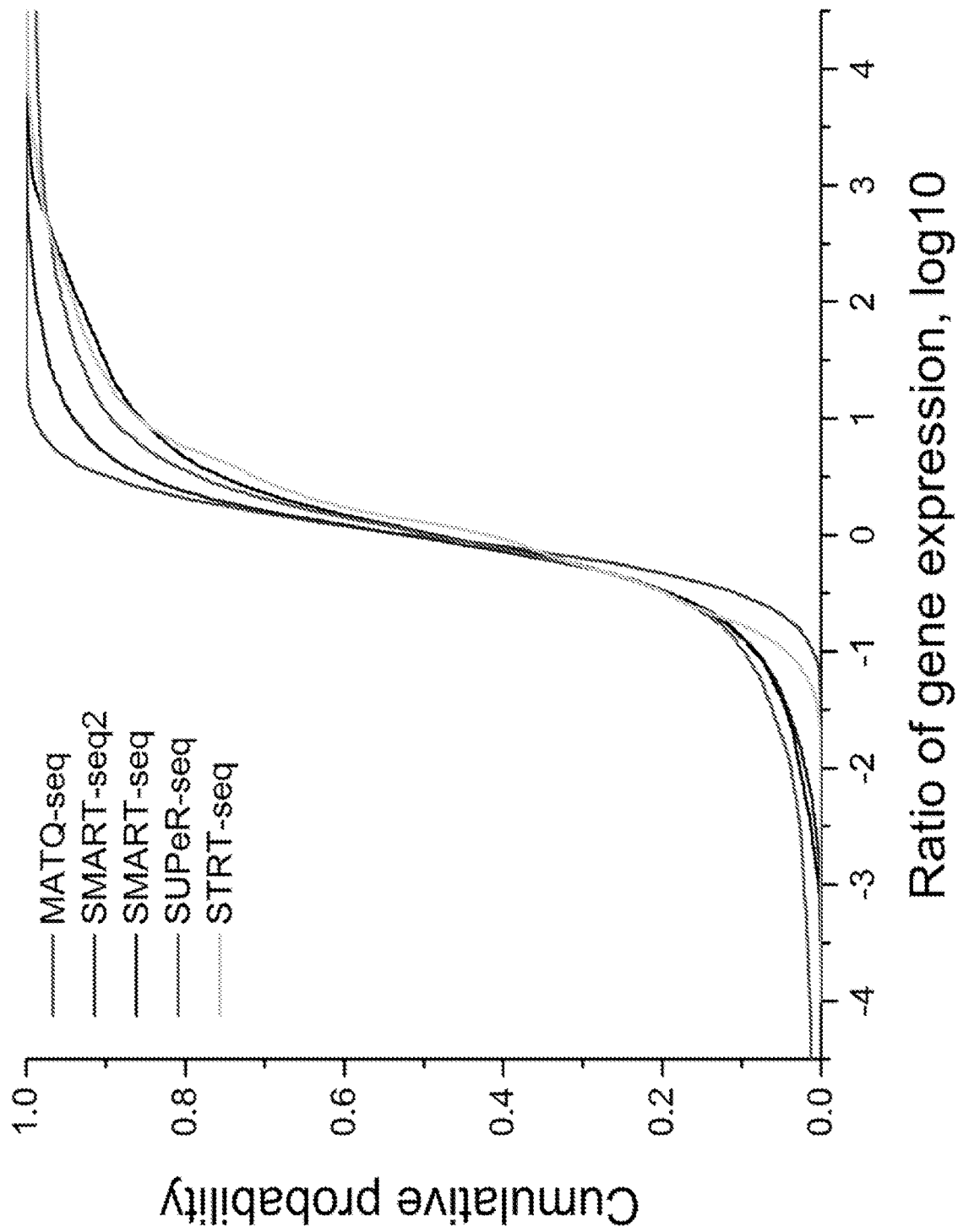
FIG. 9 illustrates the cumulative probability of the ratio of gene expression of the disclosed method (MATQ-seq) compared to existing methods. The gene expression ratio data described in FIG. 1E and FIG. 8 are used to generate the probability density function. The accumulative curves of the probability density functions for different assays are plotted. The x-axis indicates the ratio of gene expression in log 10 scale, and the y-axis indicates the accumulated probability. The P values of KS test between MATQ-seq and SMART-seq2, SMART-seq, SuPeR-seq and STRT-seq are $5.8838 \times 10^{-21}$, $7.1819 \times 10^{-49}$, $9.6261 \times 10^{-32}$ and $7.2462 \times 10^{-81}$ respectively.

Next, the histogram of pairwise-gene-expression-ratio (PGER) between any pairs of single cells was plotted to evaluate the accuracy and the reproducibility of single cell RNA-seq methods (FIG. 1E). In comparison to SMART-seq2, MATQ-seq has a narrower histogram distribution and more reproducibly detected genes, indicating less variability between measurements. Kolmogorov-Smirnov tests on cumulative PGER probabilities (FIGS. 8-9) strongly reject the null hypothesis that the two histograms come from the same distribution ($p=5.88\times10^{-21}$). The PGER histograms for a few other single-cell RNA-seq assays and KS tests were plotted and showed that MATQ-seq has the narrowest distribution (FIGS. 8-9).

In order to confirm that the observed transcriptional variation is genuine, it is critical to measure the technical noise of the single-cell RNA-seq assay. To assess technical noise, the inventors pooled 40 HEK293T cells, split their mixed lysate into 40 parts, and sequenced 10 of these single-cell averages with MATQ-seq (Marinov, et al., 2014). In contrast to spike-in transcripts, sequencing single-cell averages allowed the inventors to directly assess the technical variation associated with each gene in the transcriptome. In addition, the inventors amplified and sequenced 38 single HEK293T cells.

Figure 2F:
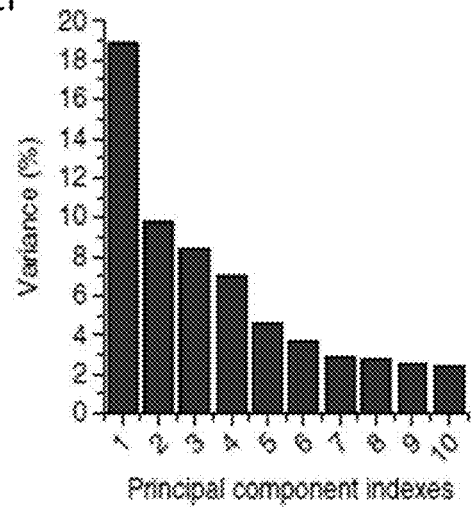

Single-cell averages tightly localize to the center of the single cell distribution in a principle component analysis (PCA, FIGS. 2A-2E). The percentage of variance explained by the first seven principal components decrease gradually (FIG. 2F). When RPM read counts are used to quantify gene expression, the single-cell averages no longer localize to the center of the single cell distribution (FIGS. 10A-10C). Furthermore, the percentage of variance of the first two components is over 99%, indicating dominance by PCR bias. These observations clearly demonstrate that UMIs are critical for reducing PCR-dependent technical noise.

Figure 11:
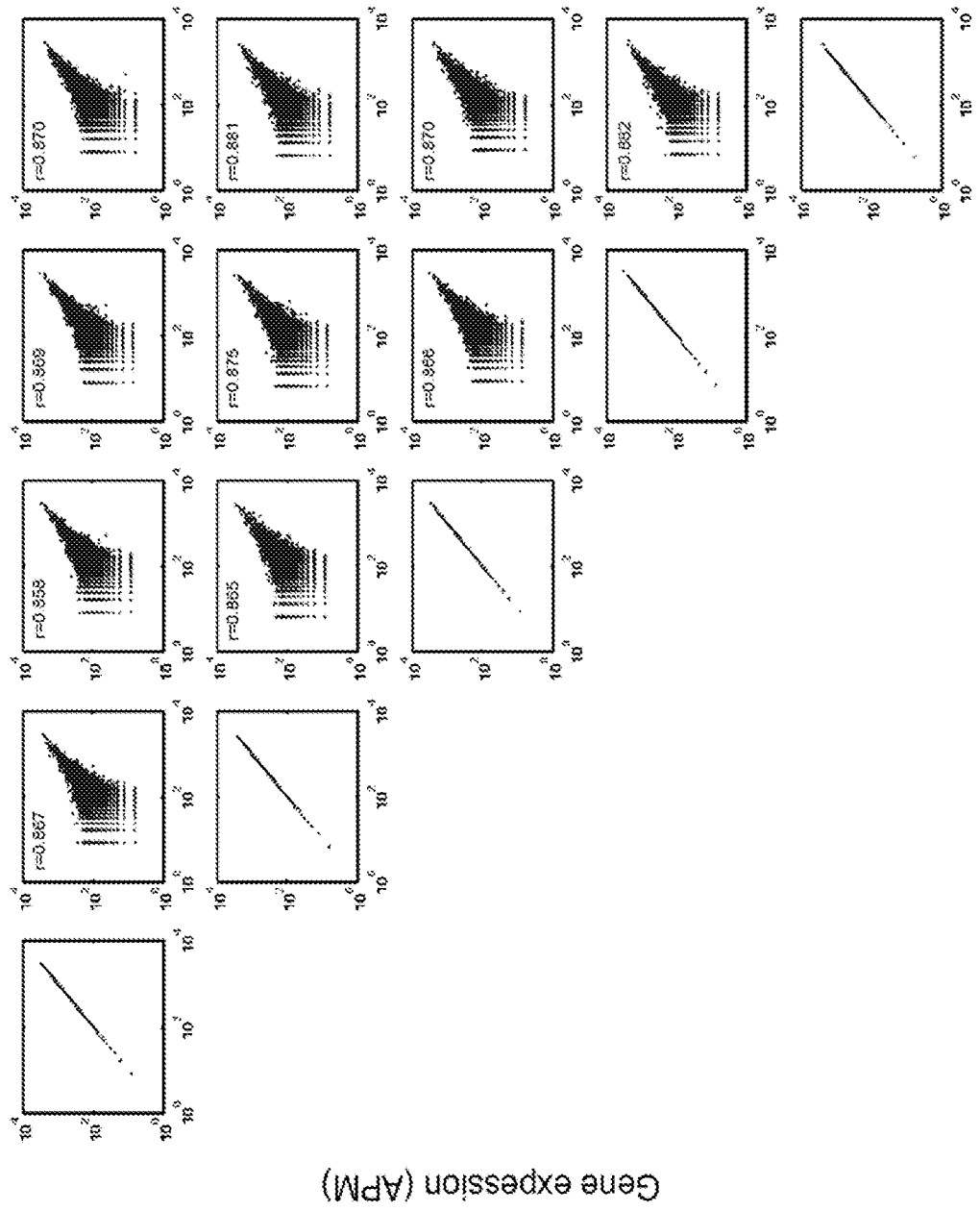
FIG. 11 illustrates the pairwise comparison of gene expression levels for single-cell averages. Five HEK293T single-cell averages were randomly selected. Amplicons per million amplicons (exon-based quantifications) was used for gene expression quantification. The log-log Pearson's correlation coefficients are shown on the plots. High log-log correlation coefficients demonstrate high reproducibility of MATQ-seq.
Figure 12:
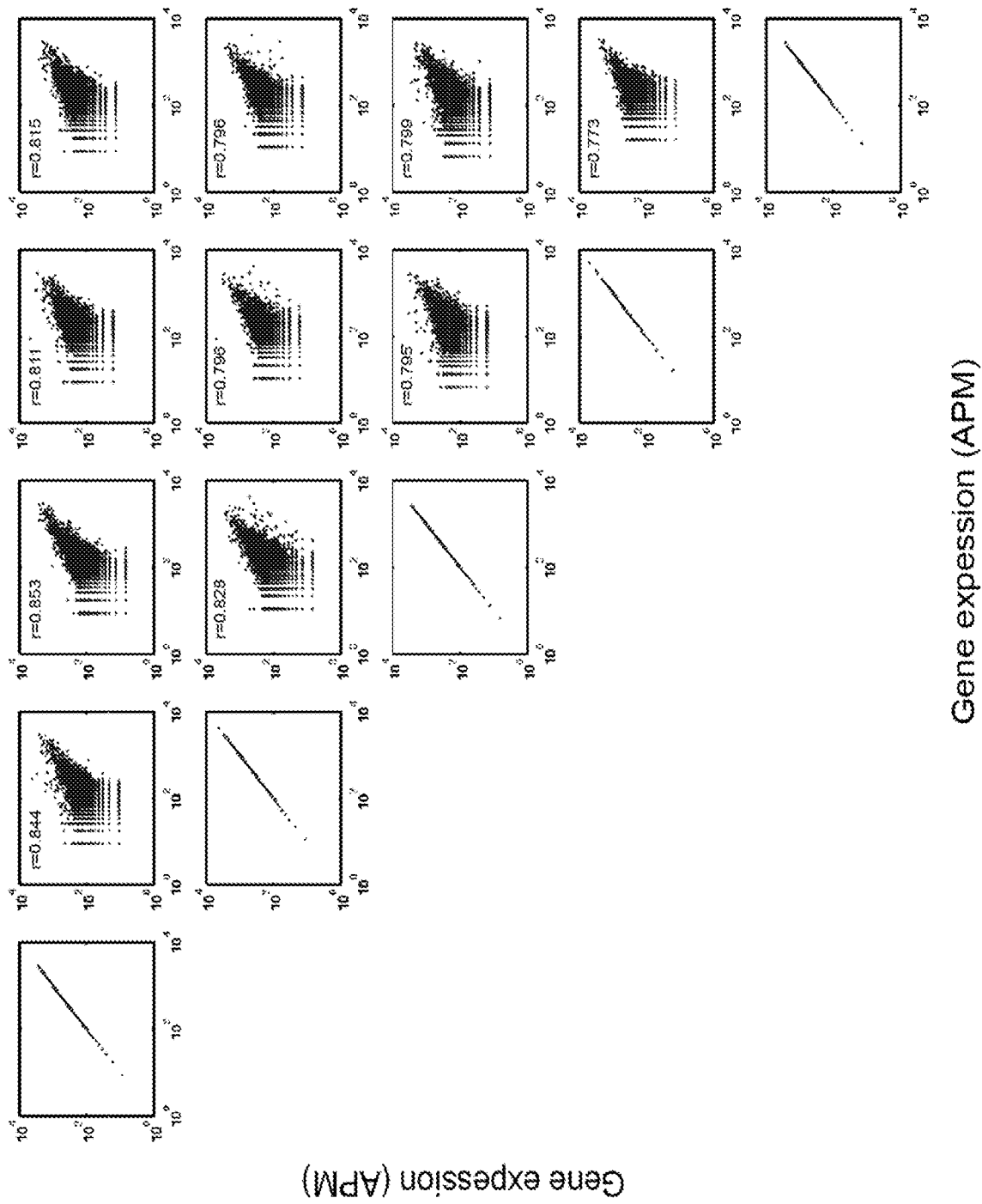
FIG. 12 illustrates the pairwise comparison of gene expression levels for individual single cells. Five HEK293T single cell samples were randomly selected. Amplicons per million amplicons (exon-based quantifications) was used for gene expression level. The log-log Pearson's correlation coefficients are shown on the plots. The single cells are less correlated compared to the single-cell averages (FIG. 19), indicating the existence of heterogeneity among single cells.

Next the mean expression level and standard deviation of genes between single cells and single-cell averages were compared. Mean expression levels are highly correlated (FIG. 3A). In contrast, a significant number of genes in single cells exhibit greater variation than in single-cell averages (FIG. 3B), indicating successful detection of biological variation in the single cells. Consistent with this observation, pairwise single-cell averages also show better correlation than those between single cell samples (FIGS. 11-12). For each gene, we calculated skewness to show the degree of asymmetry in the distribution of gene expression. Single-cell averages show limited skewness with the underlying Poisson distribution (FIG. 3C). In contrast, more genes have large skewness values for single cells (238 genes with skewness >2.0).

Figure 13A:
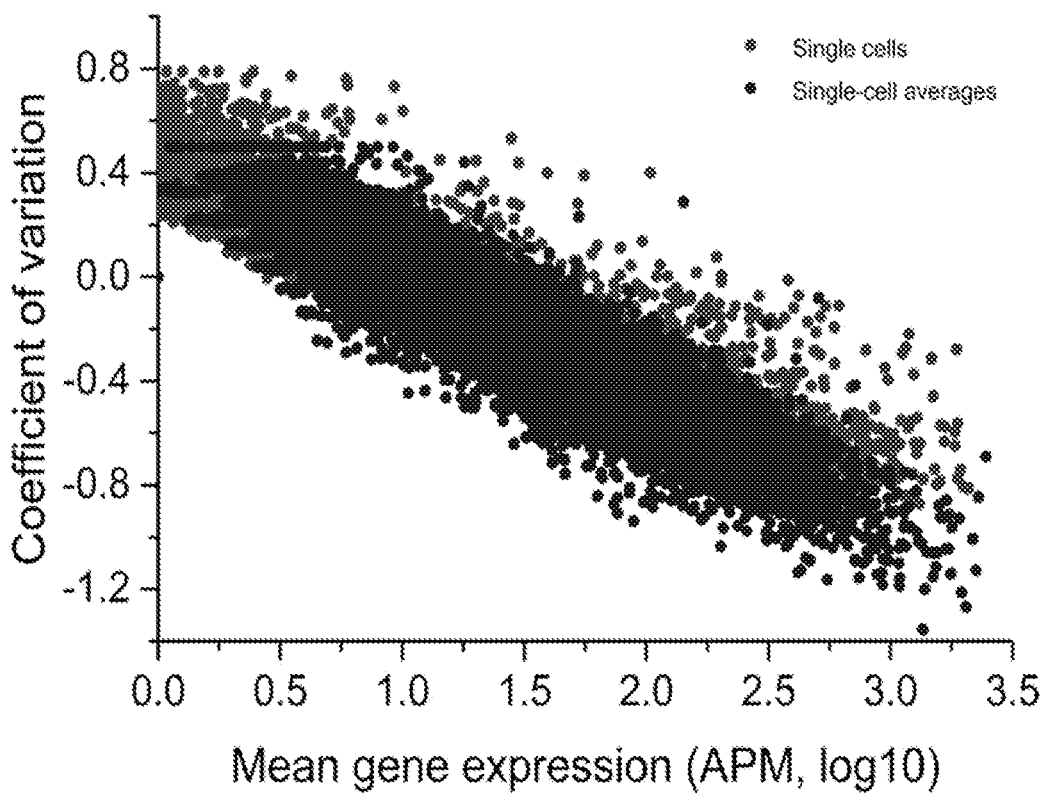
FIGS. 13A-13B.
Figure 13B:
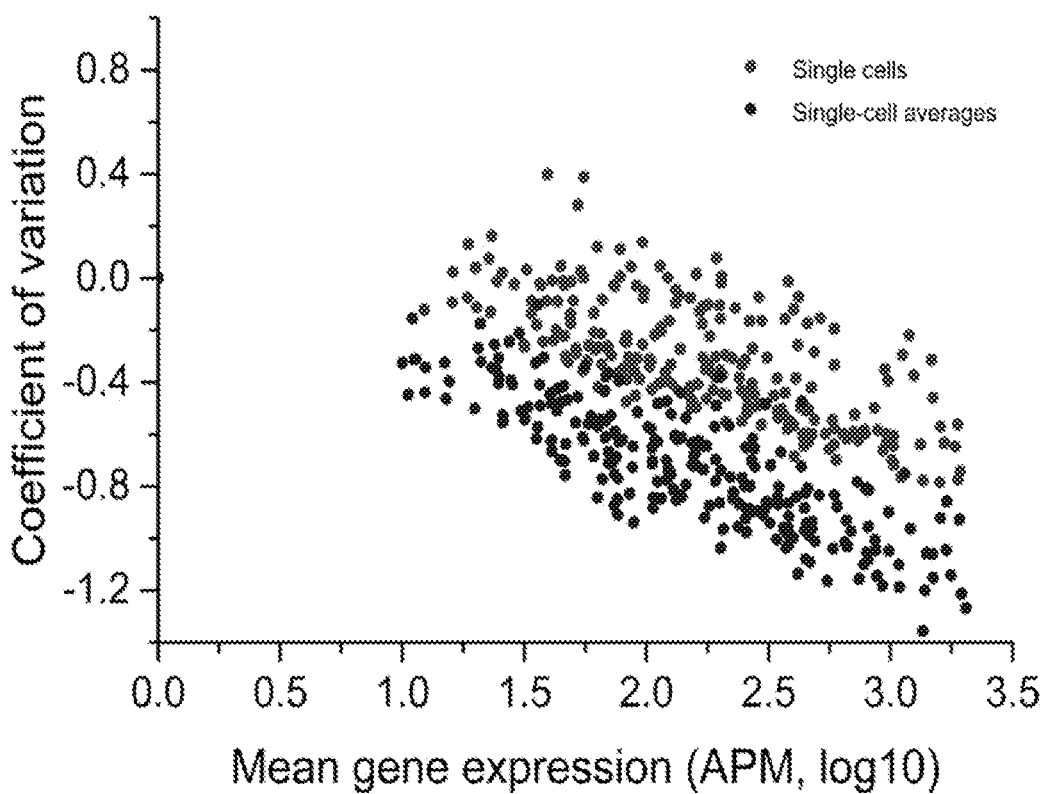

To identify genes with biological variation that is larger than the technical noise, an F-test (38 single cells vs. 10 single cell-averages) for each gene was performed using the null hypothesis that gene expression variance in single cells and single-cell averages is the same. The Benjamini-Hochberg procedure was used for multiple testing correction. Significant non-Poissonian variation was identified as a rejection of the null hypothesis for 234 genes with FDR<0.1 and 1009 genes with FDR<0.3 (FIG. 13 for coefficients of variation). Interestingly, the percentage of the non-Poissonian genes is consistent with a recent RNA-FISH study that measured transcriptional variability at large scale (Battich, et al., 2015). Unlike fluorescent imaging, MATQ-seq allows the measurement of variation at the whole transcriptome scale.

Transcriptional bursting dynamics are often characterized by the Fano factor (the ratio of variance to mean gene expression), which directly corresponds to the burst size in the negative binomial or gamma distribution of transcripts (Golding, et al., 2005; Raj, et al., 2008). 38 single cells were split into two random sets of 19 cells a correlation (r=0.52) was found between Fano factors of the two independent sets (FIG. 3D). In contrast, when single cells are compared with the single-cell averages (FIG. 3E), no correlation is observed (r=0.16). This suggests that MATQ-seq reliably detects variation in single-cell gene expression that is due to transcriptional bursting.

Figure 15A:
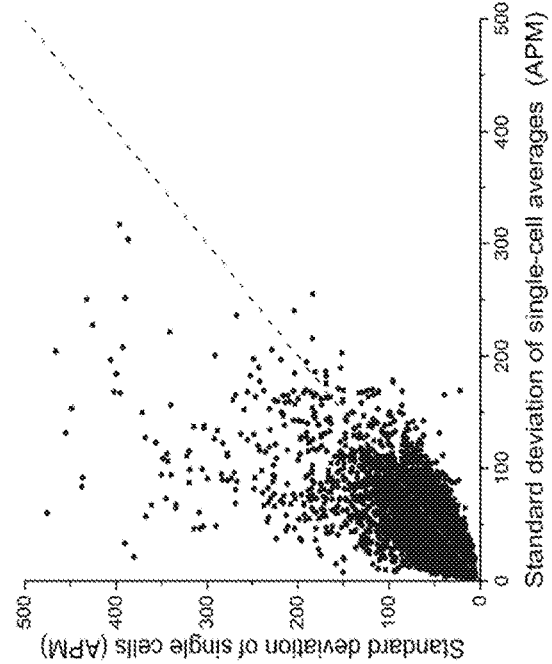
FIGS. 15A-15C.
Figure 15B:
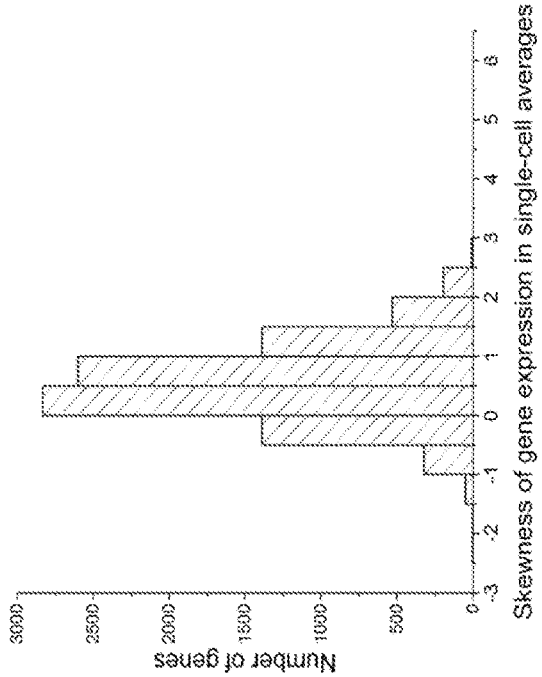
Figure 15C:
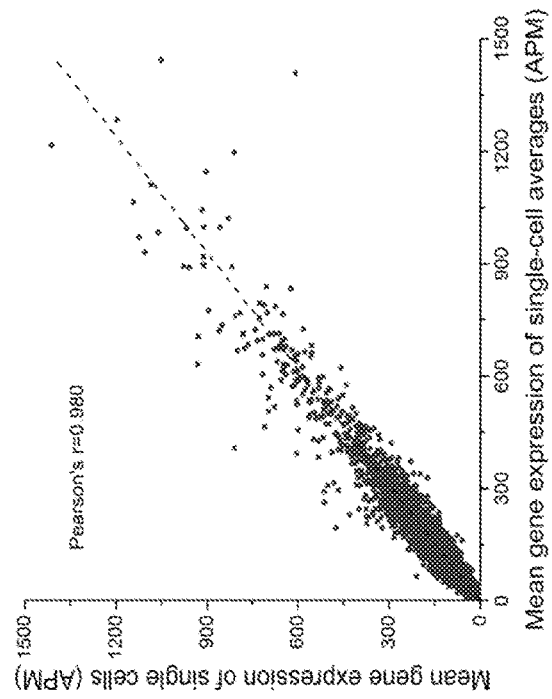
Figure 15D:
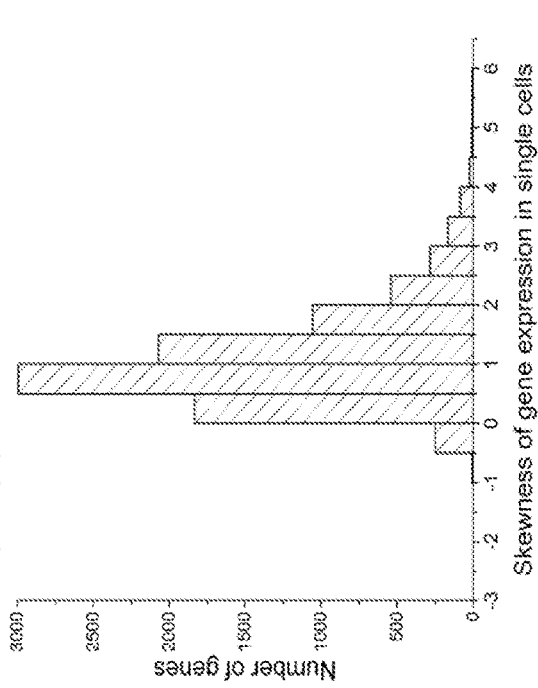
(FIG. 15D) The skewness of gene expression in single-cell averages. Compared with the single-cell averages, single cells gene expression skewness distribution has a long tail with large skewness, indicating the large gene expression variations captured by MATQ-seq.
Figure 16A:
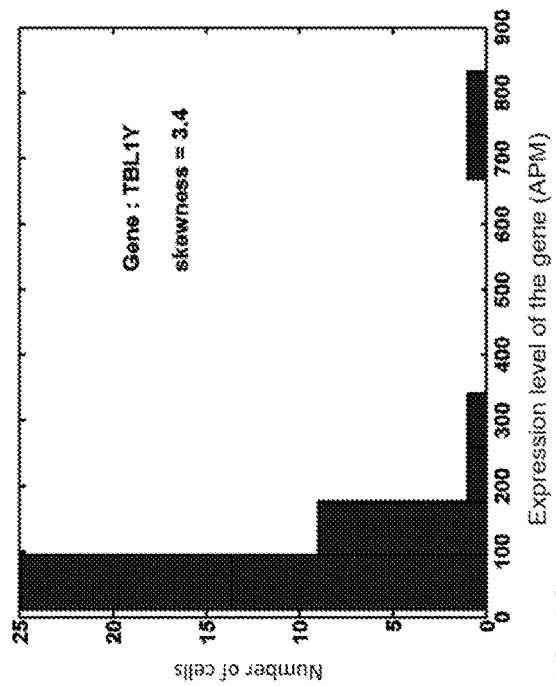
FIGS. 16A-16D illustrate examples of genes of different skewness in the histogram of gene expression for 4 genes in 38 HEK293T single cells (clone-1).
Figure 16B:
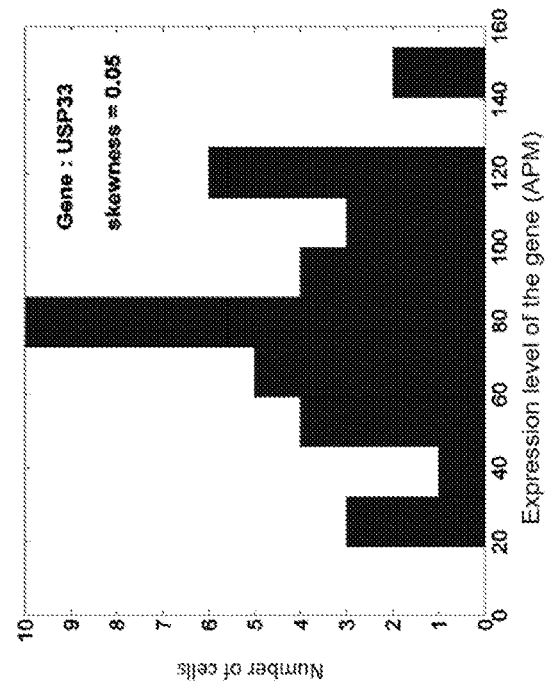
Figure 16C:
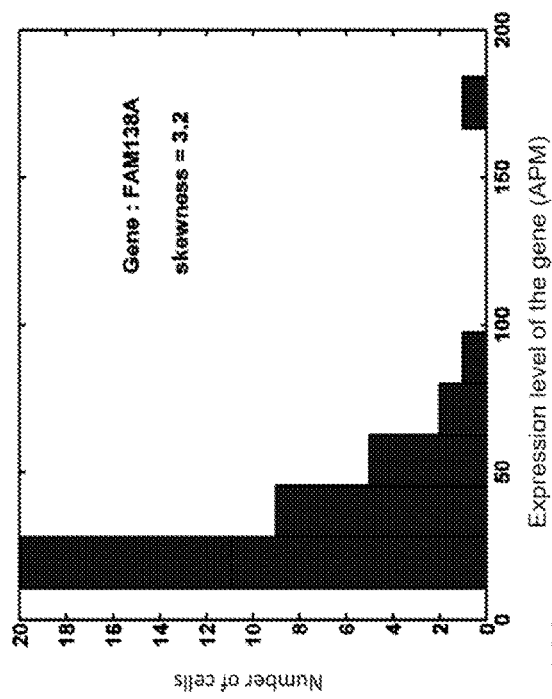
Figure 16D:
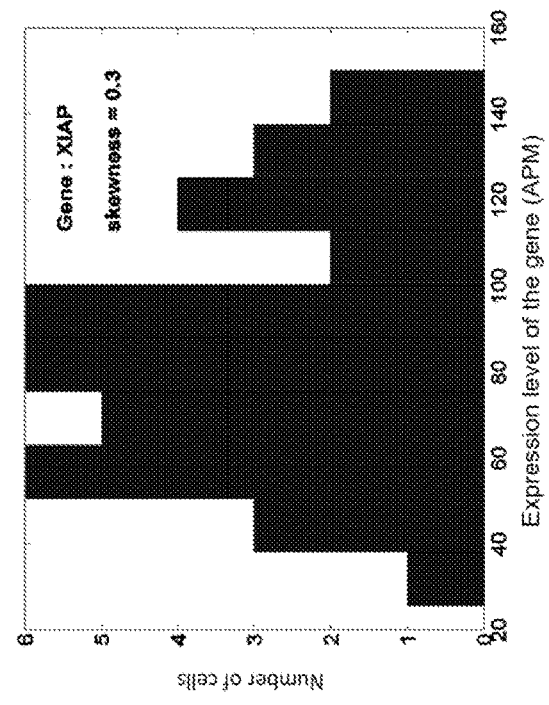

Since MATQ-seq allows the detection of both polyadenylated mature RNA and nonpolyadenylated pre-mRNA, gene expression can be quantified based on reads mapped to intronic regions. Using intron-based expression values, single-cell averages also localize tightly to the center of single cells in PCA (FIG. 14) and the means and variances between single cells and single-cell averages compare in a similar way to exon-based measures (FIGS. 15A-15B). With the F-test and Benjamini-Hochberg correction, 1126 significantly variable genes were identified at FDR<0.1. These variations in pre-mRNA can directly reflect the events of transcriptional bursts; indeed, many genes exhibit large skewness using intron-based expression (1116 genes>2.0) (FIGS. 15C-15D; see FIG. 16 for some examples). For highly skewed genes (e.g. FAM138A and TBL1Y), bursts were clearly captured in a few cells.

Of the 1009 and 1126 genes identified by exon- and intron-based analyses respectively, only 47 genes are shared by both measurements, indicating different sources of non-Poissonian variation in mature and premature RNAs. For both sets of genes, transcription-factor-binding-site (TFBS) analysis was performed to identify transcription factors that are potentially associated with transcriptional bursting. Interestingly, only 3 proteins were identified (P-val<$1\times10^{-10}$) using the genes from the exon-based measurement. In contrast, 159 proteins were identified using the genes from intron-based measurement, suggesting that transcription factor target enrichment occurs in genes with single-cell variability in premature RNA.

Among the 159 proteins involved in the regulation of the transcriptional bursts with intron-based measurement, transcription factors that interact with a large number of genes ('master regulators') are enriched compared to a TFBS analysis using a randomly selected gene set. It is worth noting that many of these regulators are expressed at low levels. For example, the top candidate genes NFX3A (related to 552 genes based on DAVID analysis) and FREAC2 (related to 517 genes) are found at very low levels (RPKM≈4 and 6, respectively, based on single-cell averages). This observation indicates that low-level expression of master regulators is associated with the transcriptional bursts of many genes observed with intron-based measurement.

Figure 17A:
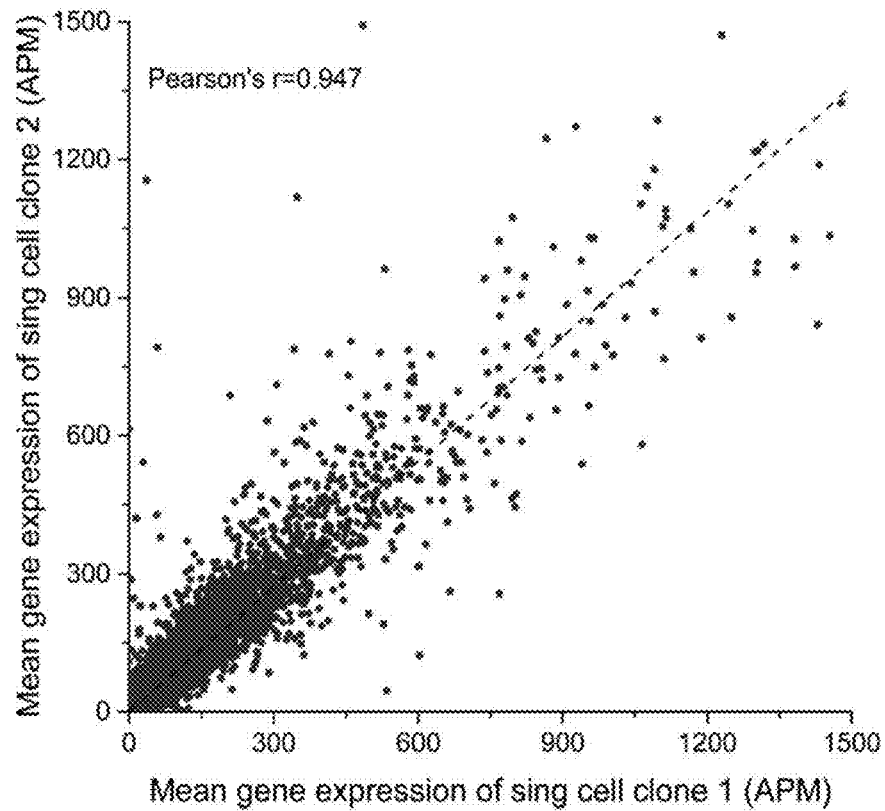
FIGS. 17A-17B show the similarity between two different HEK293T clones.
Figure 17B:
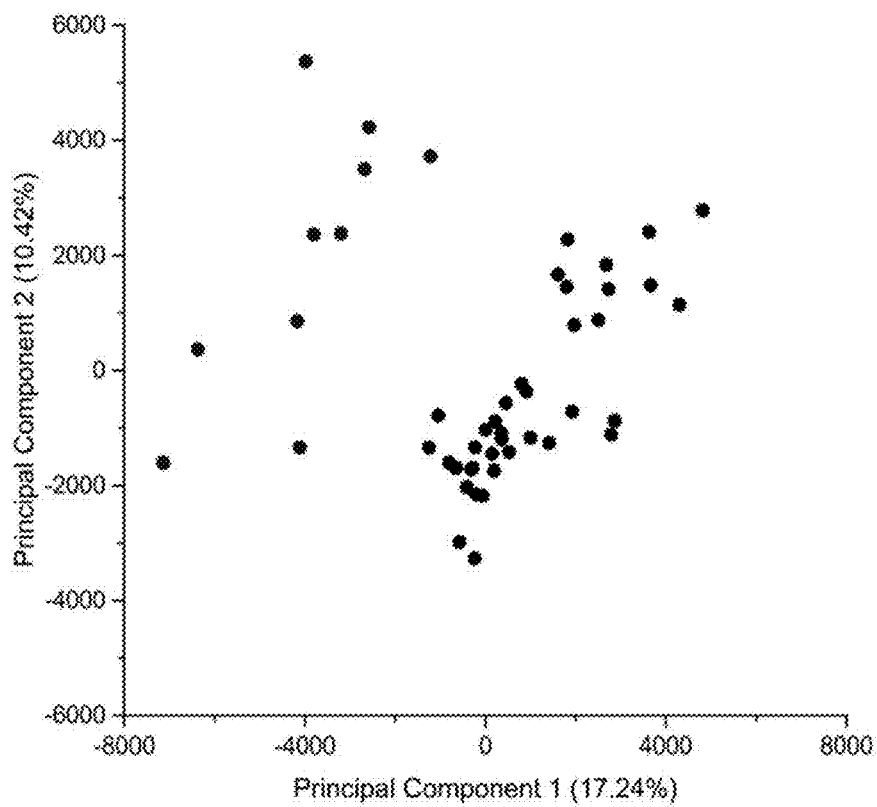
Figure 18A:
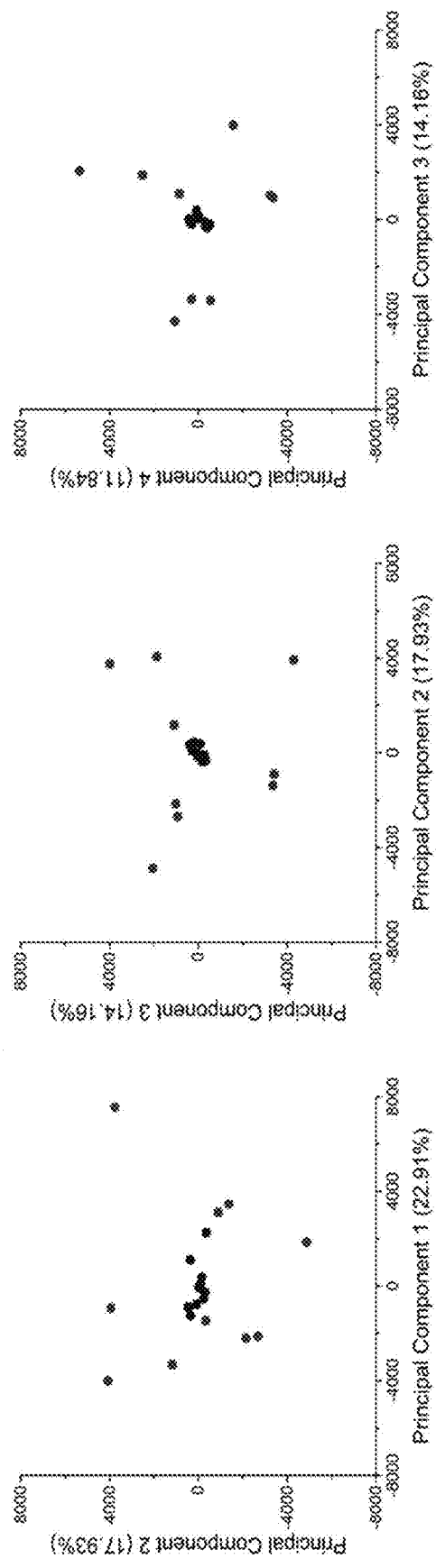
FIGS. 18A-18F provide the Principal Component Analyses of the second HEK293T clone.
Figure 18B:
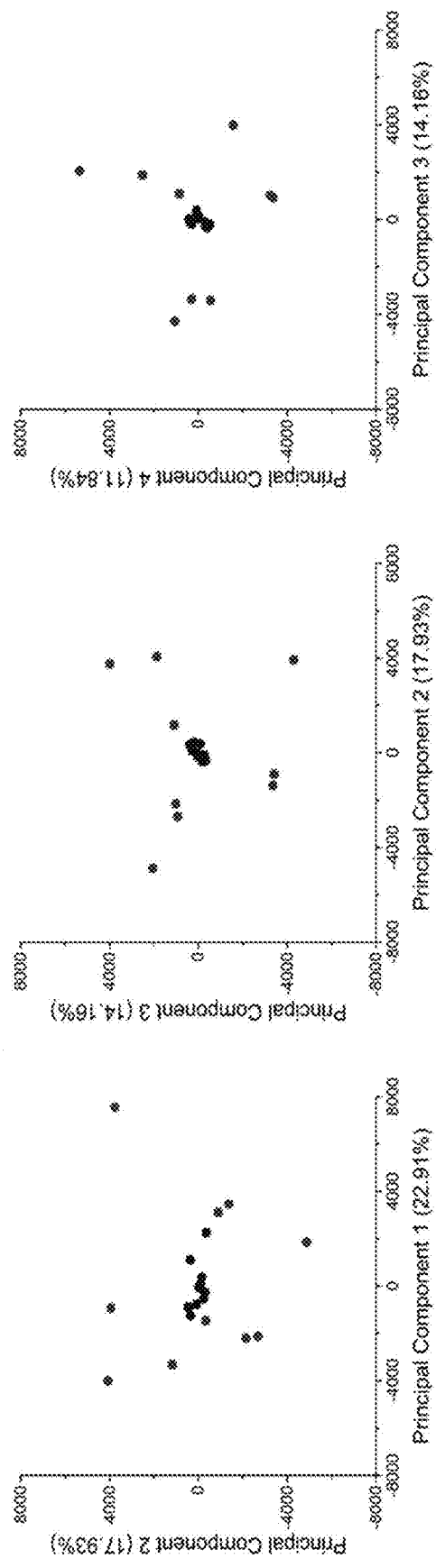
Figure 18C:
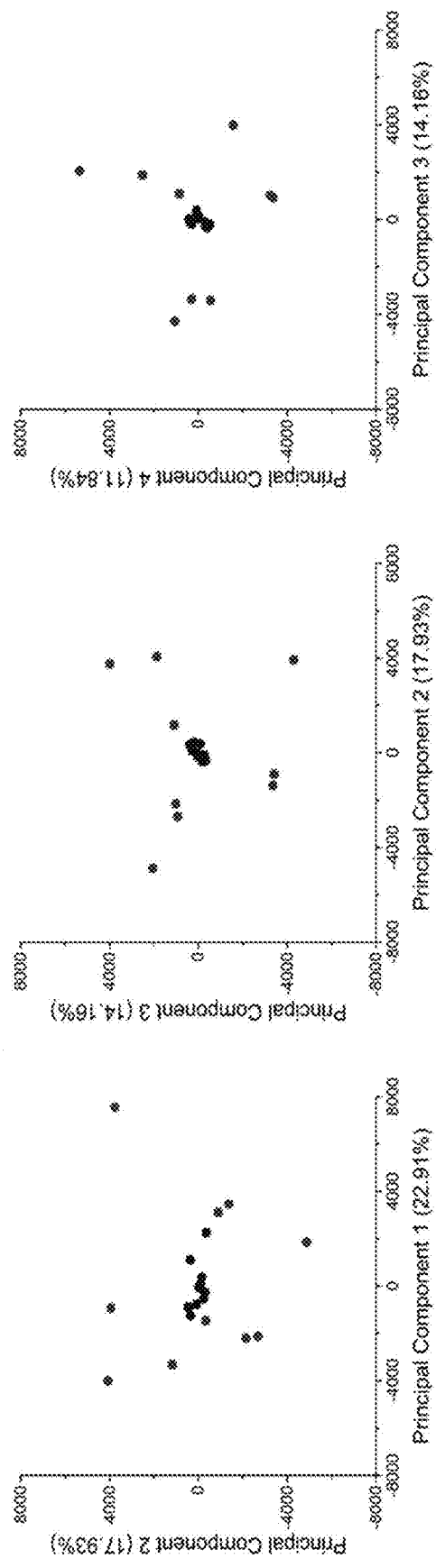
Figure 18D:
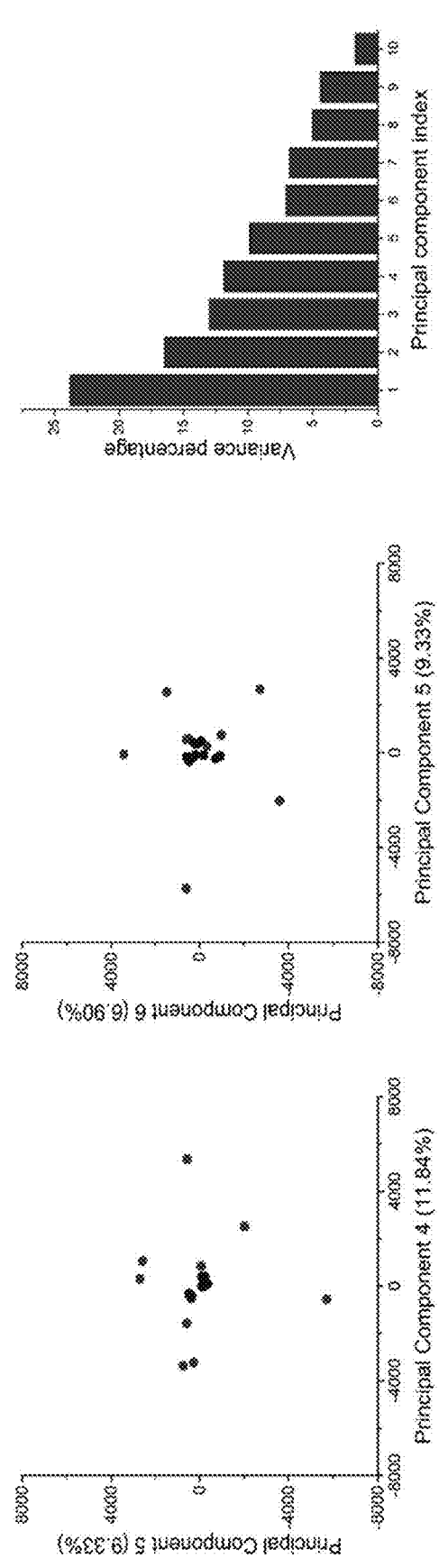
Figure 18E:
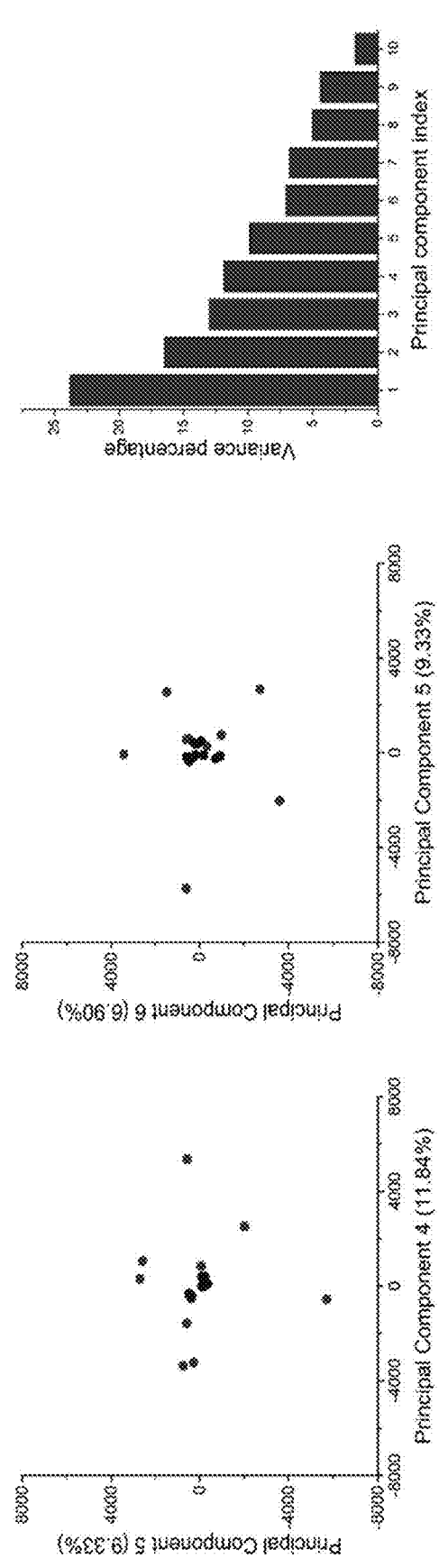
Figure 18F:
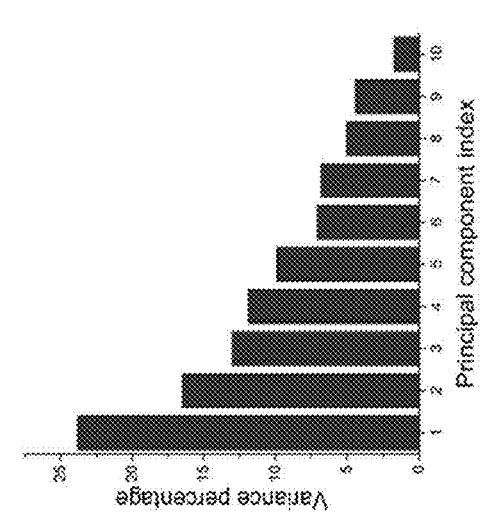
Figure 20:
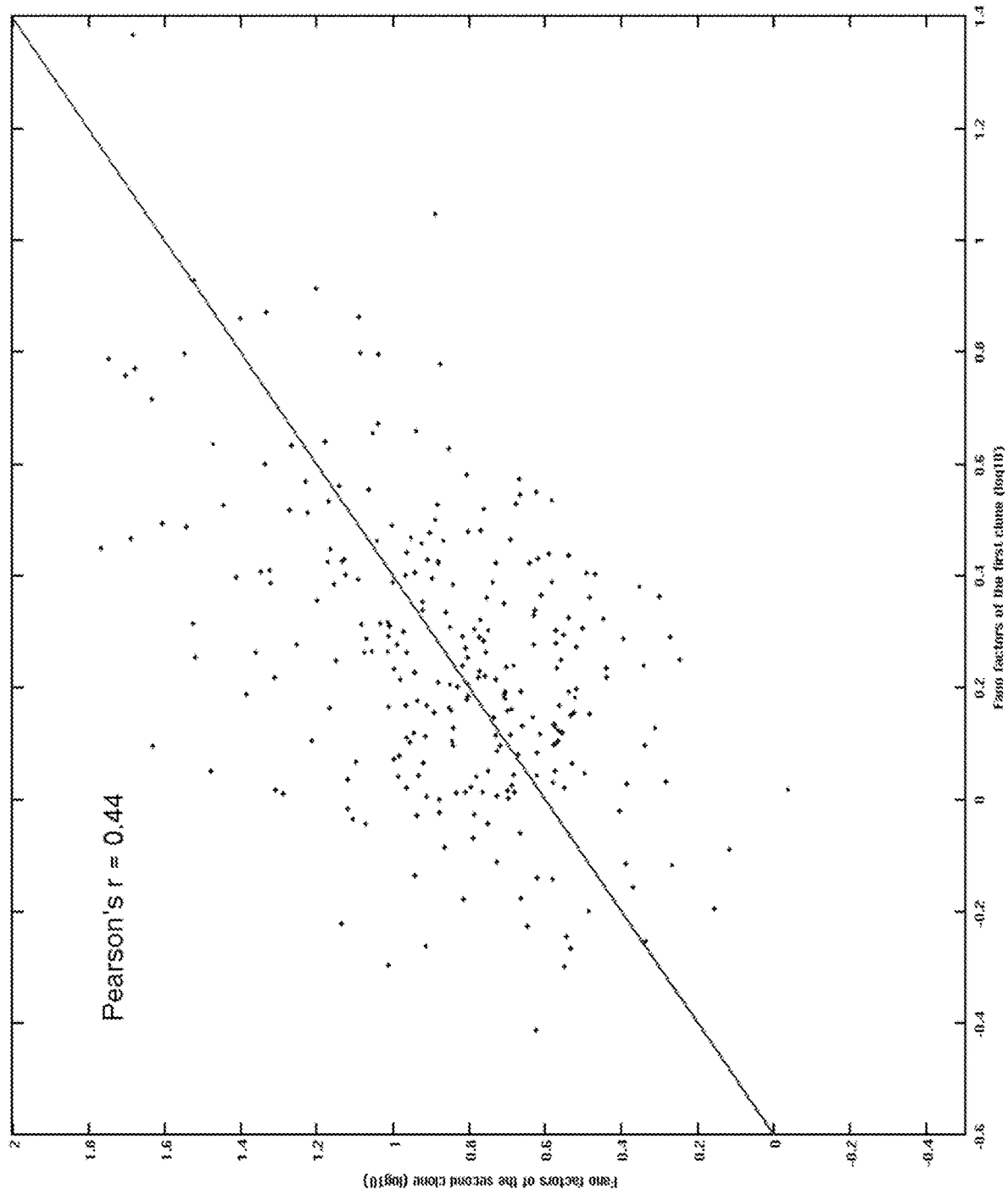
FIG. 20 shows the scatter plot of Fano factors for between two different HEK293T clones. The inventors found 274 genes in both clones with statistically significant transcriptional variations (FDR<0.3). The coefficient of correlation between the Fano factors of the two clones is equal to 0.44.

To address the potential clonal difference between the MATQ-seq sequenced HEK293T clone and the clones used in SMART-seq2 and SUPeR-seq, a different HEK293T clone (clone-2) was sequenced to assess clonal differences in general. 10 single cells and 10 single-cell averages were sequenced. We observed that mean expression levels correlate well between the two clones of single cells, while PCA captures some differences (FIGS. 17A-17B). Using the F-test, 292 genes with significant variation were found at FDR<0.1 and 1111 genes were found at FDR<0.3 for the second clone (FIGS. 18-19). 273 genes in both clones were identified with FDR<0.3 in F-tests. For these genes, Fano factors are also moderately correlated (r=0.44, FIG. 20). The inventors conclude that the two clones have decent similarity judged by the comparison of the mean expression level and variations.

In addition to HEK293T, MATQ-seq was performed using the normal breast epithelial cell line MCF10A. Similar PCA results were observed between the single cells and the single-cell averages (FIG. 21), indicating that MATQ-seq robustly detected transcriptional variation in a differentiated cell type.

Sensitivity has been a key limitation of single-cell RNA-seq methods to date and the low sensitivity also limits accuracy. MATQ-seq provides high sensitivity and accuracy for detecting subtle differences in gene expression between single cells of the same type, as well as the ability to capture non-polyadenylated RNAs. The inventors believe that the method will have broad applications in biological and clinical research.

Example 2

Exemplary Material and Methods

Cell culturing—HEK293T cells were grown in DMEM/High Glucose medium (ThermoFisher Scientific) with 10% FBS (Life Technologies) and 1% Penicillin-Streptomycin (Life Technologies). Cells were passed every 2-3 days. MCF10A cells were grown in DMEM/F12 medium with 5% Horse Serum, 20 ng/ml EGF, 100 ng/ml Cholera Toxin, 10 ug/ml Insulin, 500 ng/ml Hydrocortisone, and 1% Penicillin Streptomycin.

Single cell isolation and lysis—Cell lysis buffer containing 1 ul of 0.2% TRITON™ X100 (Sigma-Aldrich), 0.4 ul of primer mix (page purified GATdT primers (GTG AGT GAT GGT TGA GGA TGT GTG GAG N5T20 (SEQ ID NO:1) (1.5 µM)), page purified MALBAC primers (GTG AGT GAT GGT TGA GGA TGT GTG GAG N5G3 (SEQ ID NO:2), and GTG AGT GAT GGT TGA GGA TGT GTG GAG N5T3 (SEQ ID NO:3) (5 µM each)), 0.12 dNTP (10 mM each), 0.05 µl 0.1M DTT (Life Technology), and 2U RNASEOUT™ (Life Technologies) was prepared for every single cell. HEK293T cells were trypsinized and diluted in RNase-free PBS (Ambion). Single cells were mouth pipetted under a microscope into each PCR tube containing 1.6 µl of cell lysis buffer. For single-cell averages, 40 cells were mouth pipetted into 64ul of cell lysis buffer. Cells were lysed at 72° C. for 3 minutes and then transferred onto ice. For ERCC spike-in experiments, 1 µl of 1 to 80,000 diluted ERCC spike-ins was added to 40 µl of lysis buffer. 32 µl of spiked lysis buffer was removed in which 4 single cells were mouth pipetted. After lysis, one-twentieth of mixture was used to represent averaged one-fifth single cell with the spike-ins.

Reverse transcription and the second strand synthesis—Reverse transcription mix containing 0.8 µl 5× First Strand Buffer (Life Technologies), 0.2 µl 0.1M DTT, 4U RNASE-OUT™ (Life Technologies), 30U SUPERSCRIPT® III (Life Technologies), and 1.15 µl RNase-free water was prepared and was added into each tube containing lysed single cell (for single-cell averages, reverse transcription mix was proportionally added to the lysed samples, and mixed thoroughly; 4µl of the mix were then added into each PCR tube). SUPERSCRIPT® III has better thermo-stability but low template switching activity compared to SUPERSCRIPT® II.

10 cycles of annealing (ramping from 8° C. to 50° C.) was performed on Bio-Rad thermocycler. Residual primers were digested by 30 minutes at 37° C. and 20 minutes at 63° C. with 0.2 µl of T4 DNA Polymerase (New England Biolabs) treatment, followed by a digestion of 30 minutes at 37° C. and 20 minutes at 63° C. with 0.2 µl Exonuclease I (New England Biolabs) treatment (Exonuclease I is optional if RNA input is greater than 5pg). T4 DNA Polymerase and Exonuclease I were further inactivated by addition 0.2 µl of 20× Protease (Qiagen) at 37° C. for 30 minutes. Protease was inactivated at 72° C. for 20 minutes. RNase H (New England Biolabs) and RNase If (New England Biolabs) were 1:1 mixed. 0.2 µl of the enzyme mix were added to the samples, which were then incubated at 37° C. for 15 minutes and inactivated at 72° C. for 15 minutes. TdT terminal transferase (New England Biolabs) mixture containing 2.74 µl of PCR grade water, 0.4 µl 100 mM dCTP, 0.36 µl 10× TdT buffer, and 0.1 µl TdT was then added. Tailing reactions were performed at 37° C. for 15 minutes followed by a 15-minute heat inactivation at 72° C. For 2nd strand synthesis, 13.1 µl of PCR grade water, 0.125 µl of 100 mM MALBAC primer, 1.25 µl of dNTP (10 mM each), and 1.5 µl of 10× THERMOPOL® buffer was added. Samples were heated to 95° C. for 30 seconds. 0.4 µl of deepvent exo- (New England Biolabs) polymerase was added at 48° C. 10 cycles of multiple annealing 48° C. for 20 seconds, 72° C. for 1 minute was performed to convert the first strand cDNA into double stranded full amplicons.

PCR amplification and purification—PCR mix containing 21 µl 10× THERMOPOL® Buffer, 1.2 µl 100 µM GAT primer (GTG AGT GAT GGT TGA GGA TGT GTG GAG; SEQ ID NO:4), 5 µl 10 mM each dNTP, 185 µl PCR grade water, and 4.5 µl DEEP VENT® exo-DNA polymerase was mixed with the preamp reactions. Each reaction was split into 8 PCR tubes. The PCR program was as follows: 95° C. incubation for 30 seconds, 24 cycles of PCR (95° C. 15 seconds, 60° C. 20 seconds, and 72° C. 2 minutes), followed by a 5-minute incubation at 72° C. PCR reactions were purified using either Qiagen PCR cleanup kit or 0.9× AMPURE® beads (Beckman Coulter).

Library preparation and sequencing—For library preparation, 500 ng of cDNA was used. cDNA was sheared to 200 bp using Covaris 5220 sonicator. End repair was performed using NEBNEXT® End Repair Module (New England Biolabs). AMPURE® beads based size selection was performed at 0.75× (discard beads) followed by an addition of 0.45× (1.2× in total) AMPURE® beads (discard supernatant). Obtained products were A-tailed by Klenow exo-DNA polymerase (New England Biolabs). T4 DNA quick ligase (New England Biolabs) was used to ligate Illumina TRUSEQ™ adaptors to samples. 1× AMPURE® beads were used to purify the library into 30 µl of PCR grade water. 4 µl of the product was added to PCR mix containing 10 µl of 2× KAPA HIFI™ HOTSTART® READYMIX™ (Kapa Biosystems), 1 µl of TRUSEQ™ PCR primer (10 µM each), and 5 µl of PCR grade water. After incubation at 95° C. for 2 minutes, 5 cycle of PCR (95° C. for 15 seconds, 60° C. for 15 seconds, 72° C. for 30 seconds) was performed. End products were purified using 1× AMPURE® beads. KAPA library quantification kit was used to quantify the concentration of each library. Libraries were pooled as instructed by Illumina protocol. The pooled libraries were then sequenced on Illumina NEXTSEQ™ 500 platform using 150 cycle sequencing kits.

ERCC dilution and mapping percentage—In previous studies using SMART-seq chemistry (3,4), where ~4-million-fold diluted ERCC standard was spiked in a single cell, more than 5% of the reads were mapped to ERCC. With MATQ-seq, when 2-million-fold diluted ERCC standard was spiked into one-fifth of a single cell, 5.76±1.54% of reads are mapped to ERCC. This result suggests that MATQ-seq produce 10-fold more cDNA for PCR amplification compared to the previous studies. This increase is likely due to the improved capturing efficiency as well as the efficient detection of non-polyadenylated transcripts allowed by MATQ-seq chemistry.

Figures 22A, 22B, 22C:
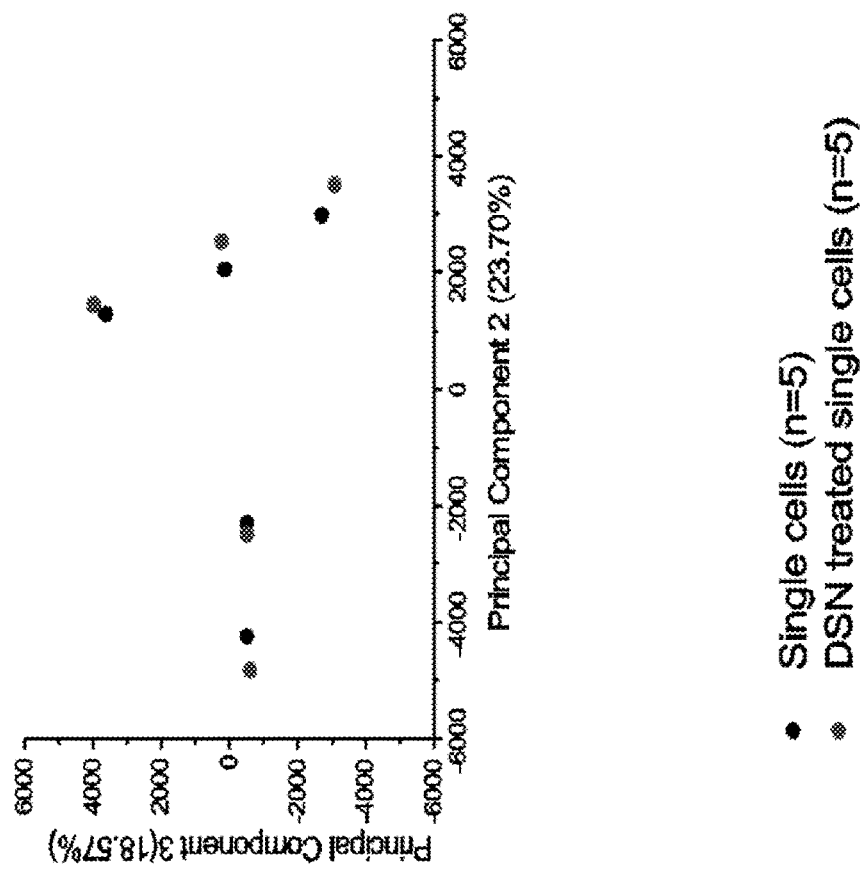
FIGS. 22A-22C illustrate the effects of Duplex-specific Nuclease Treatment on Transcriptome. Principal Component Analyses of single cells before and after Duplex-specific Nuclease treatment. The single cells were treated by Duplex-specific Nuclease to remove DNA fragments amplified from ribosomal RNA. The samples before and after treatment are located in close proximity in the top 4 principal components (~90% of the variance), demonstrating that ribosomal removal does not significantly alter the gene expression profiles.
Figure 23D:
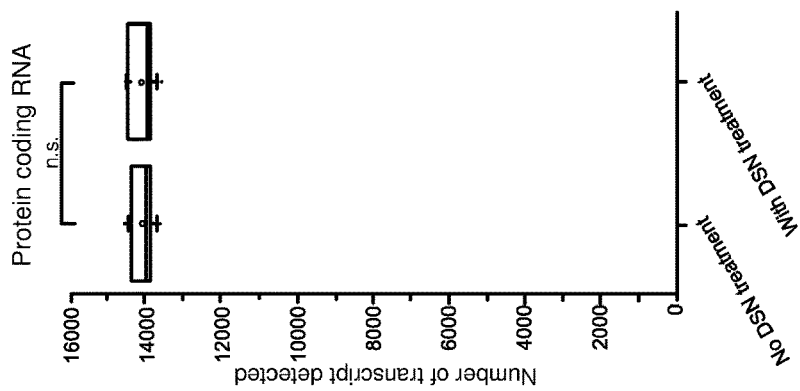
FIG. 23 shows the effect of Duplex-specific Nuclease treatment on different types of genes. Consistent with the PCA analyses (FIG. 22), DSN treatment did not significantly alter the (23A) total gene detection number, neither the numbers of different types of genes identified (23B-23D). miRNAs were likely detected in their pre-mature form since small amplicons directly generated miRNA will not be efficiently amplified. n=5 for each group. Lower and upper hinges correspond to 25th and 75th percentiles, upper and lower whiskers represent the standard deviation, square correspond to mean, and each dot in the plot represents one sample.
Figure 23C:
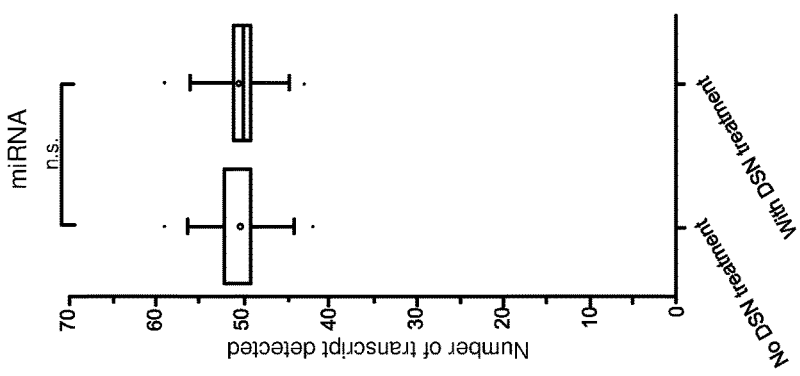
Figure 23B:
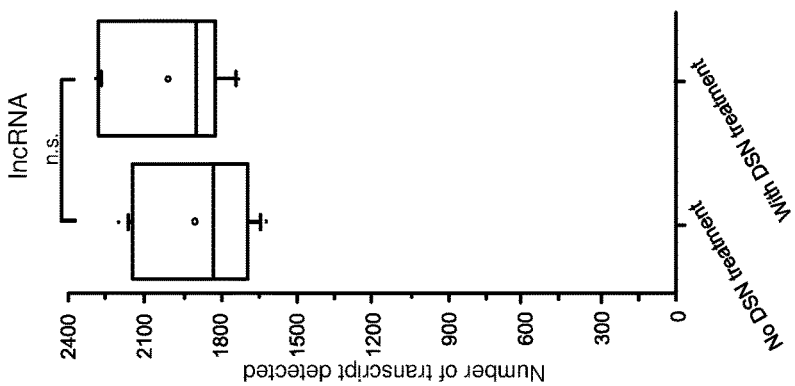
Figure 23A:
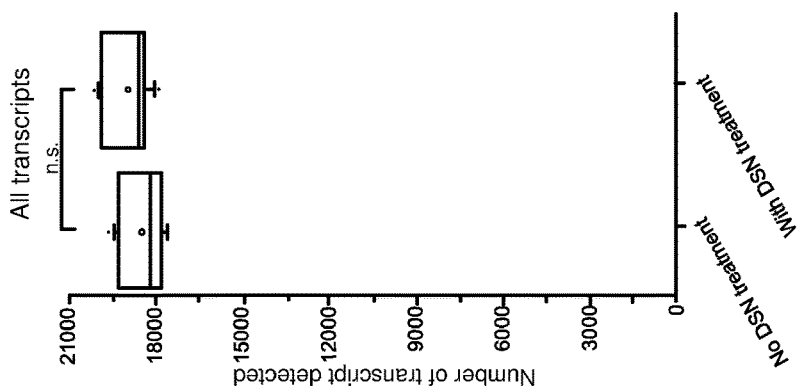

Optional duplex-specific nuclease (DSN) treatment for removing ribosomal cDNA—DSN treatment was used to remove the majority of ribosomal cDNA (Zhulidov, et al., 2004). After KAPA quantification and library pooling, 9 µl of 1 nM of pooled library was added to 10 µl of 2× KAPA HIFI™ HOTSTART® READYMIX™ (Kapa Biosystems), 1 µl of TRUSEQ™ PCR primer (10 µM each). PCR was performed for 5 cycles. 1× AMPURE® beads were used to purify the end product into 10 µl of PCR grade water. A reaction mixture of 5 µl of the purified library, 1 µl of 10× DSN buffer (Evrogen), 3 µl of PCR grade water was made. The reaction mixture was heated on a thermocycler to 95° C. for 30 seconds, and was then incubated at 80° C. for 4 hours. 1 µl of preheated Duplex-Specific Nuclease was added to the mixture. The reaction mixture was then incubated at 80° C. for 15 minutes. Preheated Stop solution (Evrogen) was added to stop the reaction. 20 µl of AMPURE® beads was used to purify the DSN treated library. KAPA quantification kit (Kapa Biosystems) was used to quantify the DSN treated library. The gene expression profiles are consistent before and after the procedure (FIGS. 22-23). DSN treatment can effectively reduce the ribosomal reads from ~50% to ~10% in total sequencing reads. Also, to efficiently detect low copy ERCC spike-ins, the pooled averaged one-fifth single-cell samples libraries were treated with DSN prior to sequencing.

Figure 25:
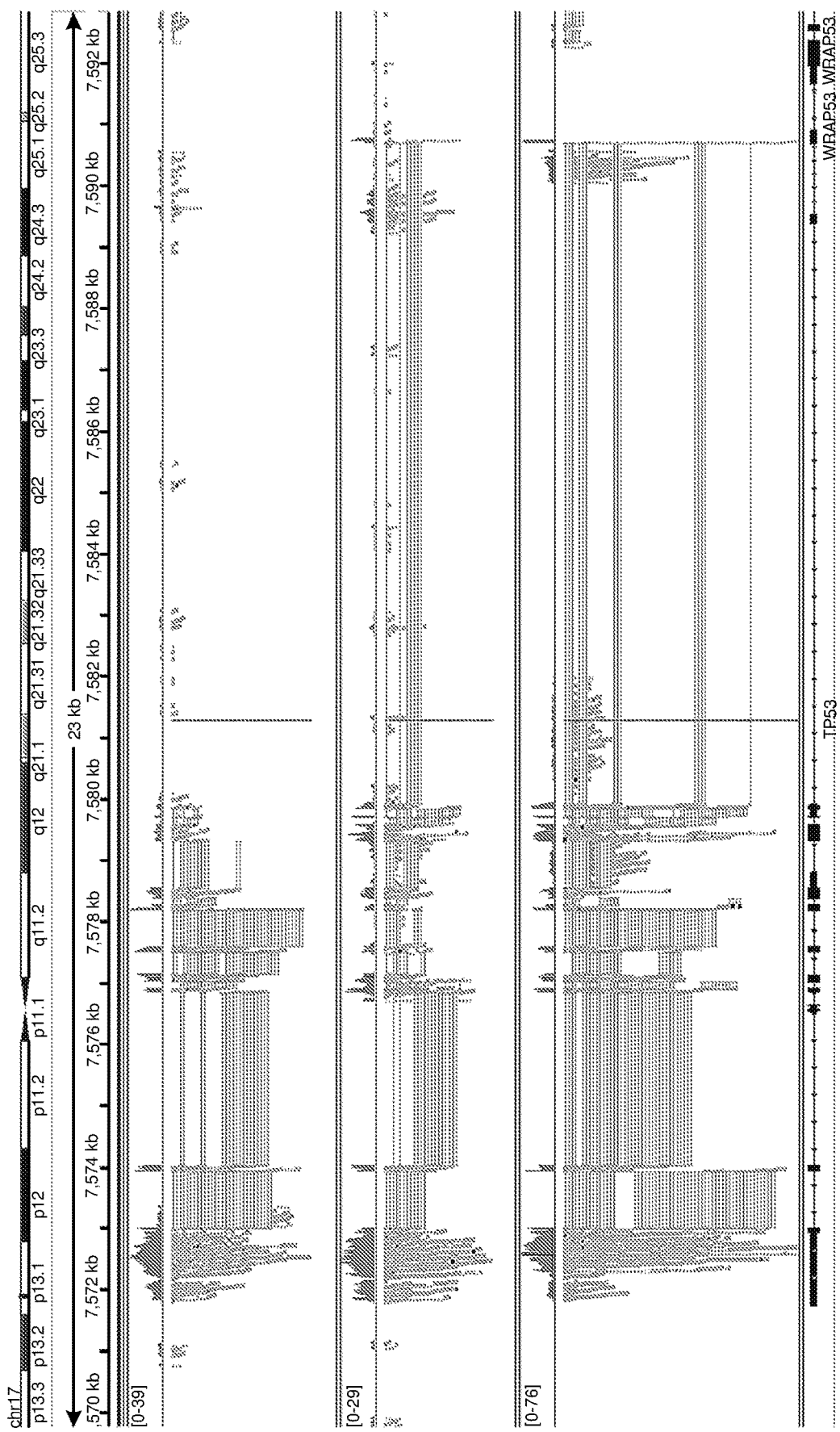
FIG. 25 is a representative alignment snapshot for MATQ-seq data in IGV. The gene shown above is TP53. For example, for the first cell on the top, 42 reads are aligned to the exon regions, 14 are indexed reads. The RPKM value is 93.0 and APKM (Amplicons per Kilobases per Million Amplicons) value is 74.4.

Trimming and mapping—The raw sequencing data was trimmed using skewer package to remove primer sequences. After removing primer sequences, 14 bases were further trimmed to remove the amplicon index bases and the extra bases due to dC-tailing. The reads were mapped to the genome using Tophat. Only the reads from Tophat with mapping score equals to 50 were used, which indicates unique mapping. Python scripts using HT-seq package were written to parse the amplicon index information between the bam files and the corresponding fastq files. This allowed for the retrieval of index sequences associated with the mapped reads. The gencode annotation release 19 (GRCh37.p13) was used for transcript annotation. When the reads are assigned to a gene, only the regions that can be uniquely assigned to this gene are used to avoid multiple assignment. The gene coverage, GC % and the fragment size distributions are given in FIG. 24. One example of mapping is given for TP53 in FIG. 25.

Quantification of gene expression level—After retrieving the amplicon index information and the mapping information of the reads, a separate python script was used to count the number of unique amplicon index sequences associated with each gene including to the whole gene body, to the exon region only, and to the intron region only. The numbers of total amplicons were summarized to normalize the gene expression. The unit of APM is defined as the amplicons per one million total amplicons. Gene expression level=the number of unique amplicon indexes of a gene/the total number of indexes of all genes×1,000,000. To avoid the inaccurate counting of the extremely highly expressed genes due to index saturation, genes were excluded from the analysis when the number of amplicons exceeds 800 (three genes were excluded from the analysis due to the potential underestimation of amplicon indexes).

Percentage of genes detected repeatedly between pairs of single cells—Genes were binned according to the highest expression level of the two samples. Down samplings were performed when necessary to ensure equal footing comparison. SMART-seq2 was reanalyzed with the same pipeline as MATQ-seq. A gene was considered detected if it had reads per million mapped reads (RPM) value higher than 0.1 in both samples. The mean percentage and 95% confidence interval were reported.

F-test of variances—The null hypothesis of F-test between single cells and single-cell averages is the variances are equal. To avoid inefficient sampling of Poisson noise in single-cell averages, only the genes that are detected in all single-cell averages were selected for testing. Two-tailed tests were used for all the F-tests described in the paper.

The estimation of the number of amplicons for Fano factor calculation—The gene expression values in the unit of APM is rescaled to allow the distribution C.V. versus the mean follows the relation:

$$cv = 1/\sqrt{mean}$$

(based on Poisson distribution). As shown in FIG. 26, the expression level renormalized by one million amplicons does not overlap with the linear line. When the gene expression is renormalized by 100 k amplicons, the distribution overlap well with the linear line of $$y = 1/\sqrt{x},$$

suggesting this renormalization fits the single cell averages' data into Poisson distribution.

The histogram of gene expression ratio—The histograms of gene expression ratio were generated by the following procedure. The ratio of gene expression level for every gene between any pair of single cells were calculated and binned into a histogram. The pair of cells was randomly assigned to the denominator and numerator. If the gene is not expressed, the value of the ratio is assigned as NaN. The advantage of this analysis is that the calculated ratios are nonparametric. Also the ratios do not depend on the absolute gene expression level, so the variations of the highly expressed genes will not weigh more than the lowly expressed genes. In addition, the height of the columns also shows the number of genes being reproducibly detected.

PCA for identifying technical bias and variations—In PCA data, when the single-cell averages do not project at the center of single cells, this indicates that technical noises dominate the biological noises. For the variance analysis, only the genes whose expressions are detected in all single-cell averages were focused on to warrant the robust statistics.

Statistical analyses in MATLAB—F-tests for the comparison of variance between the single cells and the single-cell averages were performed using vartest2 in MATLAB. KS tests were performed to test whether the gene expression in the single-cell averages follows the normal distribution using kstest function in MATLAB._PCA analyses were performed using pca function in MATLAB.

TFBS analysis—Transcription factor binding analysis was carried out using The Database for Annotation, Visualization and Integrated Discovery (DAVID) (Huang, et al., 2009).

Figure 7:
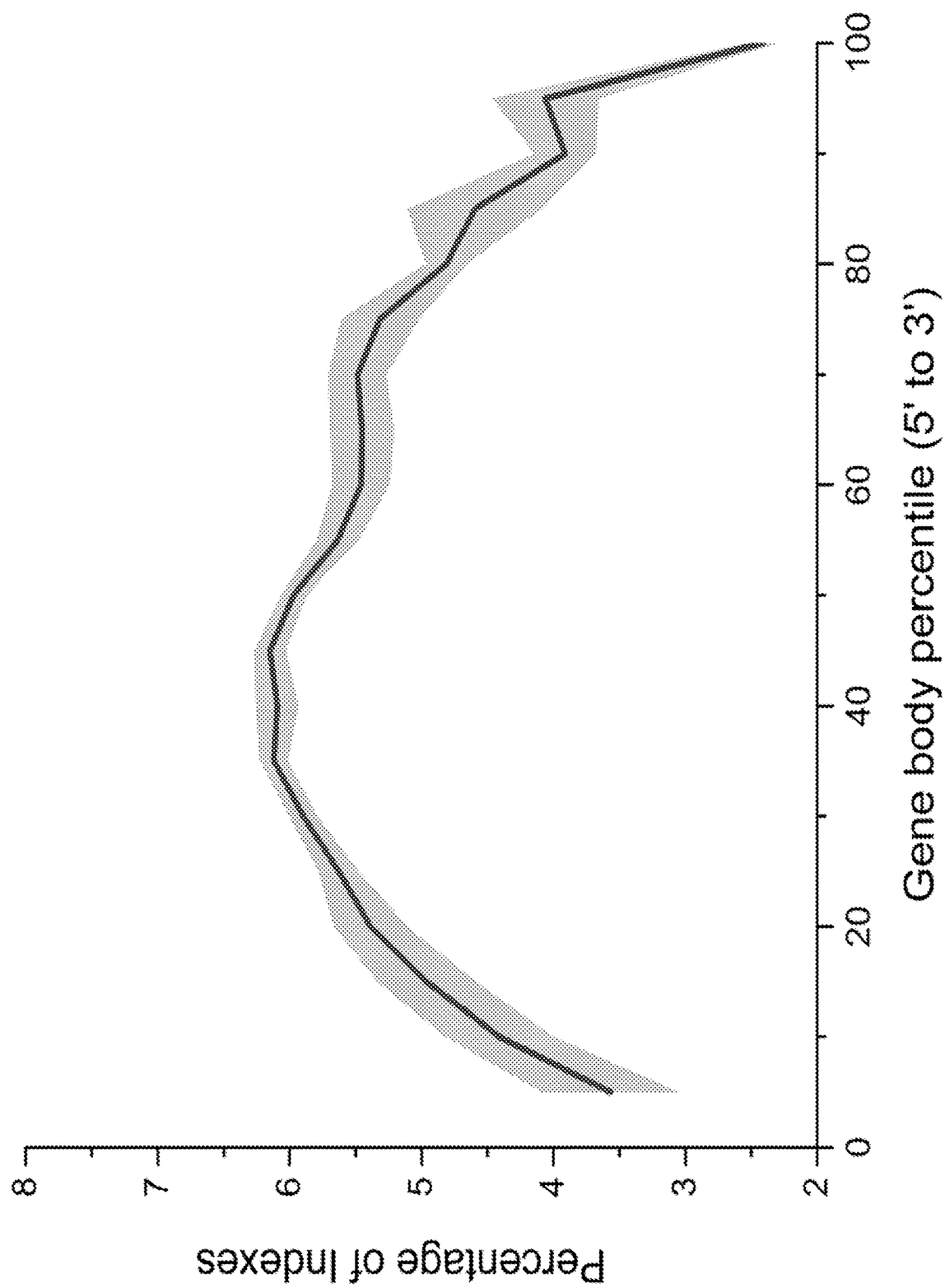
FIG. 7 shows the distribution of indexed amplicon coverage on genes. The red line is the average coverage of the 10 HEK293T single cells. The indexes distribute relatively even across genes body, indicating there is no significant directional bias for MATQ-seq. The shaded area indicates the S.E.M.
Figure 27:
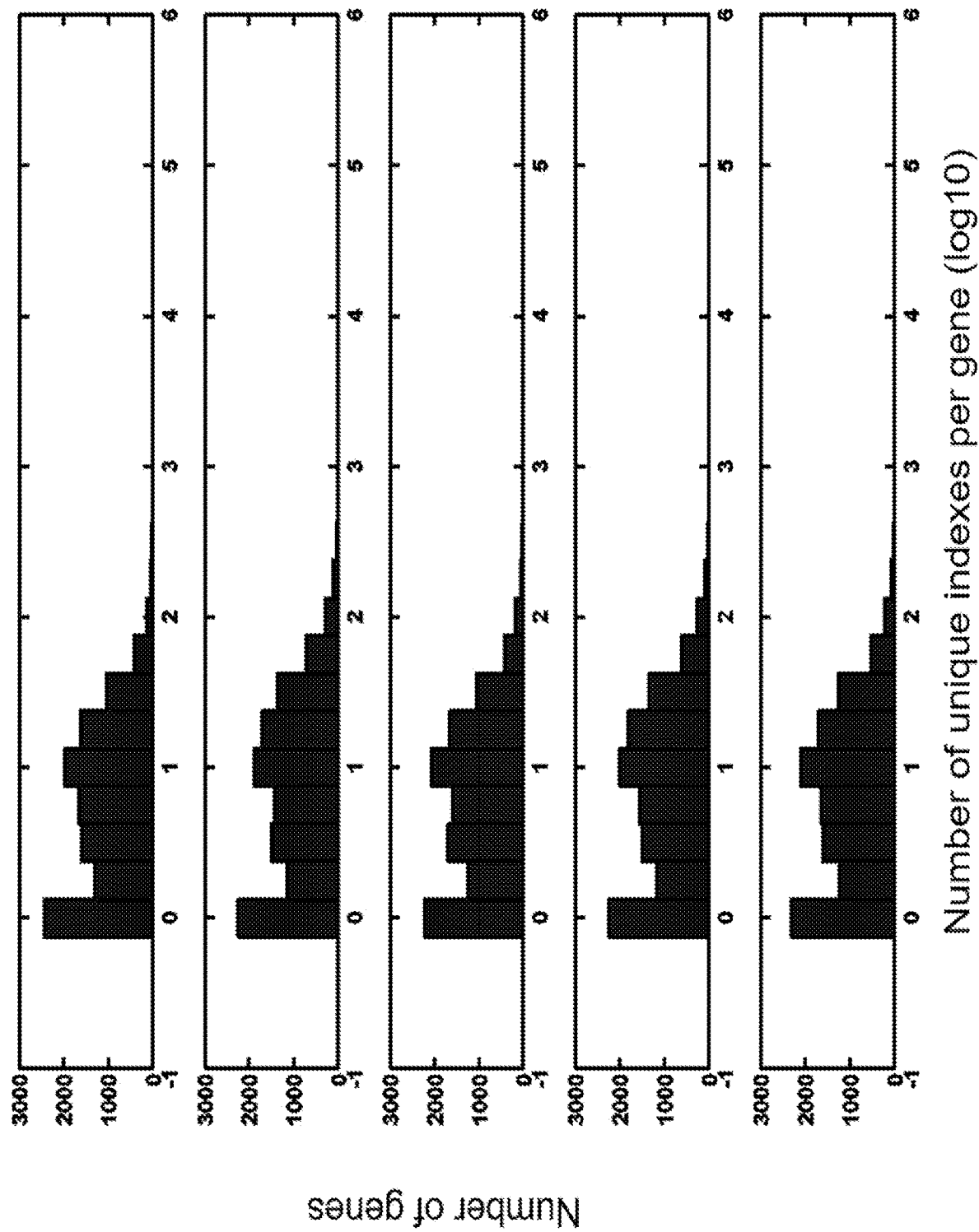
FIG. 27 provides the histogram of unique index number for detected genes in MATQ-seq. The number are the exact number collected from sequencing data, not the normalized value (APM). Each plot represents one single HEK293T cell. 5 single cells are plotted above.

Amplicon index distribution along the gene body and statistics—The reads with amplicon indexes do not show significant bias distributed along the mRNA (FIG. 7). The histograms of the unique amplicon number for detected genes are plotted as a histogram in FIG. 27.

Estimating the rate of non-unique amplicon indexes (barcodes)—In order to identify amplicon indexes that result from hybridization of the same adaptor at multiple loci, high confidence SNPs were identified using the HaplotypeCaller of GATK (Table 4). SNPs covered by more than one index with the same starting position were then collected. Reads with the same index sequence that carry the reference base rather than the alternative base in the SNP locus suggest a sequencing error; three such reads were required to filter out the error. The frequency of these events was used to estimate the upper limit of the rate of non-unique indexes, which is ~0.7%±0.6% based on sequencing data from 10 HEK293T cells. Promiscuous primer hybridization is more common in regions with low sequence complexity.

TABLE 4

SNP associated reads and indexes

| Single cell, HEK293T | SNPs detected based on reads | Total number of indexes covering SNP loci | The percentage of conflicting indexes |
|---|---|---|---|
| #1 | 10804 | 6407 | 0.3% |
| #2 | 12692 | 6619 | 0.9% |
| #3 | 17800 | 12132 | 1.7% |
| #4 | 5911 | 4238 | 1.2% |
| #5 | 10451 | 6019 | 1.9% |
| #6 | 7786 | 3947 | 0.5% |
| #7 | 6741 | 3489 | 0.2% |
| #8 | 8602 | 6270 | 0.7% |
| #9 | 6923 | 4270 | 0.6% |
| #10 | 12545 | 8074 | 0.5% |

Data and code availability—Single-cell RNA-seq data are deposited in GEO under accession GSE78968. All other data are provided herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

REFERENCES

1. Battich N, Stoeger T, Pelkmans L. Control of Transcript Variability in Single Mammalian Cells. Cell. 2015; 163 (7):1596-610. doi: 10.1016/j.cell.2015.11.018.
2. Briese M, Saal L, Appenzeller S, Moradi M, Baluapuri A, Sendtner M. Whole transcriptome profiling reveals the RNA content of motor axons. Nucleic acids research. 2015. doi: 10.1093/nar/gkv1027. PubMed PMID: 26464439.
3. Cai L, Friedman N, Xie X S. Stochastic protein expression in individual cells at the single molecule level. Nature. 2006; 440(7082):358-62. doi: 10.1038/nature04599. PubMed PMID: 16541077.
4. Chapman A R, He Z, Lu S, Yong J, Tan L, Tang F, et al. Single cell transcriptome amplification with MALBAC. PLoS One. 2015; 10(3):e0120889. doi: 10.1371/journal.pone.0120889. PubMed PMID: 25822772; PubMed Central PMCID: PMCPMC4378937.
5. Elowitz M B, Levine A J, Siggia E D, Swain P S. Stochastic gene expression in a single cell. Science. 2002; 297(5584):1183-6. doi: 10.1126/science.1070919. PubMed PMID: 12183631.
6. Fan X, Zhang X, Wu X, Guo H, Hu Y, Tang F, et al. Single-cell RNA-seq transcriptome analysis of linear and circular RNAs in mouse preimplantation embryos. Genome biology. 2015; 16:148. doi: 10.1186/s13059-015-0706-1. PubMed PMID: 26201400; PubMed Central PMCID: PMCPMC4511241.
7. Golding I, Paulsson J, Zawilski S M, Cox E C. Real-time kinetics of gene activity in individual bacteria. Cell. 2005; 123(6):1025-36. doi: 10.1016/j.cell.2005.09.031. PubMed PMID: 16360033.
8. Grun D, Kester L, van Oudenaarden A. Validation of noise models for single-cell transcriptomics. Nature methods. 2014; 11(6):637-40. doi: 10.1038/nmeth.2930. PubMed PMID: 24747814.
9. Hashimshony T, Wagner F, Sher N, Yanai I. CEL-Seq: single-cell RNA-Seq by multiplexed linear amplification. Cell reports. 2012; 2(3):666-73. doi: 10.1016/j.celrep.2012.08.003.
10. Huang da W, Sherman B T, Lempicki R A. Bioinformatics enrichment tools: paths toward the comprehensive functional analysis of large gene lists. Nucleic acids research. 2009; 37(1):1-13. doi: 10.1093/nar/gkn923. PubMed PMID: 19033363; PubMed Central PMCID: PMC2615629.
11. Islam S, Zeisel A, Joost S, La Manno G, Zajac P, Kasper M, et al. Quantitative single-cell RNA-seq with unique molecular identifiers. Nature methods. 2014; 11(2):163-6. doi: 10.1038/nmeth.2772. PubMed PMID: 24363023.
12. Jaitin D A, Kenigsberg E, Keren-Shaul H, Elefant N, Paul F, Zaretsky I, et al. Massively parallel single-cell RNA-seq for marker-free decomposition of tissues into cell types. Science. 2014; 343(6172):776-9. doi: 10.1126/science.1247651. PubMed PMID: 24531970; PubMed Central PMCID: PMCPMC4412462.
13. Kivioja T, Vaharautio A, Karlsson K, Bonke M, Enge M, Linnarsson S, et al. Counting absolute numbers of molecules using unique molecular identifiers. Nat Meth. 2012; 9(1):72-4. doi: 10.1038/nmeth.1778.
14. Kuanwei Sheng C Z. Multiple Annealing and dC-Tailing based Quantitative single-cell RNA-seq (MATQ-seq). Protocol Exchange. 2016. doi: 10.1038/protex.2016.088.
15. Marinov G K, Williams B A, McCue K, Schroth G P, Gertz J, Myers R M, et al. From single-cell to cell-pool transcriptomes: stochasticity in gene expression and RNA splicing. Genome Res. 2014; 24(3):496-510. doi: 10.1101/gr.161034.113. PubMed PMID: 24299736; PubMed Central PMCID: PMCPMC3941114.
16. Picelli S, Bjorklund A K, Faridani O R, Sagasser S, Winberg G, Sandberg R. Smart-seq2 for sensitive full-length transcriptome profiling in single cells. Nature methods. 2013; 10(11):1096-8. doi: 10.1038/nmeth.2639. PubMed PMID: 24056875.
17. Raj A, van Oudenaarden A. Nature, nurture, or chance: stochastic gene expression and its consequences. Cell. 2008; 135(2):216-26. doi: 10.1016/j.cell.2008.09.050. PubMed PMID: 18957198; PubMed Central PMCID: PMC3118044.
18. Ramskold D, Luo S, Wang Y C, Li R, Deng Q, Faridani O R, et al. Full-length mRNA-Seq from single-cell levels of RNA and individual circulating tumor cells. Nature biotechnology. 2012; 30(8):777-82. doi: 10.1038/nbt.2282. PubMed PMID: 22820318; PubMed Central PMCID: PMC3467340.
19. Streets A M, Zhang X, Cao C, Pang Y, Wu X, Xiong L, et al. Microfluidic single-cell whole-transcriptome sequencing. Proceedings of the National Academy of Sciences of the United States of America. 2014; 111(19): 7048-53. doi: 10.1073/pnas.1402030111.
20. Tang F, Barbacioru C, Wang Y, Nordman E, Lee C, Xu N, et al. mRNA-Seq whole-transcriptome analysis of a single cell. Nature methods. 2009; 6(5):377-82. doi: 10.1038/nmeth.1315. PubMed PMID: 19349980.
21. Wu A R, Neff N F, Kalisky T, Dalerba P, Treutlein B, Rothenberg M E, et al. Quantitative assessment of single-cell RNA-sequencing methods. Nature methods. 2014; 11(1):41-6. doi: 10.1038/nmeth.2694. PubMed PMID: 24141493; PubMed Central PMCID: PMC4022966.
22. Zhulidov P A, Bogdanova E A, Shcheglov A S, Vagner L L, Khaspekov G L, Kozhemyako V B, et al. Simple cDNA normalization using kamchatka crab duplex specific nuclease. Nucleic acids research. 2004; 32(3). doi: 10.1093/nar/gnh031.
23. Zong C, Lu S, Chapman A R, Xie X S. Genome-wide detection of single nucleotide and copy number variations of a single human. Science. 2012; 338:1622-6.

What is claimed is:

1. A method of amplifying polyadenylated and non-polyadenylated RNA from one or more cells, comprising the steps of:
    exposing RNA from the one or more cells to a first plurality of primers and to at least one reverse transcriptase to produce a reaction mixture;
    subjecting said reaction mixture to conditions that allow annealing of the primers to the RNA and first-strand cDNA synthesis to produce extended DNA strands;
    digesting unannealed primers;
    inactivating enzymes in the reaction mixture;
    digesting RNA in the reaction mixture;
    tailing the 3' ends of the extended DNA strands;
    generating second-strand synthesis using a second plurality of primers and at least one DNA polymerase under suitable conditions to produce double-stranded full amplicons corresponding to the polyadenylated and non-polyadenylated RNA, wherein the primers in the first plurality, second plurality, or both comprise the following formula:

$$5'X_nY_mZ_p\ 3',$$

wherein n is 20-40 nucleotides and X is 40%-60% G-rich or 40%-60% C-rich, wherein Y is any nucleotide and m is 5-8 nucleotides, and wherein Z is a T or a G when X is G-rich or Z is a C when X is C-rich and p is 2-20 nucleotides.

2. The method of claim 1, wherein m is 5 nucleotides.
3. The method of claim 1, wherein p is 3 nucleotides.
4. The method of claim 1, wherein p is 20 nucleotides.
5. The method of claim 1 wherein n is 25-35 nucleotides.
6. The method of claim 1, wherein n is 24-28 nucleotides.
7. The method of claim 1, wherein the unannealed primers are digested with at least one of a DNA polymerase and/or exonuclease possessing 3' to 5' exonuclease activity.

8. The method of claim 1, wherein tailing the 3' ends of the extended DNA strands occurs with at least one terminal deoxyribonucleotide transferase.

9. The method of claim 1, wherein the tailing of the 3' ends of the extended DNA strands utilizes deoxycytosine triphosphate or deoxyguanosine triphosphate.

10. The method of claim 1, wherein the tailing step occurs at a range of temperature of 10-45° C.

11. The method of claim 1, wherein first strand cDNA synthesis occurs at a temperature in the range of 8-50° C. and second strand synthesis occurs at a temperature in the range of 48-72° C.

12. The method of claim 1, wherein the generating step comprises annealing of the second plurality of primers to the 3' end of amplicons at a temperature in the range of 30-55° C.

13. The method of claim 1, wherein the primers in the second plurality of primers comprise an amplicon index to control for polymerase chain reaction efficiency bias.

14. The method of claim 1, wherein the double stranded full amplicons are further amplified by linear or nonlinear methods.

15. The method of claim 14, wherein at least some of the amplified amplicons are sequenced.

16. The method of claim 1, wherein the one or more cells is isolated from an individual.

17. The method of claim 16, wherein the one or more cells are circulating tumor cells.

18. The method of claim 1, wherein the one or more cells is from a developing fetus or wherein the one or more cells are stem cells, or wherein the one or more cells is isolated from an individual's neoplasia or wherein the one or more cells are cells that have been modified to express Cas9 and one or more single guide RNAs (sgRNAs).

* * * * *

SEQUENCE LISTING

<160> NUMBER OF SEQ ID NOS: 4

<210> SEQ ID NO 1
<211> LENGTH: 52
<212> TYPE: DNA
<213> ORGANISM: Artificial Sequence

```
<220> FEATURE:
<223> OTHER INFORMATION: Synthetic Primer
<220> FEATURE:
<221> NAME/KEY: misc_feature
<222> LOCATION: (28)..(32)
<223> OTHER INFORMATION: n is a, c, g, or t

<400> SEQUENCE: 1
gtgagtgatg gttgaggatg tgtggagnnn nntttttttt tttttttttt tt           52

<210> SEQ ID NO 2
<211> LENGTH: 35
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (28)..(32)
<223> OTHER INFORMATION: n is a, c, g, or t

<400> SEQUENCE: 2
gtgagtgatg gttgaggatg tgtggagnnn nnggg                              35

<210> SEQ ID NO 3
<211> LENGTH: 35
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (28)..(32)
<223> OTHER INFORMATION: n is a, c, g, or t

<400> SEQUENCE: 3
gtgagtgatg gttgaggatg tgtggagnnn nnttt                              35

<210> SEQ ID NO 4
<211> LENGTH: 27
<212> TYPE: DNA
<213> ORGANISM: Artificial Sequence
<220> FEATURE:
<223> OTHER INFORMATION: Synthetic Primer

<400> SEQUENCE: 4
gtgagtgatg gttgaggatg tgtggag                                       27
```